(12) United States Patent
Seo et al.

(10) Patent No.: US 12,187,717 B2
(45) Date of Patent: *Jan. 7, 2025

(54) COMPOUND AND USE THEREOF IN TREATING AUTOIMMUNE DISEASES

(71) Applicant: PARENCHYMA BIOTECH INC., Busan (KR)

(72) Inventors: Su Kil Seo, Busan (KR); Eun Hye Yoon, Busan (KR); Soung Min Lee, Busan (KR); Hae Jeong Won, Busan (KR); Won Hee Jang, Busan (KR); Chae Eun Kim, Busan (KR)

(73) Assignee: PARENCHYMA BIOTECH INC., Busan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/239,842

(22) Filed: Aug. 30, 2023

(65) Prior Publication Data

US 2023/0406848 A1 Dec. 21, 2023

Related U.S. Application Data

(63) Continuation of application No. 18/138,817, filed on Apr. 25, 2023, now Pat. No. 11,807,637.

(30) Foreign Application Priority Data

Jun. 21, 2022 (KR) .................. 10-2022-0075726
Feb. 13, 2023 (KR) .................. 10-2023-0018717

(51) Int. Cl.
*A61K 31/428* (2006.01)
*A61K 31/4535* (2006.01)
*A61P 1/00* (2006.01)
*C07D 417/12* (2006.01)
*C07D 417/14* (2006.01)

(52) U.S. Cl.
CPC .............. *C07D 417/12* (2013.01); *A61P 1/00* (2018.01); *C07D 417/14* (2013.01)

(58) Field of Classification Search
CPC .............. A61K 31/428; A61K 31/4535; A61K 31/496; A61K 31/5377; A61P 35/00; A61P 37/00
USPC .................. 514/367, 321, 254.02, 233.8
See application file for complete search history.

(56) References Cited

U.S. PATENT DOCUMENTS 11,807,637 B1 * 11/2023 Seo ........................... A61P 1/00

FOREIGN PATENT DOCUMENTS

KR 10-2022-0137555 A 10/2022

OTHER PUBLICATIONS

Gardner, C. R. et al.: Synthesis of retinoid enhancers based on 2-aminobenzothiazoles for anti-cancer therapy. Bioorganic & Med. Chem., vol. 20, pp. 6877-6884, 2012.*

* cited by examiner

*Primary Examiner* — Charanjit Aulakh
(74) *Attorney, Agent, or Firm* — PLEECHAE IP, LLC

(57) ABSTRACT

A compound represented by Formula 1, a stereoisomer thereof or a pharmaceutically acceptable salt thereof may be used for treating or preventing an autoimmune disease or a cancer. The autoimmune disease may be any one selected from the group consisting of inflammatory bowel disease, multiple sclerosis, graft-versus-host disease, asthma, atopy, psoriasis, rheumatoid arthritis, systemic lupus erythematous and type 1 diabetes. The cancer may be selected from the group consisting of colon cancer, melanoma, liver cancer, gliocytoma, ovarian cancer, colorectal cancer, head and neck cancer, bladder cancer, kidney cell cancer, stomach cancer, breast cancer, metastatic cancer, prostate cancer, gallbladder cancer, pancreatic cancer, blood cancer, skin cancer and lung cancer.

8 Claims, 16 Drawing Sheets

Specification includes a Sequence Listing.

SEQUENCE LISTING

```
Sequence total quantity: 28
SEQ ID NO: 1           moltype = DNA  length = 23
FEATURE                Location/Qualifiers
source                 1..23
                       mol_type = other DNA
                       organism = synthetic construct
SEQUENCE: 1
caccctcatc agtaatggtc aga                                             23

SEQ ID NO: 2           moltype = DNA  length = 20
FEATURE                Location/Qualifiers
source                 1..20
                       mol_type = other DNA
                       organism = synthetic construct
SEQUENCE: 2
aacgtgctta tcaggacctc                                                 20

SEQ ID NO: 3           moltype = DNA  length = 20
FEATURE                Location/Qualifiers
source                 1..20
                       mol_type = other DNA
                       organism = synthetic construct
SEQUENCE: 3
tgatgacatc aagaaggtgg                                                 20

SEQ ID NO: 4           moltype = DNA  length = 20
FEATURE                Location/Qualifiers
source                 1..20
                       mol_type = other DNA
                       organism = synthetic construct
SEQUENCE: 4
ttactccttg gaggccatgt                                                 20

SEQ ID NO: 5           moltype = DNA  length = 22
FEATURE                Location/Qualifiers
source                 1..22
                       mol_type = other DNA
                       organism = synthetic construct
SEQUENCE: 5
gatggctgaa aaagatggat gc                                              22

SEQ ID NO: 6           moltype = DNA  length = 20
FEATURE                Location/Qualifiers
source                 1..20
                       mol_type = other DNA
                       organism = synthetic construct
SEQUENCE: 6
```

```
tggttgggtc aggggtggtt                                               20

SEQ ID NO: 7              moltype = DNA   length = 21
FEATURE                   Location/Qualifiers
source                    1..21
                          mol_type = other DNA
                          organism = synthetic construct
SEQUENCE: 7
ctcgtgctgt cggacccata t                                             21

SEQ ID NO: 8              moltype = DNA   length = 22
FEATURE                   Location/Qualifiers
source                    1..22
                          mol_type = other DNA
                          organism = synthetic construct
SEQUENCE: 8
ttgaagacaa accgcttttc ca                                            22

SEQ ID NO: 9              moltype = DNA   length = 22
FEATURE                   Location/Qualifiers
source                    1..22
                          mol_type = other DNA
                          organism = synthetic construct
SEQUENCE: 9
catgttctct gcgaaatcgt gg                                            22

SEQ ID NO: 10             moltype = DNA   length = 22
FEATURE                   Location/Qualifiers
source                    1..22
                          mol_type = other DNA
                          organism = synthetic construct
SEQUENCE: 10
aacgcactag gtttgccgag ta                                            22

SEQ ID NO: 11             moltype = DNA   length = 21
FEATURE                   Location/Qualifiers
source                    1..21
                          mol_type = other DNA
                          organism = synthetic construct
SEQUENCE: 11
tttaactccc ttggcgcaaa a                                             21

SEQ ID NO: 12             moltype = DNA   length = 20
FEATURE                   Location/Qualifiers
source                    1..20
                          mol_type = other DNA
                          organism = synthetic construct
SEQUENCE: 12
ctttccctcc gcattgacac                                               20

SEQ ID NO: 13             moltype = DNA   length = 20
FEATURE                   Location/Qualifiers
source                    1..20
                          mol_type = other DNA
                          organism = synthetic construct
SEQUENCE: 13
ccacaccgtc agccgatttg                                               20

SEQ ID NO: 14             moltype = DNA   length = 21
FEATURE                   Location/Qualifiers
source                    1..21
                          mol_type = other DNA
                          organism = synthetic construct
SEQUENCE: 14
cacccattcc cttcacagag c                                             21

SEQ ID NO: 15             moltype = DNA   length = 22
FEATURE                   Location/Qualifiers
source                    1..22
                          mol_type = other DNA
                          organism = synthetic construct
SEQUENCE: 15
aaatcaccat gccctctaca ag                                            22

SEQ ID NO: 16             moltype = DNA   length = 22
FEATURE                   Location/Qualifiers
source                    1..22
                          mol_type = other DNA
                          organism = synthetic construct
```

```
SEQUENCE: 16
cccacttta tcaccatcgc aa                                             22

SEQ ID NO: 17           moltype = DNA   length = 23
FEATURE                 Location/Qualifiers
source                  1..23
                        mol_type = other DNA
                        organism = synthetic construct
SEQUENCE: 17
atactctagg aaggaaggac acc                                           23

SEQ ID NO: 18           moltype = DNA   length = 23
FEATURE                 Location/Qualifiers
source                  1..23
                        mol_type = other DNA
                        organism = synthetic construct
SEQUENCE: 18
tccatgatgt catttatgag ggc                                           23

SEQ ID NO: 19           moltype = DNA   length = 21
FEATURE                 Location/Qualifiers
source                  1..21
                        mol_type = other DNA
                        organism = synthetic construct
SEQUENCE: 19
caaggcagtg gagcaggtga a                                             21

SEQ ID NO: 20           moltype = DNA   length = 23
FEATURE                 Location/Qualifiers
source                  1..23
                        mol_type = other DNA
                        organism = synthetic construct
SEQUENCE: 20
cggagagagg tacaaacgag gtt                                           23

SEQ ID NO: 21           moltype = DNA   length = 19
FEATURE                 Location/Qualifiers
source                  1..19
                        mol_type = other DNA
                        organism = synthetic construct
SEQUENCE: 21
cccatcccca ggagtcttg                                                19

SEQ ID NO: 22           moltype = DNA   length = 21
FEATURE                 Location/Qualifiers
source                  1..21
                        mol_type = other DNA
                        organism = synthetic construct
SEQUENCE: 22
accatgacta ggggcactgt a                                             21

SEQ ID NO: 23           moltype = DNA   length = 23
FEATURE                 Location/Qualifiers
source                  1..23
                        mol_type = other DNA
                        organism = synthetic construct
SEQUENCE: 23
actccctgaa gaatataccc tcc                                           23

SEQ ID NO: 24           moltype = DNA   length = 22
FEATURE                 Location/Qualifiers
source                  1..22
                        mol_type = other DNA
                        organism = synthetic construct
SEQUENCE: 24
cgctattgag cacagatacg ag                                            22
```

```
SEQ ID NO: 25          moltype = DNA   length = 20
FEATURE                Location/Qualifiers
source                 1..20
                       mol_type = other DNA
                       organism = synthetic construct
SEQUENCE: 25
atgcccacct cctcaaagac                                              20

SEQ ID NO: 26          moltype = DNA   length = 23
FEATURE                Location/Qualifiers
source                 1..23
                       mol_type = other DNA
                       organism = synthetic construct
SEQUENCE: 26
gtagtttccg ttggaacagt gaa                                          23

SEQ ID NO: 27          moltype = DNA   length = 20
FEATURE                Location/Qualifiers
source                 1..20
                       mol_type = other DNA
                       organism = synthetic construct
SEQUENCE: 27
ttcaccacca tggagaaggc                                              20

SEQ ID NO: 28          moltype = DNA   length = 20
FEATURE                Location/Qualifiers
source                 1..20
                       mol_type = other DNA
                       organism = synthetic construct
SEQUENCE: 28
ggcatggact gtggtcatga                                              20
```

COMPOUND AND USE THEREOF IN TREATING AUTOIMMUNE DISEASES

CROSS-REFERENCE TO RELATED APPLICATION AND CLAIM OF PRIORITY

The present application is a continuation of U.S. patent application Ser. No. 18/138,817, filed Apr. 25, 2023, which claims priority to the benefit of Korean Patent Application Nos. 10-2022-0075726 filed on Jun. 21, 2022 and 10-2023-0018717 filed on Feb. 13, 2023 in the Korean Intellectual Property Office, the entire disclosure of which is incorporated herein by reference for all purposes.

BACKGROUND

1. Field of the Invention

The present invention relates to a novel compound and use thereof for treatment of autoimmune diseases.

2. Description of the Related Art

The human body can be protected from pathogens through immune response. Biological defense mechanisms against foreign microorganisms such as viruses and bacteria are normally divided into innate immunity and adaptive immunity, which are mediated by cytokines mostly secreted from immune-related cells.

The immune system serves to protect the body from antigens, that is, harmful foreign substances. Types of these antigens include bacteria, viruses, toxins, cancer cells, and blood and tissues from other humans or animals. The immune system produces antibodies and cytokines to destroy these harmful substances. If there are autoimmune disorders, the immune system cannot distinguish between its body organs and harmful antigens, and may destroy normal tissues. Diseases derived through such a response as described above refer to an autoimmune disease.

Aryl hydrocarbon receptor (AHR) is a ligand-dependent transcription factor belonging to PER-ARNT-SIM (PAS) superfamily, and is mainly expressed in immune cells, epithelial cells, endothelial cells, and stromal cells of barrier tissues. AHR is an environmental sensor and detects not only xenobiotic ligands such as environmental pollutants (e.g., dioxins), but also physiological ligands generated from cells, microorganisms, and food.

The inactivated form of AHR forms a complex with Hsp90:XAP2:p23:Src chaperone (AHR chaperone complex) in the cytoplasm, and maintains a structure with high affinity for ligand. When AHR is activated after ligand binding, the complex moves to the nucleus and the AHR is separated from a chaperone complex and binds to AHR-responsive DNA elements (xenobiotic response elements, XREs) located in the upstream regulatory regions of a target gene to regulate the expression of the target gene. Non-toxic immunomodulatory ligands that can activate AHR in vivo may be developed as a new therapeutic agent for autoimmune diseases.

SUMMARY

An aspect of the present invention is to provide a novel compound, a stereoisomer or a pharmaceutically acceptable salt thereof.

In addition, another aspect of the present invention is to provide a novel compound useful for prevention and treatment of autoimmune diseases, a stereoisomer or a pharmaceutically acceptable salt thereof.

Further, another aspect of the present invention is to provide a pharmaceutical composition for prevention or treatment of autoimmune diseases, including a novel compound, a stereoisomer or a pharmaceutically acceptable salt thereof.

To achieve the above aspects, the following technical solutions are adopted in the present invention.

1. A compound represented by Formula 1 below, a stereoisomer thereof or a pharmaceutically acceptable salt thereof:

[Formula 1]

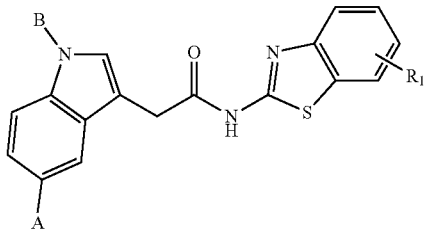

(wherein, A is hydrogen, halogen, a hydroxyl group, a $C_1$-$C_3$ alkyl group, a $C_2$-$C_3$ alkenyl group, a $C_2$-$C_3$ alkynyl group, a $C_1$-$C_3$ alkoxy group, dimethylamine, —$NO_2$, —CN, —$COOR_2$ or —$S(=O)_2R_2$, B is hydrogen, a $C_1$-$C_3$ alkyl group, a phenyl group, an acetyl group, —$CH_2C(=O)OR_2$, —$C(=O)OR_2$ or —$S(=O)_2R_2$, $R_1$ is a substituted or unsubstituted 5-7 membered heterocyclic ring or —$NH_2$, and $R_2$ is a $C_1$-$C_3$ alkyl group).

2. The compound, the stereoisomer or the pharmaceutically acceptable salt thereof according to the above 1, wherein the substituted 5-7 membered heterocyclic ring is a 5-7 membered heterocyclic ring substituted with a $C_1$-$C_3$ alkyl group, a hydroxyl group or dimethylamine.

3. The compound, the stereoisomer or the pharmaceutically acceptable salt thereof according to the above 1, wherein the substituted or unsubstituted 5-7 membered heterocyclic ring is any one selected from the group consisting of the following heterocyclic rings:

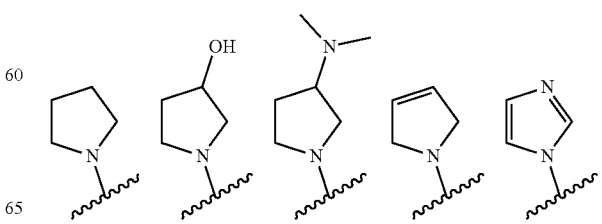

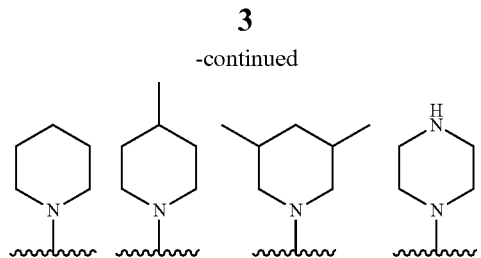
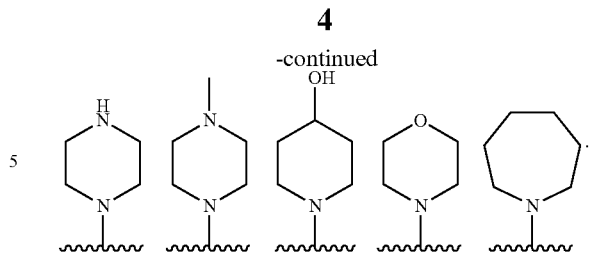
4. The compound, the stereoisomer or the pharmaceutically acceptable salt thereof according to the above 1, wherein the compound represented by Formula 1 is any one selected from the group consisting of the following compounds.
| Compound | Structure |
|---|---|
| 1 | ![structure 1] |
| 2 | ![structure 2] |
| 3 | ![structure 3] |
| 4 | ![structure 4] |

-continued
| Compound | Structure |
|---|---|
| 5 | 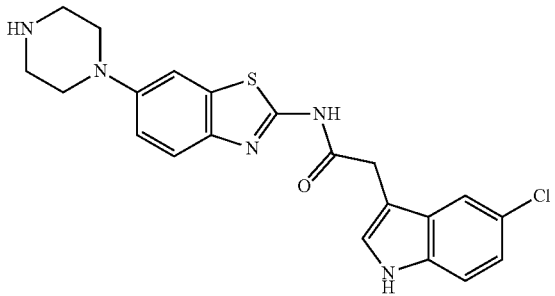 [SMILES: O=C(Cc1c[nH]c2ccc(Cl)cc12)Nc1nc2ccc(N3CCNCC3)cc2s1] |
| 6 | 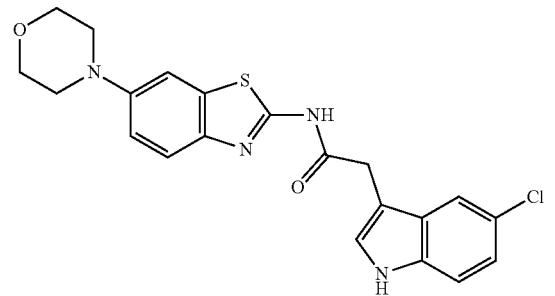 [SMILES: O=C(Cc1c[nH]c2ccc(Cl)cc12)Nc1nc2ccc(N3CCOCC3)cc2s1] |
| 7 | 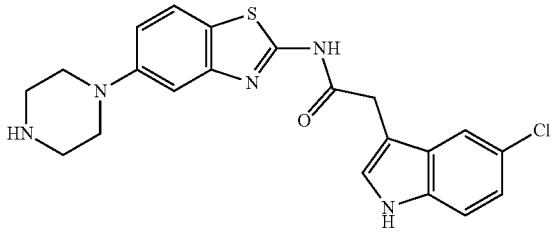 [SMILES: O=C(Cc1c[nH]c2ccc(Cl)cc12)Nc1nc2cc(N3CCNCC3)ccc2s1] |
| 8 | 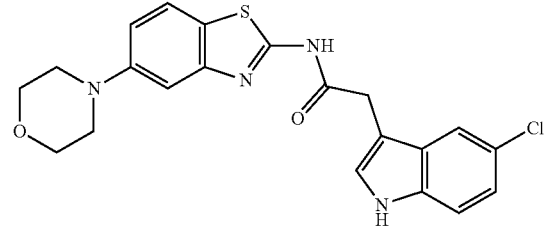 [SMILES: O=C(Cc1c[nH]c2ccc(Cl)cc12)Nc1nc2cc(N3CCOCC3)ccc2s1] |
| 9 | 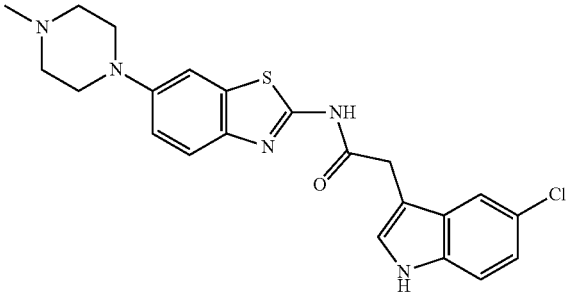 [SMILES: CC1CCN(c2ccc3nc(NC(=O)Cc4c[nH]c5ccc(Cl)cc45)sc3c2)CC1] |

-continued

| Compound | Structure |
|---|---|
| 10 | 2-(5-chloro-1H-indol-3-yl)-N-(6-(pyrrolidin-1-yl)benzo[d]thiazol-2-yl)acetamide |
| 11 | 2-(5-chloro-1H-indol-3-yl)-N-(6-(2,5-dihydro-1H-pyrrol-1-yl)benzo[d]thiazol-2-yl)acetamide |
| 12 | 2-(5-chloro-1H-indol-3-yl)-N-(6-(1H-imidazol-1-yl)benzo[d]thiazol-2-yl)acetamide |
| 13 | 2-(5-chloro-1H-indol-3-yl)-N-(6-(3-hydroxypyrrolidin-1-yl)benzo[d]thiazol-2-yl)acetamide |
| 14 | 2-(5-chloro-1H-indol-3-yl)-N-(6-(piperidin-1-yl)benzo[d]thiazol-2-yl)acetamide |

-continued

| Compound | Structure |
|---|---|
| 16 | ![Structure of compound 16: 4-methylpiperidinyl-benzothiazole-NH-C(O)-CH2-(5-chloroindole)] |
| 17 | ![Structure of compound 17: 4-hydroxypiperidinyl-benzothiazole-NH-C(O)-CH2-(5-chloroindole)] |
| 18 | ![Structure of compound 18: azepanyl-benzothiazole-NH-C(O)-CH2-(5-chloroindole)] |
| 19 | ![Structure of compound 19: 3-(dimethylamino)pyrrolidinyl-benzothiazole-NH-C(O)-CH2-(5-chloroindole)] |

-continued
| Compound | Structure |
|---|---|
| 20 | 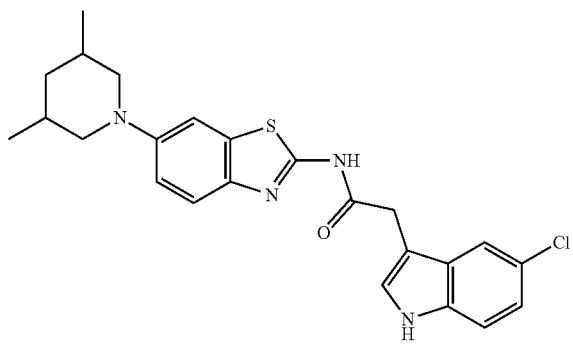 [SMILES: CC1CC(C)CN(c2ccc3nc(NC(=O)Cc4c[nH]c5ccc(Cl)cc45)sc3c2)C1] |
| 21 | 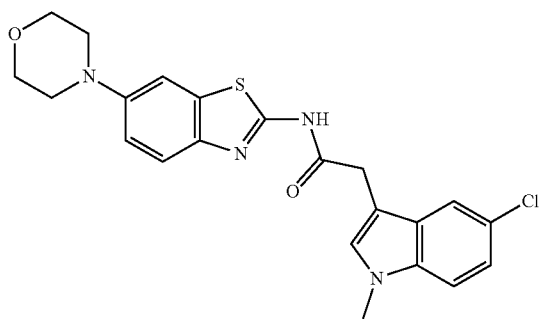 [SMILES: Cn1cc(CC(=O)Nc2nc3ccc(N4CCOCC4)cc3s2)c2cc(Cl)ccc21] |
| 22 | 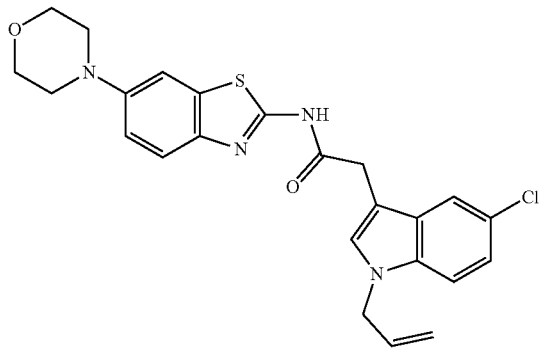 [SMILES: C=CCn1cc(CC(=O)Nc2nc3ccc(N4CCOCC4)cc3s2)c2cc(Cl)ccc21] |
| 23 | 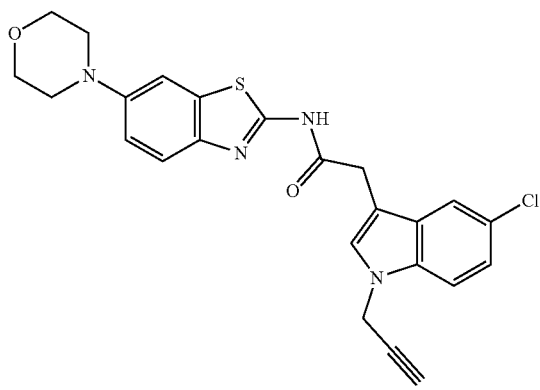 [SMILES: C#CCn1cc(CC(=O)Nc2nc3ccc(N4CCOCC4)cc3s2)c2cc(Cl)ccc21] |

-continued

| Compound | Structure |
|---|---|
| 24 | 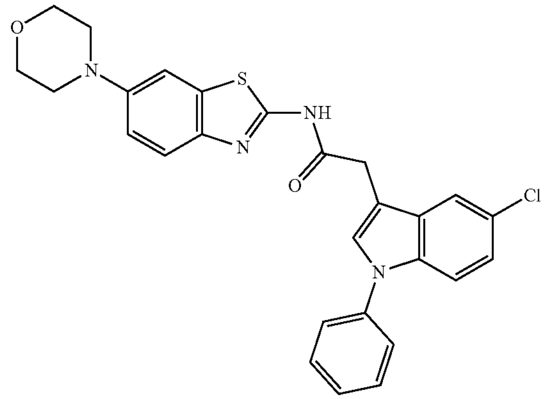 [SMILES: O=C(Cc1cn(-c2ccccc2)c2ccc(Cl)cc12)Nc1nc2ccc(N3CCOCC3)cc2s1] |
| 25 | 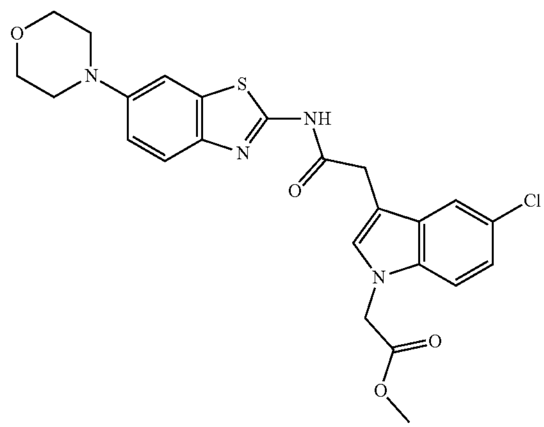 [SMILES: COC(=O)Cn1cc(CC(=O)Nc2nc3ccc(N4CCOCC4)cc3s2)c2cc(Cl)ccc21] |
| 26 | 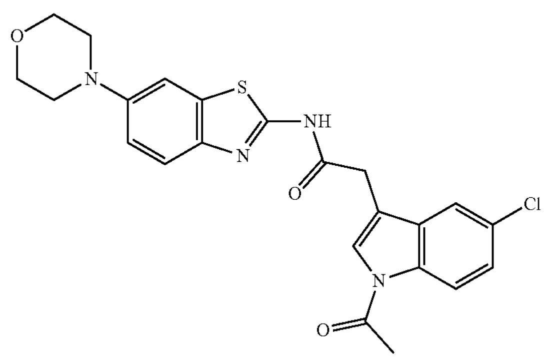 [SMILES: CC(=O)n1cc(CC(=O)Nc2nc3ccc(N4CCOCC4)cc3s2)c2cc(Cl)ccc21] |
| 27 | 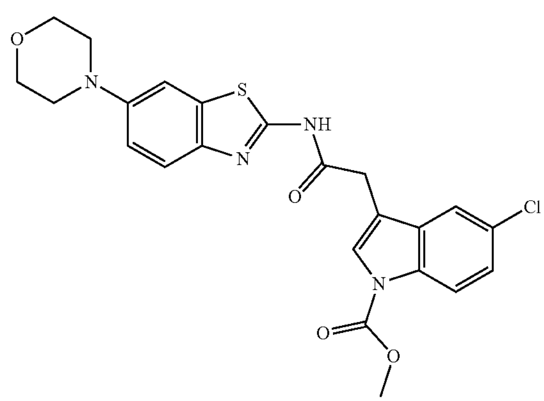 [SMILES: COC(=O)n1cc(CC(=O)Nc2nc3ccc(N4CCOCC4)cc3s2)c2cc(Cl)ccc21] |

-continued

| Compound | Structure |
|---|---|
| 28 | 6-morpholino-benzothiazol-2-yl amide of 2-(5-chloro-1-(methylsulfonyl)-1H-indol-3-yl)acetic acid |
| 29 | 6-morpholino-benzothiazol-2-yl amide of 2-(1H-indol-3-yl)acetic acid |
| 30 | 6-morpholino-benzothiazol-2-yl amide of 2-(5-methyl-1H-indol-3-yl)acetic acid |
| 31 | 6-morpholino-benzothiazol-2-yl amide of 2-(5-fluoro-1H-indol-3-yl)acetic acid |
| 32 | 6-morpholino-benzothiazol-2-yl amide of 2-(5-hydroxy-1H-indol-3-yl)acetic acid |

-continued
| Compound | Structure |
|---|---|
| 33 | 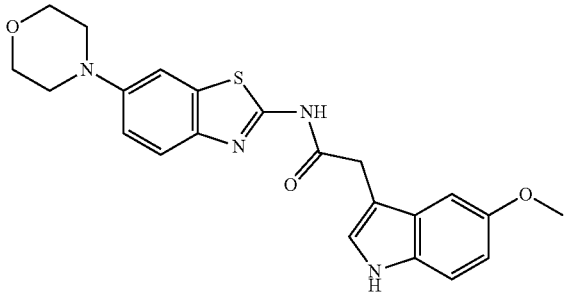 [SMILES: COc1ccc2[nH]cc(CC(=O)Nc3nc4ccc(N5CCOCC5)cc4s3)c2c1] |
| 34 | 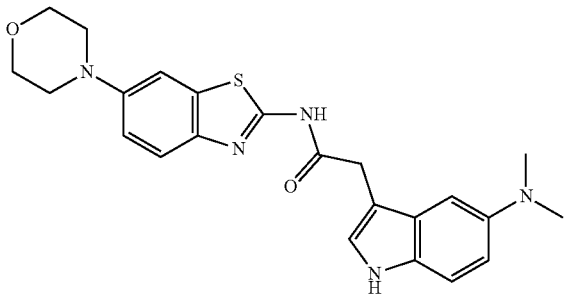 [SMILES: CN(C)c1ccc2[nH]cc(CC(=O)Nc3nc4ccc(N5CCOCC5)cc4s3)c2c1] |
| 35 | 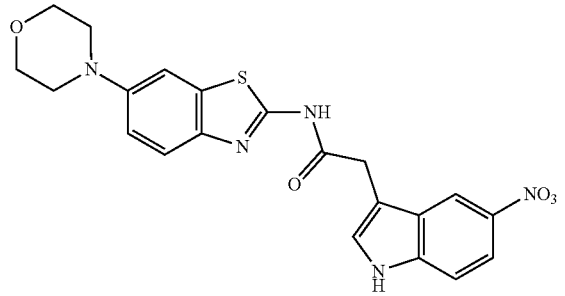 |
| 36 | 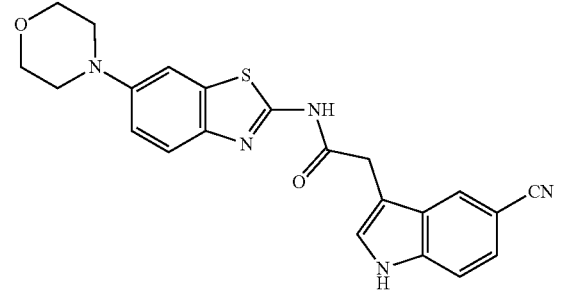 [SMILES: N#Cc1ccc2[nH]cc(CC(=O)Nc3nc4ccc(N5CCOCC5)cc4s3)c2c1] |
| 37 | 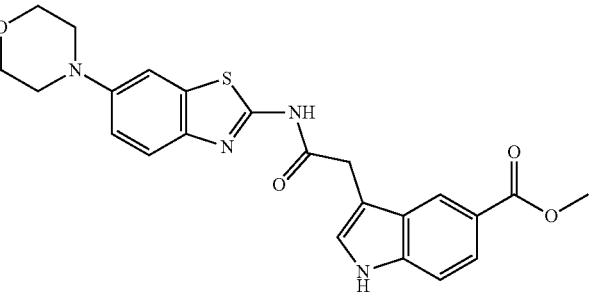 |

-continued

| Compound | Structure |
|---|---|
| 38 | 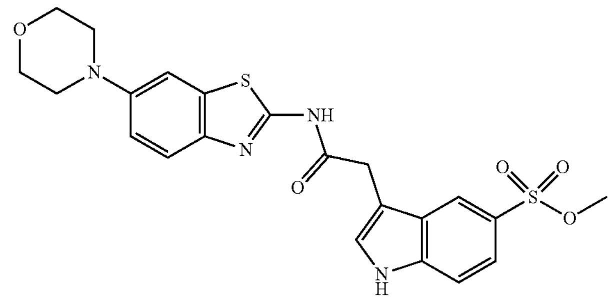 [SMILES: COS(=O)(=O)c1ccc2[nH]cc(CC(=O)Nc3nc4ccc(N5CCOCC5)cc4s3)c2c1] |
| 39 | 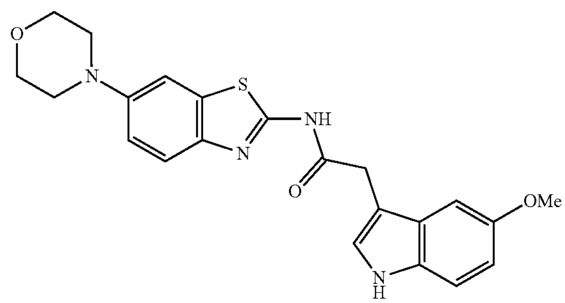 [SMILES: COc1ccc2[nH]cc(CC(=O)Nc3nc4ccc(N5CCOCC5)cc4s3)c2c1] |

5. A pharmaceutical composition, including the compound, the stereoisomer or the pharmaceutically acceptable salt thereof according to any one of the above 1 to 4.

6. The pharmaceutical composition according to the above 5, wherein the composition is used for treating or preventing autoimmune diseases.

7. The pharmaceutical composition according to the above 5, wherein the autoimmune disease is any one selected from the group consisting of inflammatory bowel disease, multiple sclerosis, graft-versus-host disease, asthma, atopy, psoriasis, rheumatoid arthritis, systemic lupus erythematous and type 1 diabetes.

8. The pharmaceutical composition according to the above 5, wherein the composition is used for treating or preventing cancer.

9. The pharmaceutical composition according to the above 8, wherein the cancer is selected from the group consisting of colon cancer, melanoma, liver cancer, gliocytoma, ovarian cancer, colorectal cancer, head and neck cancer, bladder cancer, kidney cell cancer, stomach cancer, breast cancer, metastatic cancer, prostate cancer, gallbladder cancer, pancreatic cancer, blood cancer, skin cancer and lung cancer.

10. A method for treatment of autoimmune diseases, including administering the compound according to any one of the above 1 to 4 to a subject in need thereof.

11. A method for treatment of a cancer, including administering the compound according to any one of the above 1 to 4 to a subject in need thereof.

The novel compound, the stereoisomer or the pharmaceutically acceptable salt thereof according to an embodiment of the present invention may induce activity of AHR as an immunomodulatory transcription factor, thereby attaining effects of not only controlling inflammation but also restoring immune balance and damaged tissues.

The novel compound, the stereoisomer or the pharmaceutically acceptable salt thereof according to an embodiment of the present invention may inhibit production of IL-6 as an inflammatory factor, thereby attaining effects of regulating excessive immune response, in particular, autoimmune response.

The novel compound, the stereoisomer or the pharmaceutically acceptable salt thereof according to an embodiment of the present invention may exhibit effects of inducing activity of a regulatory T cell (Treg).

Further, the novel compound, the stereoisomer or the pharmaceutically acceptable salt thereof according to an embodiment of the present invention may exhibit effects of preventing and treating autoimmune diseases by regulating the above inflammatory factors.

BRIEF DESCRIPTION OF THE DRAWINGS

FIGS. 5 and 6 illustrate inflammatory bowel disease therapeutic effects of the compound of an embodiment of the present invention in an animal model with dextran sodium sulfate (DSS)-induced inflammatory bowel disease. Specifically, FIG. 5 demonstrates that the lower the severity index (Disease Activity Index), the more the treatment is completed, than the control (vehicle), while FIG. 6 shows that the smaller the weight of the colon as compared to the length thereof, the higher the therapeutic effects of inflammatory bowel disease are.

DETAILED DESCRIPTION

Figure 1:
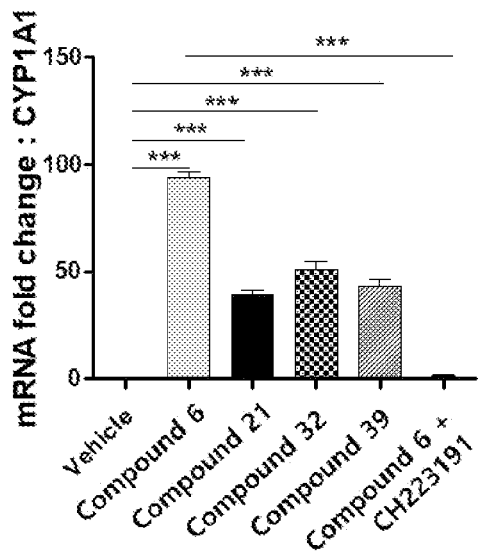
FIGS. 1 and 2 illustrate measurement of AHR-target gene CYP1A1 expression level in order to confirm AHR ligand under cell culture conditions of a compound of an embodiment of the present invention.

Hereinafter, exemplary embodiments of the present invention will be described in detail.

All technical terms used in the present invention are used in the same meaning as those skilled in the art may generally understand in the related field of the present invention unless otherwise defined. Further, although preferred methods or samples will be described in the present specification, those similar or equivalent are also included in the scope of the present invention.

In the formula (structural formula) of the present invention, if any substituent is not indicated in a site although the site needs a substituent, it means that a hydrogen substituent is omitted, which would be applied to all formulae (structural formulae) in the present invention.

An embodiment of the present invention relates to a compound represented by Formula 1 below, a stereoisomer or a pharmaceutically acceptable salt thereof:

[Formula 1]

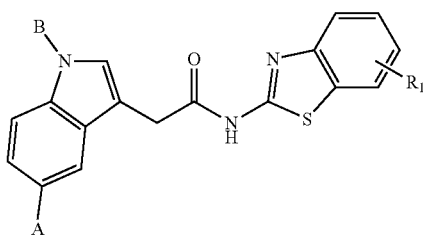

In the above Formula 1, A is hydrogen, halogen, a hydroxyl group, a $C_1$-$C_3$ alkyl group, a $C_2$-$C_3$ alkenyl group, a $C_2$-$C_3$ alkynyl group, a $C_1$-$C_3$ alkoxy group, dimethylamine, —$NO_2$, —CN, —$COOR_2$ or —$S(=O)_2R_2$, B is hydrogen, a $C_1$-$C_3$ alkyl group, a phenyl group, an acetyl group, —$CH_2C(=O)OR_2$, —$C(=O)OR_2$ or —$S(=O)_2R_2$, $R_1$ is a substituted or unsubstituted 5-7 membered heterocyclic ring or —$NH_2$, and $R_2$ is a $C_1$-$C_3$ alkyl group.

$R_1$ is substituted on any one of benzene ring carbon atoms of benzothiazole.

The 5-7 membered heterocyclic ring may be a compound in which 1 to 2 carbon atoms in the ring are substituted with nitrogen or oxygen atoms.

The substituted 5-7 membered heterocyclic ring may be a compound having a 5-7 membered heterocyclic ring substituted with a $C_1$-$C_3$ alkyl group, a hydroxyl group or dimethylamine.

The substituted or unsubstituted 5-7 membered heterocyclic ring may be any one selected from the group consisting of the following heterocyclic rings:

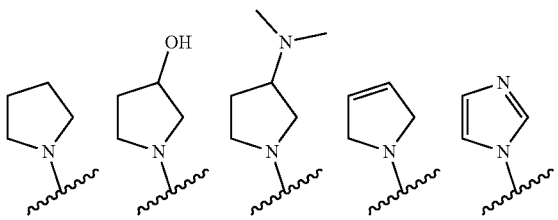

-continued
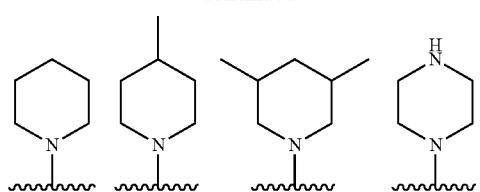
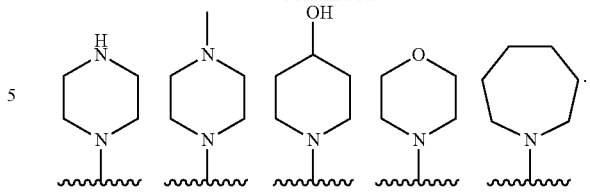
The compound represented by Formula 1 above may be any one selected from the group consisting of compounds listed in Table 1 below:
TABLE 1
| Compound | Structure |
| --- | --- |
| 1 | ![Structure 1] |
| 2 | ![Structure 2] |
| 3 | ![Structure 3] |
| 4 | ![Structure 4] |

TABLE 1-continued
| Compound | Structure |
|---|---|
| 5 | 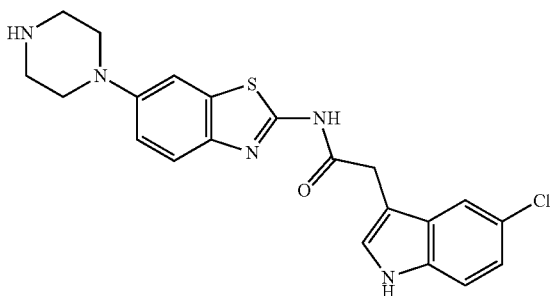 |
| 6 | 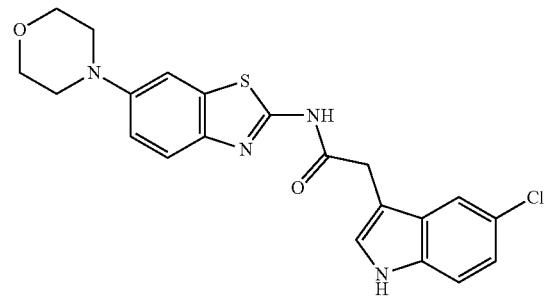 [SMILES: O=C(Cc1c[nH]c2ccc(Cl)cc12)Nc1nc2ccc(N3CCOCC3)cc2s1] |
| 7 | 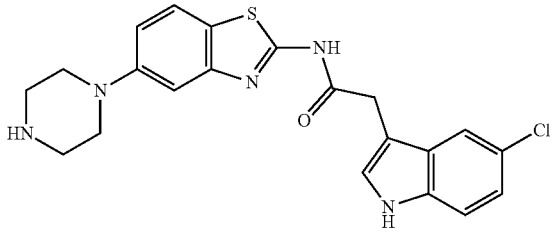 [SMILES: O=C(Cc1c[nH]c2ccc(Cl)cc12)Nc1nc2cc(N3CCNCC3)ccc2s1] |
| 8 | 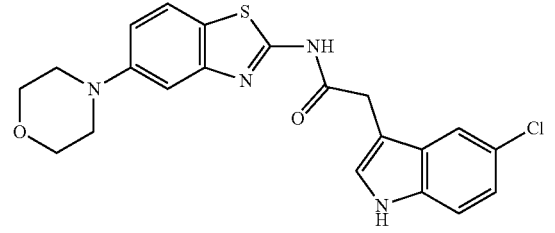 [SMILES: O=C(Cc1c[nH]c2ccc(Cl)cc12)Nc1nc2cc(N3CCOCC3)ccc2s1] |
| 9 | 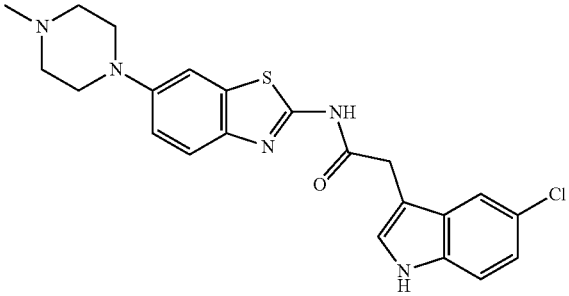 |

TABLE 1-continued

| Compound | Structure |
|---|---|
| 10 | (6-pyrrolidin-1-yl-benzothiazol-2-yl) amide of 2-(5-chloro-1H-indol-3-yl)acetic acid |
| 11 | (6-(2,5-dihydro-1H-pyrrol-1-yl)-benzothiazol-2-yl) amide of 2-(5-chloro-1H-indol-3-yl)acetic acid |
| 12 | (6-imidazol-1-yl-benzothiazol-2-yl) amide of 2-(5-chloro-1H-indol-3-yl)acetic acid |
| 13 | (6-(3-hydroxypyrrolidin-1-yl)-benzothiazol-2-yl) amide of 2-(5-chloro-1H-indol-3-yl)acetic acid |
| 14 | (6-piperidin-1-yl-benzothiazol-2-yl) amide of 2-(5-chloro-1H-indol-3-yl)acetic acid |

TABLE 1-continued

| Compound | Structure |
|---|---|
| 16 | (4-methylpiperidin-1-yl)-benzothiazol-2-yl-NH-C(O)-CH2-(5-chloro-1H-indol-3-yl) |
| 17 | (4-hydroxypiperidin-1-yl)-benzothiazol-2-yl-NH-C(O)-CH2-(5-chloro-1H-indol-3-yl) |
| 18 | (azepan-1-yl)-benzothiazol-2-yl-NH-C(O)-CH2-(5-chloro-1H-indol-3-yl) |
| 19 | (3-(dimethylamino)pyrrolidin-1-yl)-benzothiazol-2-yl-NH-C(O)-CH2-(5-chloro-1H-indol-3-yl) |

TABLE 1-continued

| Compound | Structure |
|---|---|
| 20 | 3,5-dimethylpiperidin-1-yl-benzothiazol-2-yl-NH-C(O)-CH₂-(5-chloro-1H-indol-3-yl) |
| 21 | morpholin-4-yl-benzothiazol-2-yl-NH-C(O)-CH₂-(5-chloro-1-methyl-indol-3-yl) |
| 22 | morpholin-4-yl-benzothiazol-2-yl-NH-C(O)-CH₂-(5-chloro-1-allyl-indol-3-yl) |
| 23 | morpholin-4-yl-benzothiazol-2-yl-NH-C(O)-CH₂-(5-chloro-1-propargyl-indol-3-yl) |

TABLE 1-continued

| Compound | Structure |
|---|---|
| 24 | *[structure: 6-morpholinobenzothiazol-2-yl amide of 2-(5-chloro-1-phenyl-1H-indol-3-yl)acetic acid]* |
| 25 | *[structure: 6-morpholinobenzothiazol-2-yl amide of 2-(5-chloro-1H-indol-3-yl)acetic acid with N-CH₂C(O)OCH₃ on indole]* |
| 26 | *[structure: 6-morpholinobenzothiazol-2-yl amide of 2-(5-chloro-1-acetyl-1H-indol-3-yl)acetic acid]* |
| 27 | *[structure: 6-morpholinobenzothiazol-2-yl amide of 2-(5-chloro-1H-indol-3-yl)acetic acid with N-C(O)OCH₃ on indole]* |

TABLE 1-continued

| Compound | Structure |
|---|---|
| 28 | 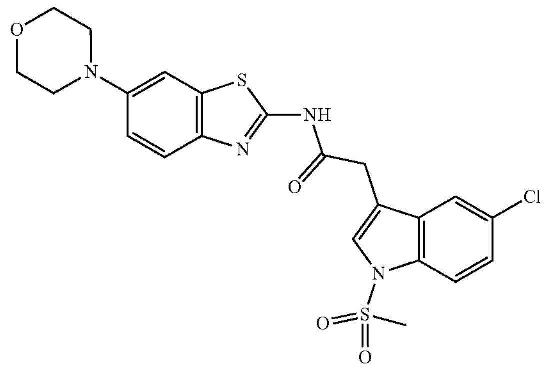 [SMILES: CS(=O)(=O)n1cc(CC(=O)Nc2nc3ccc(N4CCOCC4)cc3s2)c2cc(Cl)ccc21] |
| 29 | 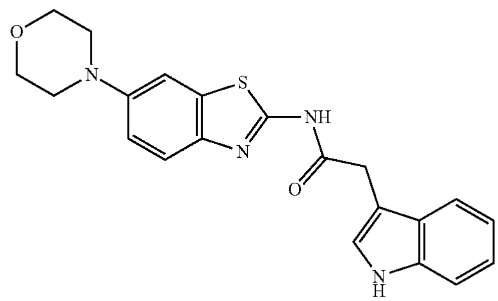 [SMILES: O=C(Cc1c[nH]c2ccccc12)Nc1nc2ccc(N3CCOCC3)cc2s1] |
| 30 | 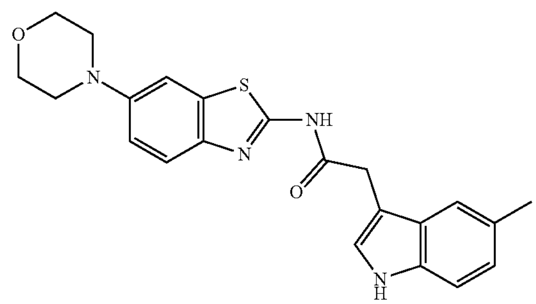 [SMILES: Cc1ccc2[nH]cc(CC(=O)Nc3nc4ccc(N5CCOCC5)cc4s3)c2c1] |
| 31 | 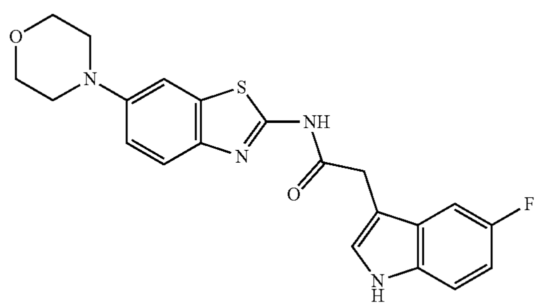 [SMILES: O=C(Cc1c[nH]c2ccc(F)cc12)Nc1nc2ccc(N3CCOCC3)cc2s1] |
| 32 | 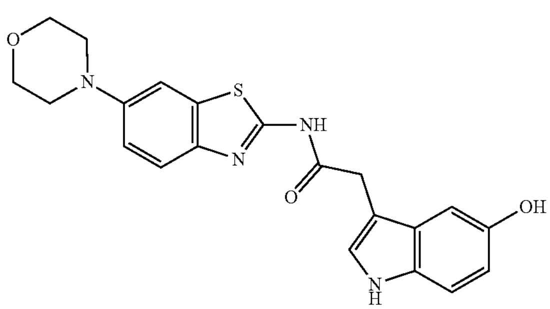 [SMILES: O=C(Cc1c[nH]c2ccc(O)cc12)Nc1nc2ccc(N3CCOCC3)cc2s1] |

TABLE 1-continued
| Compound | Structure |
|---|---|
| 33 | 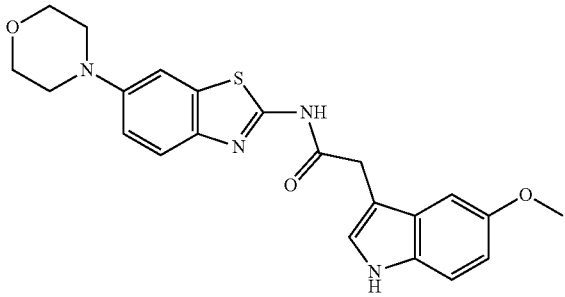 [SMILES: COc1ccc2[nH]cc(CC(=O)Nc3nc4ccc(N5CCOCC5)cc4s3)c2c1] |
| 34 | 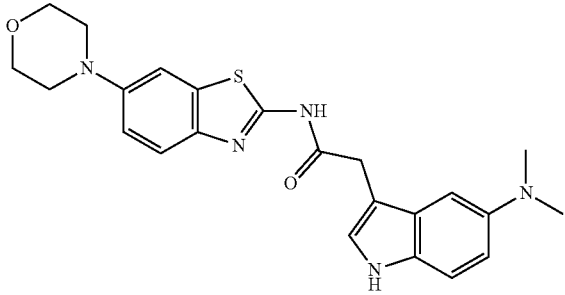 [SMILES: CN(C)c1ccc2[nH]cc(CC(=O)Nc3nc4ccc(N5CCOCC5)cc4s3)c2c1] |
| 35 | 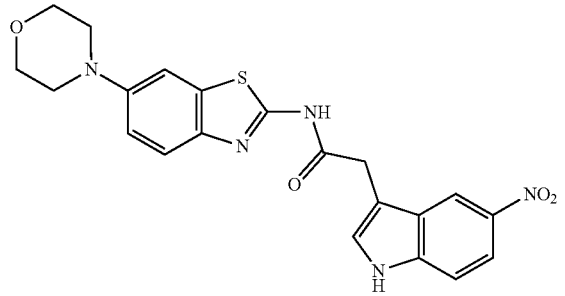 |
| 36 | 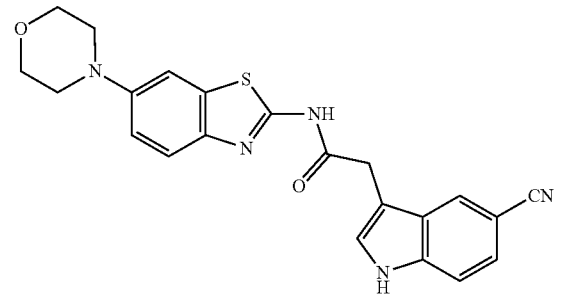 [SMILES: N#Cc1ccc2[nH]cc(CC(=O)Nc3nc4ccc(N5CCOCC5)cc4s3)c2c1] |
| 37 | 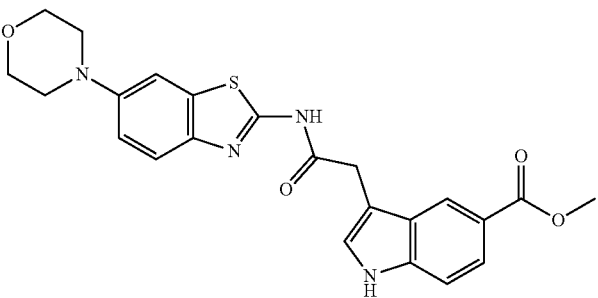 [SMILES: COC(=O)c1ccc2[nH]cc(CC(=O)Nc3nc4ccc(N5CCOCC5)cc4s3)c2c1] |

TABLE 1-continued

| Compound | Structure |
|---|---|
| 38 | *structure of 2-(5-(methoxysulfonyl)-1H-indol-3-yl)-N-(6-morpholinobenzo[d]thiazol-2-yl)acetamide* |
| 39 | *structure of 2-(5-methoxy-1H-indol-3-yl)-N-(6-morpholinobenzo[d]thiazol-2-yl)acetamide* |

The compound represented by Formula 1 may be any one selected from the group consisting of the following compounds:
2-(5-chloro-1H-indol-3-yl)-N-(6-morpholinobenzo[d]thiazol-2-yl)acetamide, Compound 6);
2-(5-chloro-1H-indol-3-yl)-N-(6-(4-methylpiperazine-1-yl)benzo[d]thiazol-2-yl)acetamide, Compound 9);
2-(5-chloro-1-methyl-1H-indol-3-yl)-N-(6-morpholinobenzo[d]thiazol-2-yl)acetamide, Compound 21);
2-(5-hydroxy-1H-indol-3-yl)-N-(6-morpholinobenzo[d]thiazol-2-yl)acetamide, Compound 32); and
2-(5-methoxy-1H-indol-3-yl)-N-(6-morpholinobenzo[d]thiazol-2-yl)acetamide, Compound 39).

Further, an embodiment of the present invention relates to a pharmaceutical composition which includes the above-described compound, the stereoisomer or the pharmaceutically acceptable salt thereof.

The pharmaceutical composition may be a pharmaceutical composition for treatment or prevention of autoimimine diseases. Specifically, the disease may be inflammatory bowel disease (IBD), multiple sclerosis (MS), graft-versus-host disease (GVHD), asthma, atopy, psoriasis, rheumatoid arthritis (RA), systemic lupus erythematous (SLE), type 1 diabetes mellitus (TID), Behcet's disease or Sjogren's syndrome. More specifically, the disease may be inflammatory bowel disease, multiple sclerosis, graft-versus-host disease, asthma, atopy, psoriasis, rheumatoid arthritis, systemic lupus erythematous, type 1 diabetes, but it is not limited thereto.

In an embodiment of the present invention, the "autoimmune disease" may cause damage to cells or tissues by humoral immunity, cellular immunity or both thereof. That is, the autoimmune disease is a disease in which an immune system causes improper reaction to autoantigen thus inducing autoimmune response systemically or specifically in specific organs, etc., which may cause chronic inflammation.

The "inflammatory bowel disease" refers to a disease in which abnormal chronic inflammation in the intestine repeats improvement and recurrence, and may correspond to one selected from the group consisting of Crohn's disease, ulcerative colitis and intestinal Bechet's disease, but it is not limited thereto.

The "multiple sclerosis" refers to an inflammatory disease inducing demyelination and scar formation as a sign and symptom in a broad sense, which is caused by damage and/or consumption of fatty myelin sheaths surrounding axons of the brain and spinal cord. Types of the multiple sclerosis may include recurrent palliative multiple sclerosis (RRMS), secondary progressive multiple sclerosis (SPMS), primary progressive multiple sclerosis (PPMS), and progressive recurrent multiple sclerosis (PRMS), but they are not limited thereto.

The "graft-versus-host disease" is a disease in which lymphocytes transfused during hematopoietic stem cell transplantation attack a host with deteriorated immune function to cause symptoms such as fever, rash, and abnormalities of liver function, etc., and may invade the skin, lungs, intestines, liver, or the like, but it is not limited thereto.

The "asthma" refers to a disease in which symptoms such as cough and breathing difficulty occur repeatedly due to inflammation of the bronchi when exposed to a specific causative agent, and may be caused by infection, smoking, allergens, etc., but it is not limited thereto.

The "atopy" refers to atonic dermatitis, and is a representative allergic disease in which symptoms such as itching and dry skin appear as a chronic recurrent inflammatory skin disease.

The "psoriasis" refers to an inflammatory disease that occurs in the skin or joints due to abnormality in the immune system, and may cause problems such as an occurrence of ugly appearance, increased keratin, or erythematous plaques, and accompanying pain. The psoriasis may include any one or more diseases selected from psoriatic arthritis, guttate psoriasis, pustular psoriasis, red skin psoriasis, scalp psoriasis, nail psoriasis and enthesitis.

The "rheumatoid arthritis" refers to a systemic autoimmune disease characterized by chronic inflammation of the joint site.

The "systemic lupus erythematous" is also called as "lupus," and refers to a systemic disease that invades various organs of the body, such as connective tissue, skin, joints, blood and kidneys, as a chronic inflammatory autoimmune disease. The exact cause is not known, but according to previous studies, it is known that genetic factors are associated with the occurrence of this disease. To help diagnose lupus, the American College of Rheumatology (ACR) has published 11 symptoms, signs, and test findings to help differentiate this disease from other diseases. According to the published study, if four or more among the 11 symptoms occur, it could be diagnosed as lupus.

The "type 1 diabetes" is an immune-mediated disease in which insulin-secreting beta cells are destroyed by an autoimmune reaction. The causes of this disease may include a number of genetic and environmental factors, which are specifically targeted to insulin-secreting beta cells. This disease may be accompanied by progressive inflammatory infiltration of the pancreatic islets by the immune cells.

In an embodiment of the present invention, the pharmaceutical composition may be prepared using a pharmaceutically suitable and physiologically acceptable additive in addition to the active ingredient, which is the compound of an embodiment of the present invention. The composition may be administered to a mammal. As the additive described above, for example, excipients, disintegrants, sweeteners, binders, coating agents, swelling agents, lubricants, glidants or flavoring agents may be used.

Further, the pharmaceutical composition of an embodiment of the present invention may be preferably formulated as a pharmaceutical composition that includes at least one pharmaceutically acceptable carrier in addition to the active ingredient in a pharmaceutically effective amount described above for administration.

The "pharmaceutically effective amount" means an amount sufficient to treat a disease with a reasonable benefit/risk ratio applicable to medical treatment, and an effective dose level may be determined based on a type and severity of patient's disease, drug activity, drug sensitivity, time of administration, route of administration and rate of excretion, duration of treatment, factors including drugs used concurrently, and other factors well known in the medical field. The pharmaceutical composition according to an embodiment of the present invention may be administered as an individual therapeutic agent or administered in combination with other therapeutic agents. Further, the composition may be administered sequentially or simultaneously with a conventional therapeutic agent, and may be administered in single or multiple doses. In consideration of all of the above factors, it is important to administer a minimum amount capable of attaining the maximum effect without side effects, such an amount could be easily determined by those skilled in the art.

Specifically, the effective amount of the pharmaceutical composition according to an embodiment of the present invention may vary depending on an age, sex, condition and/or body weight of the patient, absorption of the active ingredient in the body, inactivation rate and excretion rate, type of disease, and the drug to be used in combination. Typically, 0.001 to 1.50 mg, preferably 0.01 to 100 mg per 1 kg of body weight may be administered daily or every other day, or may be divided into 1 to 3 times a day. However, the dosage may be increased or decreased depending on the route of administration, severity of obesity, sex, body weight, age, etc., therefore, would not limit the scope of the present invention in any way.

Further, the "pharmaceutically acceptable" refers to a composition that is physiologically acceptable and does not usually cause allergic reactions such as gastrointestinal disorders and dizziness, or similar reactions when administered to humans.

Examples of the carrier, excipient and diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinylpyrrolidone, water, methyl hdroxybenzoate, propyl hydroxybenzoate, talc, magnesium stearate, and mineral oils. Further, fillers, anti-aggregating agents, lubricants, wetting agents, flavoring agents, emulsifying agents, and preservatives may additionally be included.

Further, the composition of an embodiment of the present invention may be formulated using any method known in the art in order to provide rapid, sustained or delayed release of the active ingredient after administration thereof to a subject in need of treatment using the pharmaceutical composition of an embodiment of the present invention including humans. The formulation may be powder, granule, tablet, emulsion syrup, aerosol, soft or hard gelatin capsule, sterile injectable solution, or sterile powder.

The expression "pharmaceutically acceptable salt" refers to a salt prepared using a specific compound according to the present invention, as well as acid or base relatively nontoxic thereto. The pharmaceutically acceptable salt may include, for example, acid addition salts or metal salts.

The acid addition salts may be formed from inorganic acids such as hydrochloric acid, nitric acid, phosphoric acid, sulfuric acid, hydrobromic acid, hydroiodic acid, nitrous or phosphorous acid, aliphatic mono and dicarboxylates, phenyl-substituted alkanoates, hydroxy alkanoates and alkane dioates, and non-toxic organic acids such as aromatic acids, aliphatic and aromatic sulfonic acids. These pharmaceutically non-toxic salts may include sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propyolate, oxalate, malonate, succinate, suberate, sebacate, fumarate, maleate, butine-1,4-dioate, nucleic acid-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, β_hydroxybutyrate, glycolate, malate, tartrate, methane sulfonate, propane sulfonate, naphthalene-1-sulfonate, naphthalene-2-sulfonate or mandelate.

The metal salt may be a sodium, potassium or calcium salt. The metal salt may be prepared using a base, for example, alkali-metal or alkaline earth metal salts may be obtained by dissolving the compound in an excess amount of alkali-metal hydroxide or alkaline earth metal hydroxide solution, filtering the non-dissolved compound salt, and evaporating or drying the filtrate.

An embodiment of the present invention may relate to a method for treatment if an autoimmune disease, which includes administering the compound, the stereoisomer or the phamiaceutically acceptable salt thereof to a subject in need thereof.

Further, an embodiment of the present invention may relate to a method for inducing activity of AHR, which includes administering the compound, the stereoisomer or the pharmaceutically acceptable salt thereof.

Specifically, the compounds of an embodiment of the present invention may target the aryl hydrocarbon receptor (AHR), which is an immunomodulatory transcription factor of an embodiment of the present invention, and may serve as an agent to induce AHR activity, thereby controlling inflammation, regulating immune balance, and repairing damaged tissue. Therefore, the compound may be used for therapeutic purposes of autoimmune diseases, but it is not limited thereto. Existing ligands are toxic, have low affinity and structural stability, and high target non-specificity, which entail a problem in that these are unsuitable for development into pharmaceutical compositions. On the other hand, when AHR activity is induced by the compound of an embodiment of the present invention having "drug-like properties," it could be effectively used for treatment and prevention of autoimmune diseases.

An embodiment of the present invention may relate to a method for inhibiting production of IL-6, which includes administering the compound, the stereoisomer or the pharmaceutically acceptable salt thereof.

Specifically, since the inflammatory factor IL-6 is known to cause autoimmune diseases, the compound of the present invention may be used in treatment of autoimmune diseases through a mechanism that inhibits the production thereof. Actually, there is a number of known therapeutic agents for autoimmune diseases that target inhibition of IL-6, as well as related papers. According to the following experimental data, the compound of an embodiment of the present invention is also confirmed to inhibit the production of IL-6 and thus is expected to have effects of reducing the autoimmune response, whereby the composition of an embodiment of the present invention may be used for treatment and prevention of autoimmune diseases.

Further, an embodiment of the present invention relates to a composition for prevention or treatment of a cancer, which includes the compound, the stereoisomer or the pharmaceutically acceptable salt thereof In the present invention, "cancer" broadly refers to uncontrolled abnormal growth of the host's own cells that invade the surrounding tissues of the initial abnormal cell growth site in the host and potential tissues located distally of these sites. Further, carcinoma as a cancer of epithelial tissues (e.g., the skin, squamous cells); sarcoma, as a cancer of connective tissue (e.g., bone, cartilage, fat, muscle, blood vessels, etc.); leukemia as a cancer of blood-forming tissue (e.g., bone marrow tissue); lymphoma and myeloma, which are cancers of immune cells; cancers of the central nervous system, including cancers in the brain and spinal tissue, may be included.

Specifically, the cancer may be selected from the group consisting of colon cancer, melanoma, liver cancer, gliocytoma ovarian cancer, colorectal cancer, head and neck cancer, bladder cancer, kidney cell cancer, stomach cancer, breast cancer, metastatic cancer, prostate cancer, gallbladder cancer, pancreatic cancer, blood cancer, skin cancer and lung cancer, but it is not limited thereto.

An embodiment of the present invention relates to a method for treatment of a cancer, which includes administering the compound, the stereoisomer or the pharmaceutically acceptable salt thereof to a subject in need thereof.

The treatment method may include administering the compound, the stereoisomer or the pharmaceutically acceptable salt thereof to a patient Who was diagnosed with cancer, at any stage of chemotherapy, and it is not limited to a specific stage.

Further, the compound, the stereoisomer or the pharmaceutically acceptable salt thereof may be administered in the aforementioned forms of the pharmaceutical composition, but it is not limited thereto.

The compound represented by Formula 1 according to an embodiment of the present invention may be prepared by any method known in various documents.

Hereinafter, the present invention will be described in detail by means of preparative examples and examples of the present invention.

PREPARATIVE EXAMPLE

Preparative Example 1: Synthesis of 2-(5-chloro-1H-indol-3-yl)-N-(6-morpholinebenzo[d]thiazol-2-yl)acetamide (Compound 6)

(1) Synthesis of perfluorophenyl 2-(5-chloro-1H-indol-3-yl)acetate

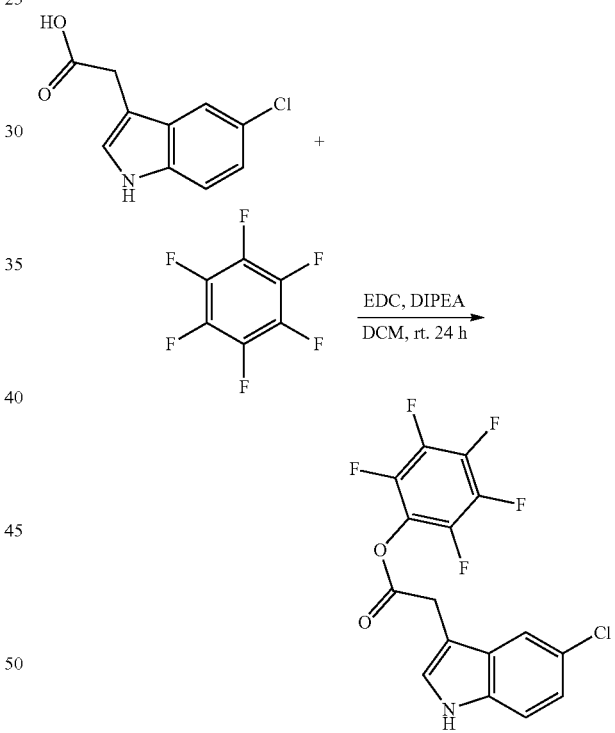

While stirring a solution of 2-(5-chloro-1H-indol-3-yl)acetic acid (56.00 g, 267.14 mmol), 2,3,4,5,6-pentafluorophenol (54.09 g, 293.85 mmol), and EDC-HCl (61.45 g, 320.57 mmol) in dichloromethane (890 mL) at room temperature, N,N-diisopropylethylamine (52.82 mL, 293.85 mmol) was added. After stirring the reaction mixture at room temperature for 24 hours and confirming the completion of the reaction, distilled water (890 mL) was added. The layers were separated, and the organic layer was dried over anhydrous $Na_2SO_4$ and filtered. After concentrating the filtrate under reduced pressure, the concentrate was purified by column chromatography to yield perfluorophenyl 2-(5-chloro-1H-indol-3-yl)acetate (50.00 g, yield 50%).

(2) Synthesis of 2-(5-chloro-1H-indol-3-yl)-N-(6-morpholinebenzo[d]thiazol-2-yl)acetamide (Compound 6)

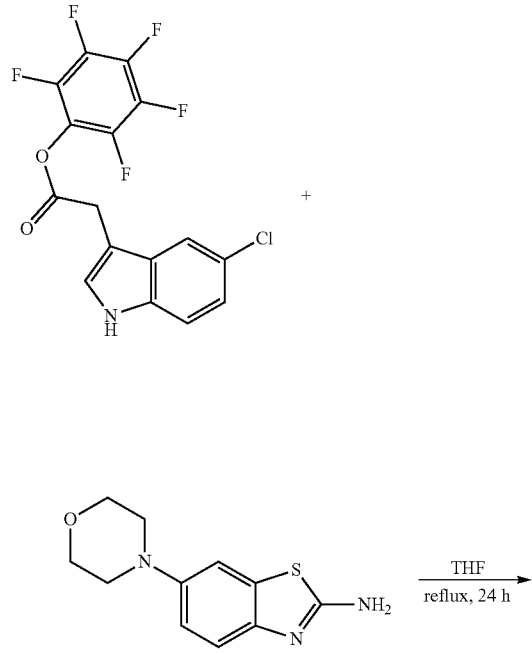

Compound 6

A solution of 6-morpholinobenzo[d]thiazol-2-amine (26.00 g, 110.49 mmol), perfluorophenyl 2-(5-chloro-1H-indol-3-yl)acetate (47.74 g, 127.07 mmol) in THF (1.1 L) was stirred. The reaction mixture was refluxed for 24 hours and completion of the reaction was confirmed, followed by cooling it to room temperature. The reaction mixture was concentrated under reduced pressure and purified by MPLC to yield Compound 6 (28.5 g, yield 60%).

$^1$H NMR (DMSO-d6, 400 MHz): δ 12.37 (s, 1H), 11.12 (s, 1H), 7.59 (t, 2H, J=16.0 Hz), 7.43 (d, 2H, J=16.0 Hz), 7.34 (s, 1H), 7.12 (d, 1H, J=8.0 Hz), 7.02 (d, 1H, J=12.0 Hz), 3.88 (m, 2H), 3.74 (m, 4H), 3.11 (m, 4H)

Preparative Example 2: Synthesis of 2-(5-chloro-1H-indol-3-yl)-N-(6-(4-methylpiperazin-1-yl)benzo[d]thiazol-2-yl)acetamide (Compound 9)

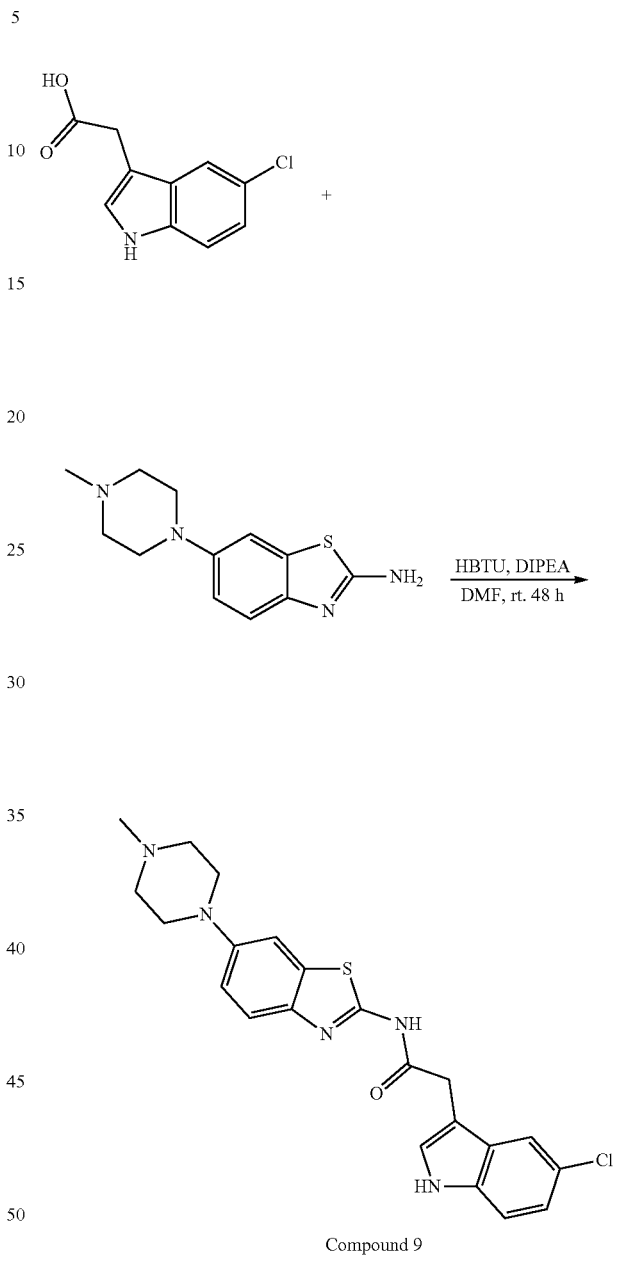

Compound 9

A solution of 2-(5-chloro-1H-indol-3-yl)acetic acid (210 mg, 1.00 mmol), 6-(4-methylpiperazin-1-yl)benzo[d]thiazol-2-amine (249 mg, 1.00 mmol), HBTU (760 mg, 2.00 mmol), and DIPEA (0.7 mL, 4.01 mmol) was added in DMF (10 ml) and stirred for 2 days. After completion of the reaction, the reaction mixture was put into ice-water (50 mL), stirred for 30 minutes, filtered, and washed with water. The obtained solid mixture was purified by column chromatography to yield Compound 9 (100 g, 22%).

$^1$H NMR (DMSO-d6, 400 MHz): δ 12.37 (s, 1H), 11.20 (s, 1H), 7.67 (d, 1H, J=4.0 Hz), 7.56 (d, 1H, J=8.0 Hz), 7.44 (d, 1H, J=4.0 Hz), 7.37 (m, 2H), 7.06 (m, 2H), 3.87 (s, 2H), 3.14 (m, 4H), 2.50 (m, 4H), 2.24 (s, 3H)

Preparative Example 3: Synthesis of 2-(5-chloro-1-methyl-1H-indol-3-yl)-N-(6-morpholinebenzo[d]thiazol-2-yl)acetamide (Compound 21)

(1) Synthesis of perfluorophenyl 2-(5-chloro-1-methyl-1H-indol-3-yl)acetate

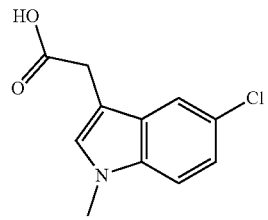

(2) Synthesis of 2-(5-chloro-1-methyl-1H-indol-3-yl)-N-(6-morpholinebenzo[d]thiazol-2-yl)acetamide (Compound 21)

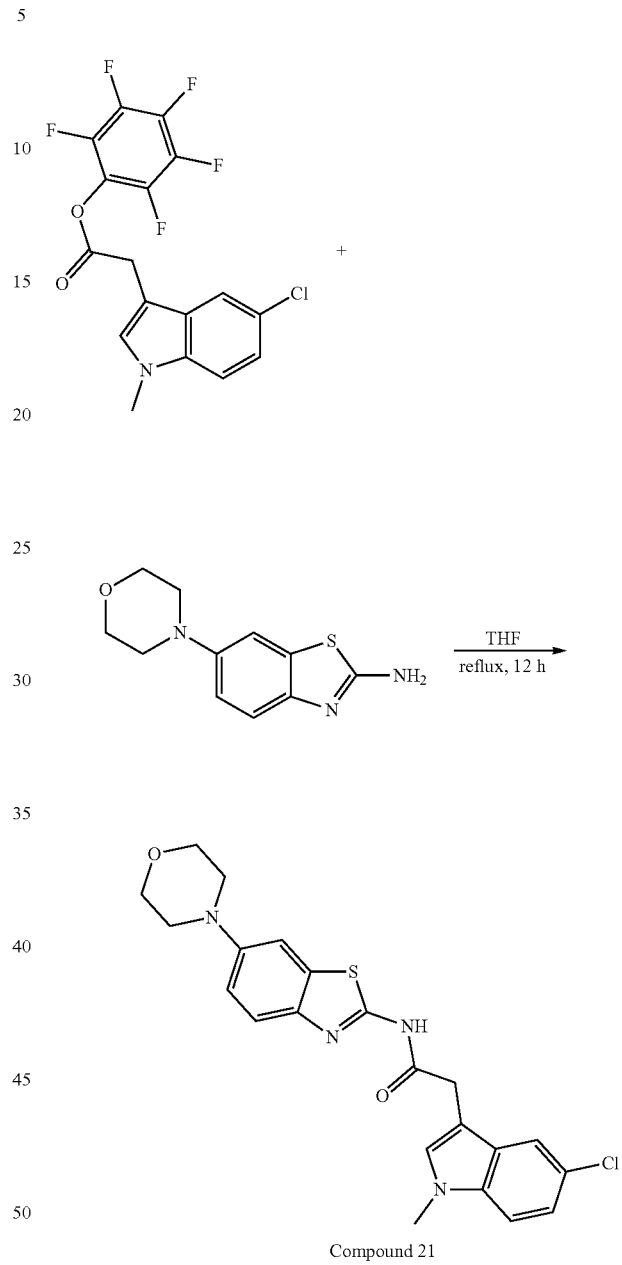

Compound 21

While stirring a solution of 2-(5-chloro-1-methyl-1H-indol-3-yl)acetic acid (110 mg, 491.83 μmol), 2,3,4,5,6-pentafluorophenol (100 mg, 541.01 μmol), EDC-HCl (113 mg, 590.19 μmol) in dichloromethane (1.6 mL), N,N-diisopropylethylamine (0.1 mL, 541.01 μmol) was added. After stirring the reaction mixture at room temperature for 24 hours and confirming the completion of the reaction, distilled water (2 mL) was added. The layers were separated, and the organic layer was dried over anhydrous $Na_2SO_4$ and filtered. After concentrating the filtrate under reduced pressure, the concentrate was purified by column chromatography to yield perfluorophenyl 2-(5-chloro-1-methyl-1H-indol-3-yl)acetate (150 mg, 78%).

A solution of 6-morpholinobenzo[d]thiazol-2-amine (40 mg, 169.99 μmol) and perfluorophenyl 2-(5-chloro-1-methyl-1H-indol-3-yl)acetate (99 mg, 254.99 μmol) in THF (1.7 mL) was stirred at reflux for 12 hours. The reaction mixture was cooled to room temperature, followed by filtering under reduced pressure to remove impurities, and the filtrate was concentrated under reduced pressure. The concentrated reaction mixture was recrystallized with diethyl ether to yield Compound 21 (40 mg, yield 54%).

$^1$H NMR (DMSO-d6, 500 MHz): δ 12.38 (s, 1H), 7.69 (s, 1H), 7.58 (d, 1H, J=10.0 Hz), 7.44 (d, 2H, J=5.0 Hz), 7.36 (s, 1H), 7.11 (m, 2H), 3.86 (s, 2H), 3.77 (s, 3H), 3.73 (m, 4H), 3.11 (m, 4H)

Preparative Example 4: Synthesis of 2-(5-hydroxy-1H-indol-3-yl)-N-(6-morpholinebenzo[d]thiazol-2-yl)acetamide (Compound 32)

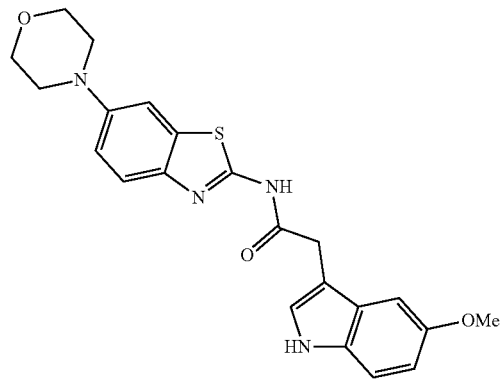

Compound 39

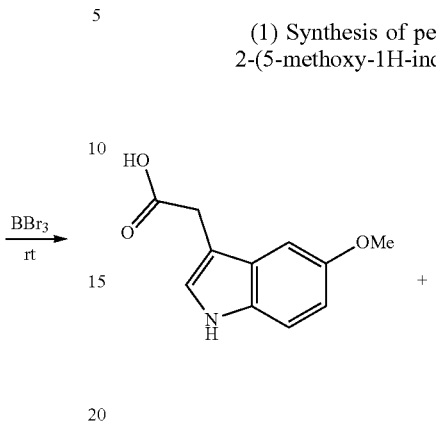

Compound 32

Compound 39 (2-(5-methoxy-1H-indol-3-yl)-N-(6-morpholinobenzo[d]thiazol-2-yl)acetamide) (25 mg, 59.17 μmol) obtained in Preparative Example 5 below in boron-tribromide (7.9 μml, 71.01 μmol) was stirred at room temperature for 6 hours. Distilled water was added to the reaction mixture to terminate the reaction. After neutralization with NaHCO$_3$, the layers were separated with DCM. The organic layer was washed, dried over anhydrous Na$_2$SO$_4$ and filtered. After concentrating the filtrate under reduced pressure, the concentrate was recrystallized with diethyl ether to yield Compound 32 (11 mg, yield 45%).

$^1$H NMR (DMSO-d6, 500 MHz): δ 12.30 (s, 1H), 10.65 (s, 1H), 8.64 (s, 1H), 7.57 (d, 1H, J=10.0 Hz), 7.45 (s, 1H), 7.19 (s, 1H), 7.11 (m, 2H), 6.90 (s, 1H), 6.59 (d, 1H, J=5.0 Hz), 3.78 (s, 2H), 3.74 (m, 4H), 3.11 (m, 4H)

Preparative Example 5: Synthesis of 2-(5-methyl-1H-indol-3-yl)-N-(6-morpholinebenzo[d]thiazol-2-yl)acetamide (Compound 39)

(1) Synthesis of perfluorophenyl 2-(5-methoxy-1H-indol-3-yl)acetate

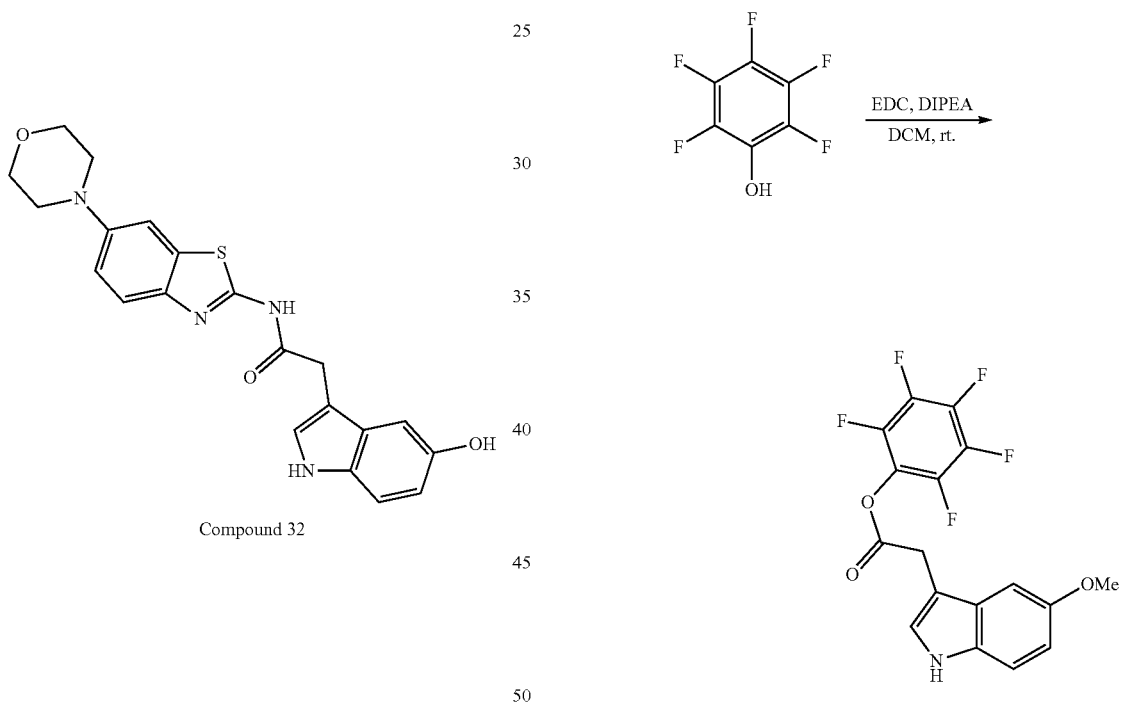

While stirring a solution of 2-(5-methoxy-1H-indol-3-yl)acetic acid (200 mg, 974.61 μmol), 2,3,4,5,6-pentafluorophenol (198 mg, 1.07 mmol), and EDC-HCl (225 mg, 1.17 mmol) in dichloromethane (3.3 mL), (N,N-diisopropylethylamine (0.2 mL, 1.07 mmol), was added. After stirring the reaction mixture at room temperature for 24 hours and confirming the completion of the reaction, distilled water (4 mL) was added. The layers were separated, and the organic layer was dried over anhydrous Na$_2$SO$_4$ and filtered. After concentrating the filtrate under reduced pressure, the concentrate was purified by column chromatography to yield the title compound (288 mg, 80%).

(2) Synthesis of 2-(5-methyl-1H-indol-3-yl)-N-(6-morpholinebenzo[d]thiazol-2-yl)acetamide (Compound 39)

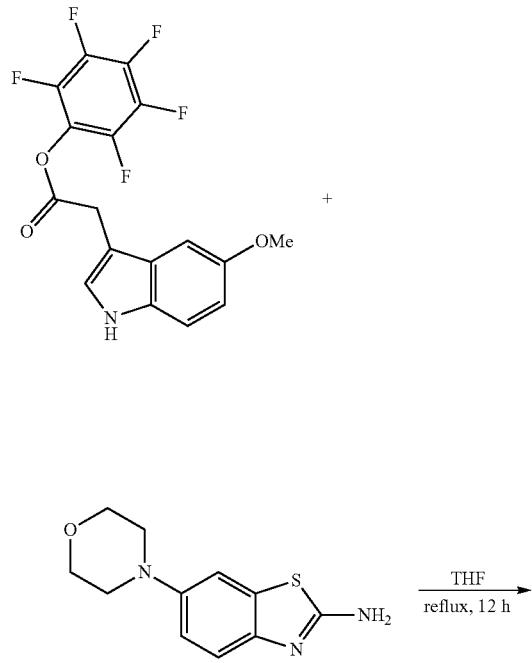

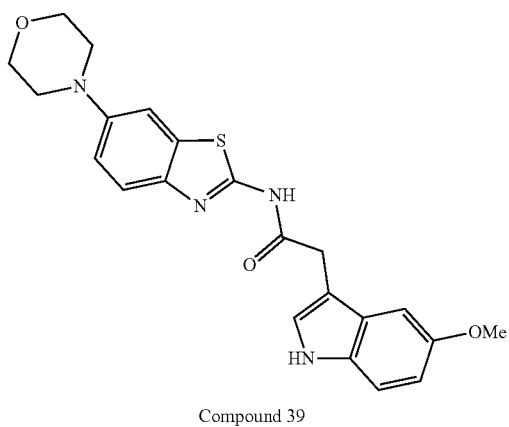

Compound 39

A solution of 6-morpholinobenzo[d]thiazol-2-amine (100 mg, 424.98 μmol) and perfluorophenyl 2-(5-methoxy-1H-indol-3-yl)acetate (189 mg, 509.98 μmol) in THF (4.3 mL) was stirred at reflux for 12 hours. The reaction mixture was cooled to room temperature, followed by filtering under reduced pressure to remove impurities, and the filtrate was concentrated under reduced pressure. The concentrated reaction mixture was recrystallized with diethyl ether to yield Compound 39 (120 mg, yield 67%).

$^1$H NMR (DMSO-d6, 500 MHz): δ 12.34 (s, 1H), 10.82 (s, 1H), 7.57 (d, 1H, J=10.0 Hz), 7.45 (s, 1H), 7.24 (d, 2H, J=10.0 Hz), 7.11 (m, 2H), 6.72 (dd, 1H, J=10.0 Hz), 3.84 (s, 2H), 3.74 (m, 7H), 3.10 (m, 4H)

Comparative Example 1: Synthesis of N-(benzo[d]thiazol-2-yl)-2-(5-chloro-1H-indol-3-yl)acetamide (Comparative Example 1)

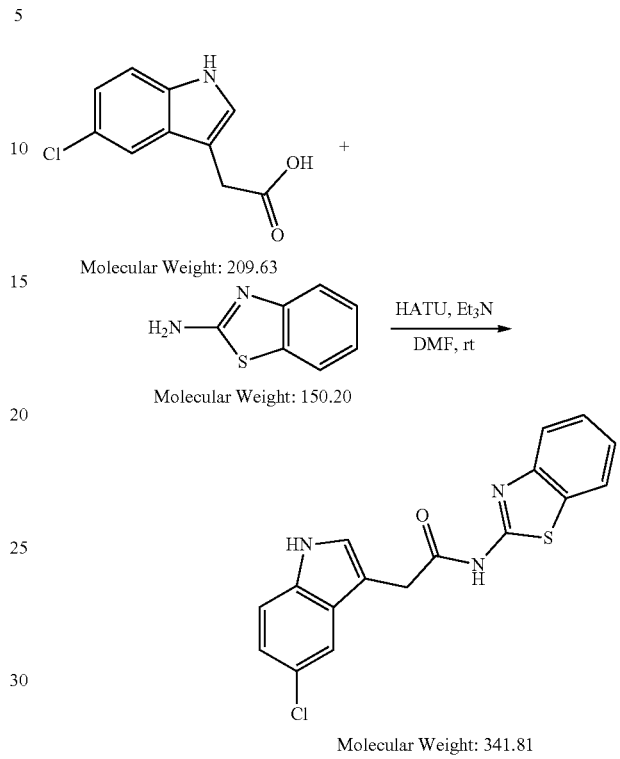

While stirring a solution of 2-(5-chloro-1H-indol-3-yl)acetic acid (7.0 g, 33.39 mmol) in DMF (100 mL) at room temperature, benzo[d]thiazol-2-amine (4.51 mg, 30.05 mmol), 1-[bis(dimethylamino)methylene]-1H-1,2,3-triazole[4,5-b]pyridinium-3-oxide hexafluorophosphate (HATU, 15.24 g, 40.07 mmol) and trimethylamine (9.4 mL, 66.78 mmol) were sequentially added. The reaction mixture was stirred at room temperature for 3 days. Distilled water was added to the mixture to terminate the reaction. The layers were separated with ethyl acetate, and the organic layer was washed with distilled water, dried over anhydrous Na$_2$SO$_4$, and filtered. After concentrating the filtrate under reduced pressure, the concentrate was purified by column chromatography to obtain a compound of Comparative Example 1 (5.0 g, yield 45%).

$^1$H NMR (DMSO-d6, 400 MHz): δ 12.57 (s, 1H), 11.21 (s, 1H), 7.94 (d, J=8.0 Hz, 1H), 7.73 (d, J=8.0 Hz, 1H), 7.68 (d, J=4.0 Hz, 1H), 7.37 (m, 3H), 7.27 (t, J=16.0 Hz, 1H), 7.07 (dd, J=8.0 4.0 Hz, 1H), 3.91 (s, 2H)

EXAMPLE

Example 1: Confirmation of Effects of Inducing CYP1A1 Expression

In order to confirm target specificity of the compounds of an embodiment of the present invention prepared as above, it was confirmed whether the expression levels of CYP1A1 mRNA and CYP1A1 protein, which are AHR target genes, were increased.

(1) Effects of Inducing CYP1A1 mRNA Expression

After recovering HepG2 under culture in DMEM-fetal bovine serum (FBS) 10% medium and then confirming that the survival rate is 97% or more through trypan blue staining, the recovered product was centrifuged at a speed of 1200 rpm for 5 minutes at room temperature, and the cells were prepared by resuspending them in DMEM-fetal calf serum 10% medium at $3 \times 10^5$ cells/ml. Thereafter, the cells were dispensed onto a 60 mm dish by 3 ml, and each dish was treated with 50 μl of Compounds 6, 21, 32 and 39 at a concentration of 1 μM diluted in DMEM medium, and then cultured in a cell incubator (5% $CO_2$ incubator) for 24 hours. As a control, 50 μl of 0.05% dimethylsulfoxide (DMSO)/DMEM medium was used for treatment.

The cultured cells were recovered to prepare an mRNA sample. Specifically, mRNA was extracted from the recovered cells by a phenol-chloroform precipitation method using TRIZOL reagent (Invitrogen, Cat No. 15596018). From the separated RNA, cDNA was synthesized by reverse transcription, and the expression of CYP1A1 was confirmed through a real-time polymerase chain reaction (PCR) using iQ SYBR-Green Supermix (Bio-rad) in a CFX96 (Bio-rad) detection system. Relative values of the enzyme expression levels were compared by ΔΔct method using GAPDH as a control enzyme. Herein, one (1) fold was set using the control.

The real-time polymerase chain reaction was performed under the conditions of 45 cycles at an annealing temperature of 58° C., wherein the following primer sequences were used.

```
Human CYP1A1
forward,
                                         (SEQ ID NO: 1)
5'-CAC CCT CAT CAGTAA TGG TCA GA-3'
and reverse,
                                         (SEQ ID NO: 2)
5'-AAC GTG CTT ATC AGG ACC TC-3';

Human GAPDH
forward,
                                         (SEQ ID NO: 3)
5'-TGA TGA CAT CAA GAA GGT GG-3'
and reverse,
                                         (SEQ ID NO: 4)
5'-TTA CTC CTT GGA GGC CAT GT-3'.
```

From the above results, it can be confirmed that groups treated with Compounds 6, 21, 32 and 39 showed higher CYP1A1 mRNA expression levels than the control (vehicle). Accordingly, it was confirmed that Compounds 6, 21, 32 and 39 significantly induced the expression of CYP1A1, an AHR target gene (FIG. 1).

(2) Effect of Inducing CYP1A1 Protein Expression

After recovering HepG2 under culture in DMEM-fetal bovine serum (FBS) 10% medium and then confirming that the survival rate is 97% or more through trypan blue staining, the recovered product was centrifuged at a speed of 1200 rpm for 5 minutes at room temperature, and the cells were prepared by resuspending them in DMEM-fetal calf serum 10% medium at $1.5 \times 10^5$ cells/ml.

Thereafter, the cells were dispensed onto a 96-well plate by 200 μl, and each plate was treated with 3 μl of Compounds 6, 21, 32 and 39 at a concentration of 1 μM diluted in DMEM medium, and then cultured in a cell incubator (5% $CO_2$ incubator) for 24 hours. As a control, 3 μl of 0.05% dimethylsulfoxide (DMSO)/DMEM medium was used for treatment.

After 24 hours, the medium of the plate was discarded, washed with dPBS, treated with 100 μl of 2 μM 7-ethoxyresorufin, and cultured in a cell incubator (5% $CO_2$ incubator) for 30 minutes. After 30 minutes, each 75 μl of fluorescamine (150 μg/ml) was treated, then resorufine excitation was measured at 535 nm and emission at 590 nm. The standard curve was measured and used with 0 to 50 pmol of resorufin solution.

After measurement, all solutions were removed, followed by treating the same with 25 μl of 0.5 M sodium hydroxide (NaOH), the cells were scraped and reacted in a shaker at room temperature for 15 minutes.

After 15 minutes, protein was quantified using a Bradford method, and a value was obtained using a calculation formula (sample resorufin amount/sample protein amount), and then one (1) fold was set using the control.

Figure 2:
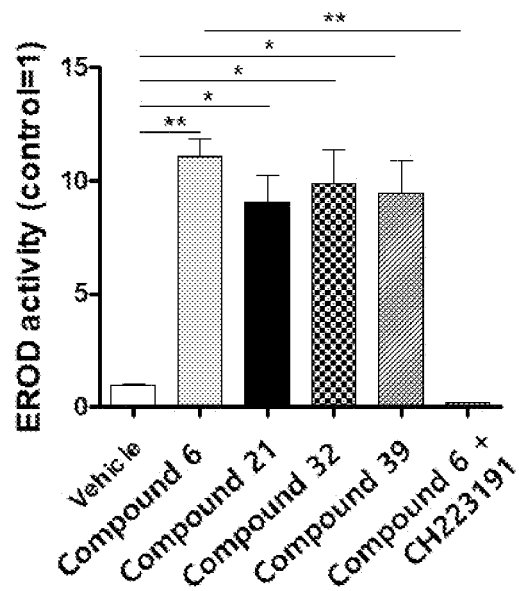

From the above results, it can be confirmed that the CYP1A1 protein expression level is significantly higher in the groups treated with Compounds 6, 21, 32 and 39 than the control (vehicle), and therefore, it was confirmed that protein of AHR-target gene CYP1A1 was significantly induced by Compounds 6, 21, 32 and 39 (FIG. 2).

Example 2: Inhibitory Effects of Production of Inflammatory Factor IL-6

In order to assess the inhibitory effects of production of IL-6 by the compounds of the present invention prepared as above, an IL-6 production test of epithelial cells by stimulation of IL-1β was performed.

After recovering A549 cells under culture in DMEM-fetal bovine serum (FBS) 10% medium and confirming that the survival rate is 97% or more through trypan blue staining, the recovered product was centrifuged at a speed of 1200 rpm for 5 minutes at room temperature, and the cells were prepared by resuspending them in DMEM-10% fetal bovine serum medium at $1 \times 10^6$ cells/3 ml. Thereafter, the cells were dispensed by 3 ml onto a 60 mm plate, and each dish was treated with 50 μl of Compounds 6, 9, 21, 32 and 39 at a concentration of 5 μM diluted in DMEM medium, and then cultured in a cell incubator (5% $CO_2$ incubator) for 48 hours. Then, the cells were treated with 50 μl of human recombinant IL-1β at a concentration of 12.5 ng/ml diluted in DMEM medium, followed by culturing the same in a cell incubator (5% CO2 incubator) for 24 hours. As a control, 50 μl of 0.05% dimethylsulfoxide (DMSO)/DMEM medium was used for treatment.

The cultured cells were recovered to prepare an mRNA sample. Specifically, mRNA was extracted from the recovered cells by a phenol-chloroform precipitation method using TRIZOL reagent (Invitrogen, Cat No. 15596018). From the separated RNA, cDNA was synthesized by reverse transcription, and the expression of CYP1A1 was confirmed through a real-time polymerase chain reaction (PCR) using iQ SYBR-Green Supermix (Bio-rad) in a CFX96 (Bio-rad) detection system. Relative values of the enzyme expression levels were compared by ΔΔct method using GAPDH as a control enzyme. Herein, one (1) fold was set using the control.

The real-time polymerase chain reaction was performed under the conditions of 45 cycles at an annealing temperature of 58° C., wherein the following primer sequences were used.

```
Human IL-6
forward,
                                 (SEQ ID NO: 5)
5'-GAT GGC TGA AAA AGA TGG ATG C-3'
and reverse,
                                 (SEQ ID NO: 6)
5'-TGG TTG GGT CAG GGG TGG TT-3';

Human GAPDH
forward,
                                 (SEQ ID NO: 3)
5'-TGA TGA CAT CAA GAA GGT GG-3'
and reverse,
                                 (SEQ ID NO: 4)
5'-TTA CTC CTT GGA GGC CAT GT-3'.
```

Figure 3:
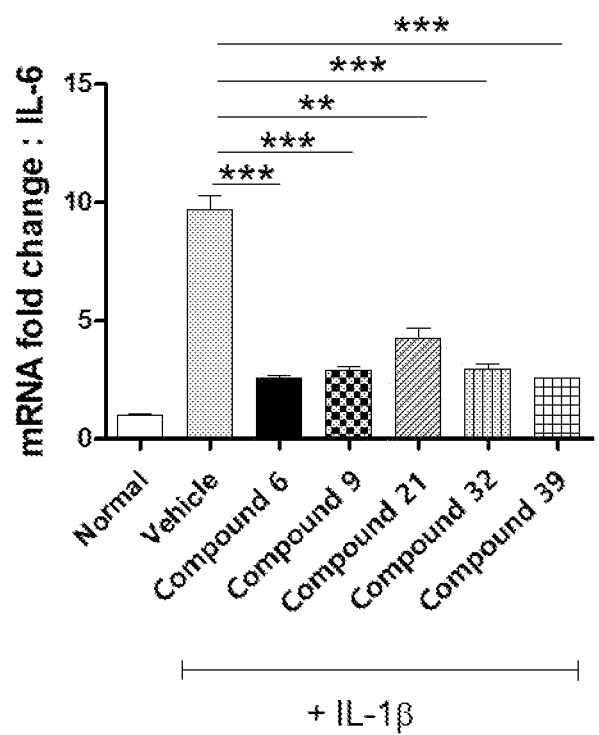
FIG. 3 illustrates measurement of inflammatory factor IL-6 production inhibitory effects of the compound of an embodiment of the present invention.

As a result, it was confirmed that IL-6 production of A549 by IL-1β stimulation was significantly reduced by treatment with Compounds 6, 9, 21, 32 and 39, and therefore, IL-6 production was effectively inhibited by Compounds 6, 9, 21, 32 and 39 (FIG. 3).

Example 3: Confirmation of Effects of Promoting Production of Foxp3-Expressing Regulatory T Cells (Treg)

Figure 4:
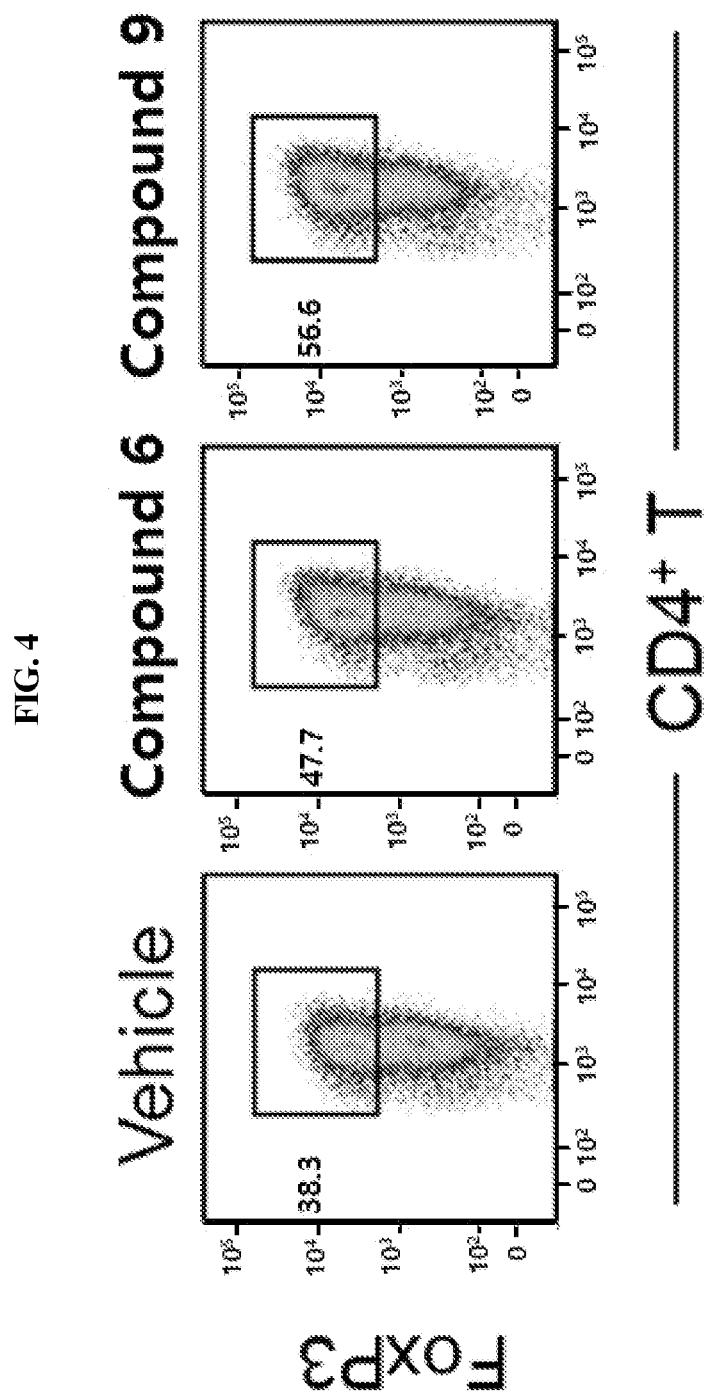
FIG. 4 illustrates measurement of Foxp3+ regulatory T cell production promotion effects of the compound of an embodiment of the present invention.
Figure 5:
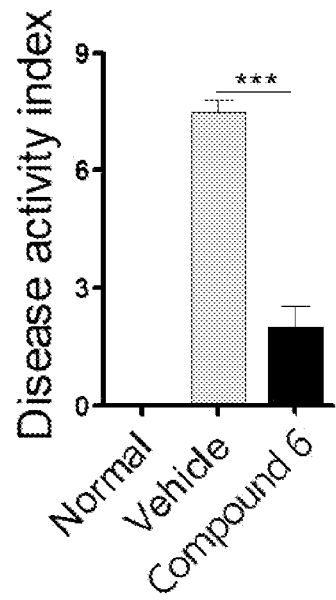
Figure 6:
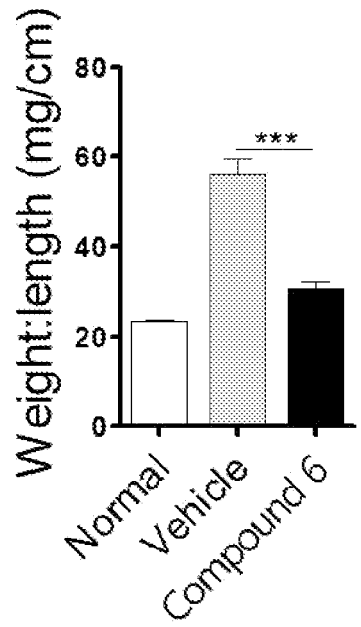

Effects of promoting the production of "FoxP3-expressing regulatory T cells," which play an important role in maintaining immune tolerance, was evaluated (FIG. 4).

The spleen of C57BL/6 mice (8 to 12 weeks old, female) was excised, pulverized by adding RPMI medium, and then passed through a 40 μm cell strainer (BD Falcon), thereby obtaining a single cell suspension. The single cell suspension was centrifuged (1200 rpm, 5 minutes), and after discarding the supernatant, 1 ml of ACK lysis buffer was added, followed by stirring for 1 minute and then washing the same with RPMI medium. After the single cell suspension was centrifuged, T-cells were separated using a Mouse CD4 Naive T cell Enrichment Kit (Invitrogen). The separated T-cells were prepared by resuspending them in RPMI-fetal bovine serum (FBS) 10%+2-ME (mercaptoethanol) medium at 1×10⁶/ml. For T-cell activation, 5 μg/ml anti-CD3 (eBioscience™) was dispensed by 100 μl onto a 96-well plate, reacted in a cell incubator (37° C., 5% $CO_2$ incubator) for 4 hours, and washed with phosphate buffered saline to prepare the plate. The T-cells were dispensed by 200 μl onto the prepared plate, and each well was treated with 2 μg/ml of anti-CD28 (eBioscience™), 2 ng/ml of TGFβ-1 (R&D systems), and 100 U/ml of IL-2. Each 5 μl of Compounds 6 and 9 at a concentration of 2.5 μM diluted in RPMI-fetal bovine serum 10%+2-ME medium was used for treatment, followed by culturing the same in a cell incubator (37° C., 5% $CO_2$ incubator) for 3 days. As a control, 5 μl of 0.05% dimethylsulfoxide (DMSO)/RPMI medium was used for treatment. After 3 days, in order to confirm effects of producing regulatory T cells, the cultured cells were recovered to measure the expression of Foxp3 protein.

In order to confirm the expression of Foxp3 protein, the recovered cells were placed in a 5 ml FACS tube (BD Falcon) and washed with 1 ml of phosphate buffered saline. The cells were resuspended in 0.1 ml of FACS buffer (0.1% NaN3, 1% FBS) and treated with 0.5 μg of CD16/CD32 antibody (eBioscience™) to prevent non-specific binding of the antibody, then reacted at 4° C. for 15 minutes. Thereafter, the cells were treated with 0.25 μg of CD4 Monoclonal Antibody (GK1.5) and PE-Cyanine7 (eBioscience™), and stained at 4° C. for 30 minutes, followed by washing with 1 ml of FACS buffer. Then, 1 ml of Fixation/Permeabilization solution (eBioscience™) was added to the FACS tube containing each sample, followed by reaction at 4° C. for 1 hour. Then, the product was washed twice with Permeabilization buffer (eBioscience™). Thereafter, 0.5 μg of Foxp3 Monoclonal Antibody (eBioscience™) was used for treatment, followed by staining the same at 4° C. for 30 minutes. The cells were washed twice with the Permeabilization buffer, suspended in 0.3 ml of FACS buffer, and measured by flow cytometry.

As a result, it was confirmed that the production of Foxp3-expressing regulatory T cells was markedly increased by Compounds 6 and 9 compared to Vehicle, and therefore, the production of FoxP3+ regulatory T cells was effectively promoted by Compounds 6 and 9 (FIG. 4).

Example 4: Confirmation of Therapeutic Effects of Inflammatory Bowel Diseases

In order to investigate the therapeutic effects of the compounds according to the present invention prepared as above on inflammatory bowel disease, the inflammatory bowel disease was induced in C57BL/6 mice, and Compound 6 was administered to the mice to evaluate the efficacy as follows (FIGS. 5 to 10).

(1) Confirmation of Therapeutic Effects of Compound 6 on Inflammatory Bowel Diseases On day 0 of the experiment, a 2.0% DSS solution prepared by dissolving DSS (Dextran sulfate sodium, MP biomedicals, Cat No. 160110) in 2.0% sterile distilled water was given for drinking to C57BL/6 mice (11 weeks old, female, 20±2 g) for 7 days. The 2.0% DSS solution was changed at an interval of 2 days. Sterile distilled water was provided for drinking from the 8th day of the experiment. Body weight and severity index were measured at an interval of 2 days from the 0th day of the experiment in order to confirm the onset of inflammatory bowel disease.

10 mg/kg of Compound 6 per mouse was completely dissolved in an ethanol-Cremophor EL mixture corresponding to 7.5% (v/v) of the administered dose, and then, was diluted in phosphate buffered saline to prepare the final ethanol:Cremophor EL:phosphate buffered saline (0.375:0.375:9.25, v/v/v), followed by oral administration of 200 μl daily for a total of 14 times from the 1st to 14th days of the experiment. An inflammatory bowel disease severity index was visually observed and recorded at an interval of 2 days according to a severity index system classified into 0 to 10 levels.

Inflammatory bowel disease symptoms were evaluated by summing the scores of three items according to the following items (Table 2).

TABLE 2

| | Symptoms | | |
|---|---|---|---|
| Score | Watery of excrement | Melena state | Reduction of Body weight |
| 0 | Normal form | Normal form | Normal |
| 1 | Slightly loose feces | Brown excrement | 5-10% decrease |
| 2 | Loose feces | Redish brown excrement | 11-15% decrease |
| 3 | Diarrhea | Melena | 16-20% decrease |
| 4 | — | — | >20% decrease |

As a result of the analysis, it was confirmed that the body weight of the solvent control (Vehicle) started to decrease from the 6th day of the experiment, decreased by 10% or more on the 10th day of the experiment, and 100% of enteritis was induced along with an increased severity index of 5 or more. The mice in the solvent control showed a severity index of 7.50±0.50 on the 10th day of the experiment when the severity index reached the maximum. On the other hand, the experimental group administered with 10 mg/g of Compound 6 of an embodiment of the present invention showed statistically significant therapeutic effects compared to the solvent control on the 10th day of the experiment. Further, comparison of the colon weight:length ratio on the 15th day of the experiment (weight:length ratio, mg/cm) demonstrated that intestinal inflammation could be significantly suppressed in terms of morphology (compared to the solvent control (Vehicle): *, p<0.001, see FIGS. 5 and 6**). Specifically, Compound 6 of an embodiment of the present invention showed excellent anti-inflammatory effects when administered in an amount of 10 mg/kg.

On the 15th day of the experiment, the colon of the mouse was excised to prepare an mRNA sample. In order to extract mRNA, the colon tissue was ground with a homogenizer to acquire a homogeneous suspension. From the homogeneous suspension, mRNA was extracted by a phenol-chloroform sedimentation method using an easy-spin™ (DNA free) total RNA extraction kit (Intron biotechnology, Cat No. 17221). From the isolated RNA, cDNA was synthesized by reverse transcription, followed by confirming the expression of inflammatory cytokines through real-time polymerase chain reaction (PCR) using iQ SYBR-Green Supermix (Bio-rad) in the CFX96 (Bio-rad) detection system. Relative values of the enzyme expression levels were compared by the ΔΔct method using GAPDH as a control enzyme. Herein, one (1) fold was set using the normal mouse colon as a control.

The real-time polymerase chain reaction was implemented under the conditions of 45 cycles at an annealing temperature of 58° C. and the following primer sequences were used.

```
Mouse IL-1β
forward,
                                         (SEQ ID NO: 7)
5'-CTC GTG CTG TCG GAC CCA TAT-3'
and reverse,
                                         (SEQ ID NO: 8)
5'-TTG AAG ACA AAC CGC TTT TCC A-3';

Mouse IL-6
forward,
                                         (SEQ ID NO: 9)
5'-CAT GTT CTC TGC GAA ATC GTG G-3'
and reverse,
                                        (SEQ ID NO: 10)
5'-AAC GCA CTA GGT TTG CCG AGT A-3';

Mouse IL-17A
forward,
                                        (SEQ ID NO: 11)
5'-TTT AAC TCC CTT GGC GCA AAA-3'
and reverse,
                                        (SEQ ID NO: 12)
5'-CTT TCC CTC CGC ATT GAC AC-3';
```

```
Mouse TNF-α
forward,
                                        (SEQ ID NO: 13)
5'-CCA CAC CGT CAG CCG ATT TG-3'
and reverse,
                                        (SEQ ID NO: 14)
5'-CAC CCA TTC CCT TCA CAG AGC-3';

Mouse S100a8
forward,
                                        (SEQ ID NO: 15)
5'-AAA TCA CCA TGC CCT CTA CAA G-3'
and reverse,
                                        (SEQ ID NO: 16)
5'-CCC ACT TTT ATC ACC ATC GCA A-3';

Mouse S100a9
forward,
                                        (SEQ ID NO: 17)
5'-ATA CTC TAG GAA GGA AGG ACA CC-3'
and reverse,
                                        (SEQ ID NO: 18)
5'-TCC ATG ATG TCA TTT ATG AGG GC-3';

Mouse IL-10
forward,
                                        (SEQ ID NO: 19)
5'-CAA GGC AGT GGA GCA GGT GAA-3'
and reverse,
                                        (SEQ ID NO: 20)
5'-CGG AGA GAG GTA CAA ACG AGG TT-3';

Mouse Foxp3
forward,
                                        (SEQ ID NO: 21)
5'-CCC ATC CCC AGG AGT CTT G-3'
and reverse,
                                        (SEQ ID NO: 22)
5'-ACC ATG ACT AGG GGC ACT GTA-3';

Mouse Reg3b
forward,
                                        (SEQ ID NO: 23)
5'-ACT CCC TGA AGA ATA TAC CCT CC-3'
and reverse,
                                        (SEQ ID NO: 24)
5'-CGC TAT TGA GCA CAG ATA CGA G-3';

Mouse Muc2
forward,
                                        (SEQ ID NO: 25)
5'-ATG CCC ACC TCC TCA AAG AC-3'
and reverse,
                                        (SEQ ID NO: 26)
5'-GTA GTT TCC GTT GGA ACA GTG AA-3';

Mouse GAPDH
forward,
                                        (SEQ ID NO: 27)
5'-TTC ACC ACC ATG GAG AAG GC-3'
and reverse,
                                        (SEQ ID NO: 28)
5'-GGC ATG GAC TGT GGT CAT GA-3'.
```

Figure 7:
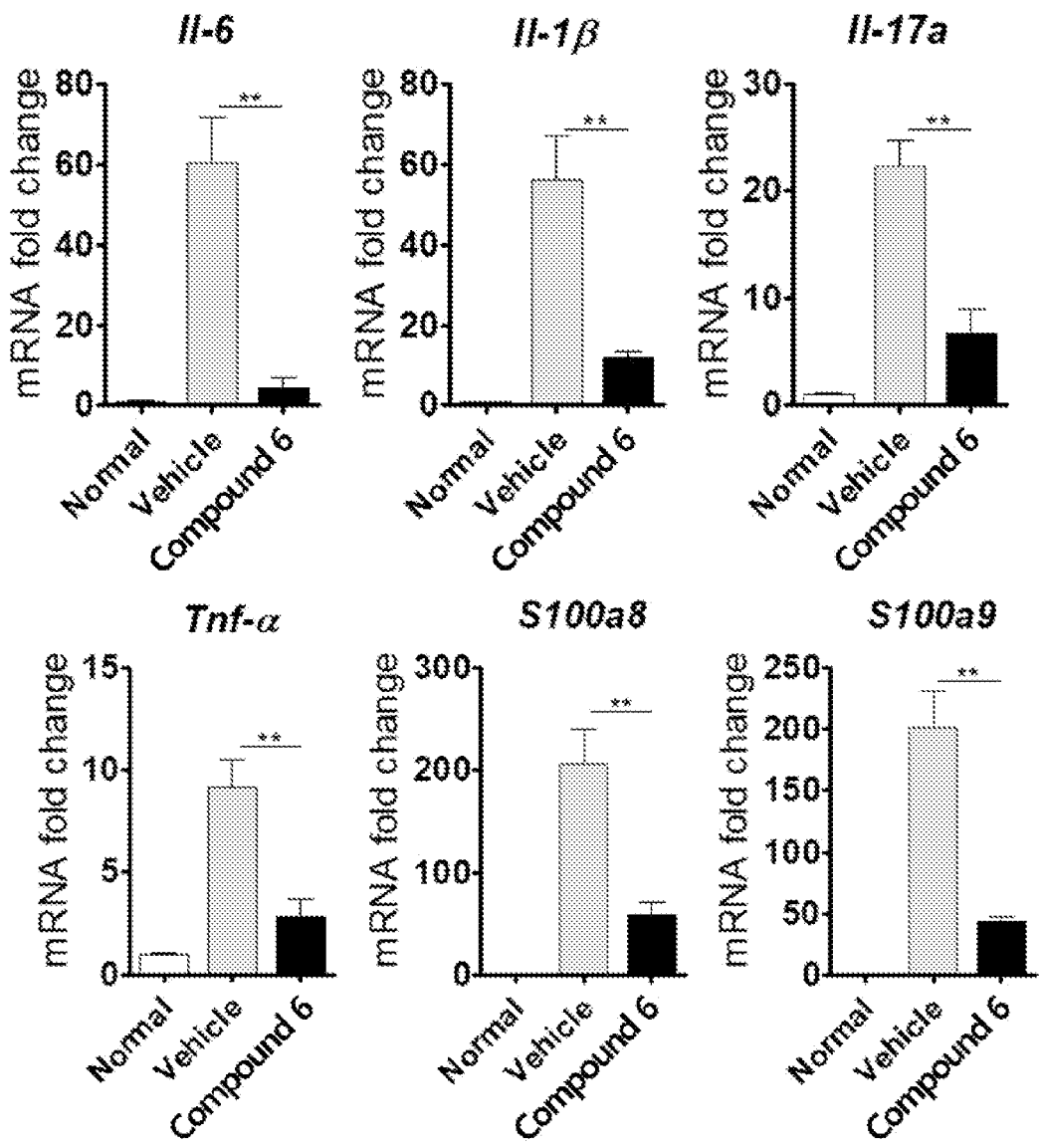
FIGS. 7 to 9 illustrate effects of the compound of an embodiment of the present invention on inhibiting the expression of inflammatory factors (IL-1β, IL-6, IL-17a, TNF-α, S100a8, and S100a9) (FIG. 7), increasing the expression of immunomodulatory factors (IL-10, and Foxp3) (FIG. 8), and increasing the expression of intestinal epithelial cell protective factors (Reg3b, and Muc2) (FIG. 9) in an animal model with DSS-induced inflammatory bowel disease.
Figure 8:
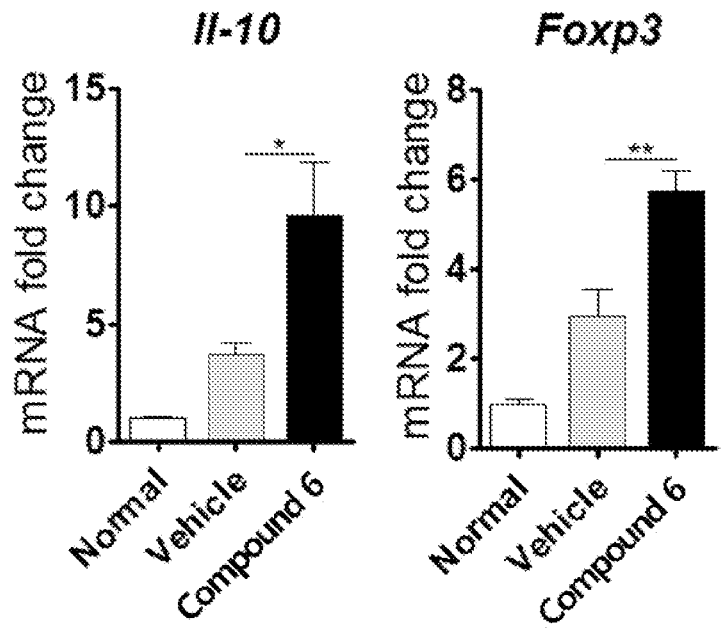
Figure 9:
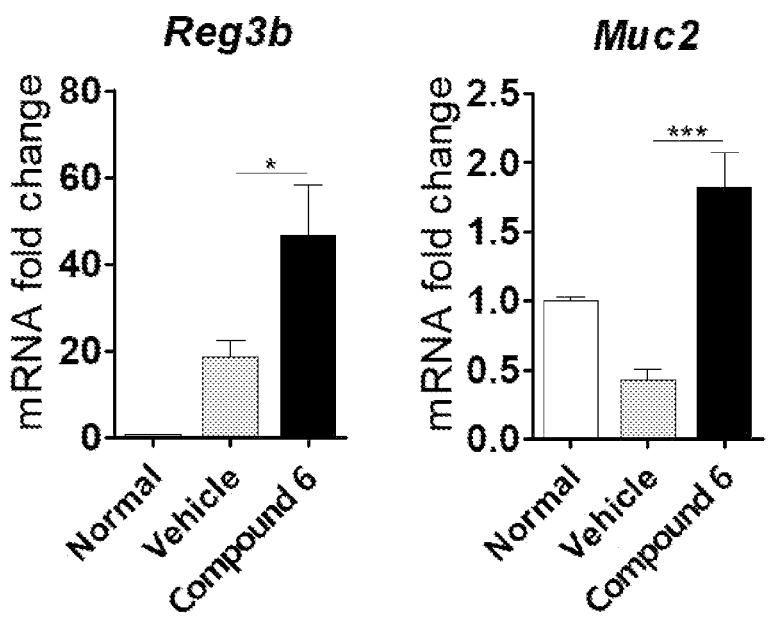

The expression levels of the inflammatory cytokines IL-1β, IL-6, IL-17A, TNF-α, S100a8, and S100a9 in colon lesions were significantly reduced compared to the solvent control (Vehicle) by administration of Compound 6 (compared to the solvent control (Vehicle): **, p<0.01, see FIG. 7). In addition, the expression levels of the immunomodulatory factors IL-10 and Foxp3 in colon lesions were significantly increased compared to the solvent control (Vehicle) by administration of Compound 6 (compared to the solvent control (Vehicle): *, p<0.05; **, p<0.01, see FIG. 8). Further the expression levels of intestinal epithelial cell protective factors Reg3b and Muc2 in colon lesions were significantly increased compared to the vehicle control (Vehicle) by administration of Compound 6 (compared to the solvent control (Vehicle): *, p<0.05; ***, p<0.001, see FIG. 9). From these results, it could be seen that Compound 6 of an embodiment of the present invention can significantly reduce the expression of inflammatory factors in the intestine, while significantly increasing the expressions of intestinal immunomodulatory factors and intestinal epithelial cell protective factors.

In order to investigate mucosal healing effects of the compounds according to an embodiment of the present invention, inflammatory bowel disease was induced in C57BL/6 mice, and a degree of recovery of intestinal epithelial harrier integrity was assessed by administering Compound 6 as follows.

On day 0 of the experiment, a 2.0% DSS solution prepared by dissolving 2.0% DSS in sterile distilled water was given for drinking to C57BL/6 mice (11 weeks old, female, 20±2 g) for 7 days. The 2.0% DSS solution was changed at an interval of 2 days. Sterile distilled water was provided for drinking from the 8th day of the experiment. Body weight and severity index were measured at an interval of 2 days from the 0th day of the experiment, so as to confirm the onset of inflammatory bowel disease.

In the compound 6 administration group according to an embodiment of the present invention, 10 mg/kg of the compound per mouse was completely dissolved in an ethanol-Cremophor EL mixture corresponding to 7.5% (v/v) of the administered dose, and then, was diluted in phosphate buffered saline to prepare the final ethanol:Cremophor EL (0.375:0.375:9.25, v/v/v), followed by oral administration with 200 µl of the prepared solution daily for a total of 14 times from the 1st to 14th days of the experiment.

One day before FITC-dextran administration, a mouse was deprived of water overnight. On the 15th day of the experiment 600 mg/kg of FITC-dextran (Fluorescein isothiocyanate-dextran, Sigma Aldrich, Cat No. FD40) was diluted in a phosphate buffered saline and administered orally to the mouse at 200 µl once. 4 hours after oral administration, fluorescence was measured in the serum extracted from the heart (fluorometer, excitation 485490 nm, emission 528-330 nm).

Figure 10:
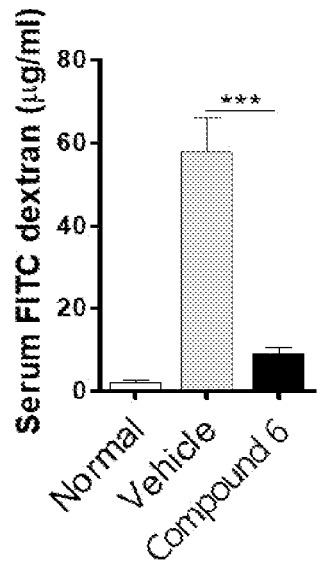
FIG. 10 illustrates mucosal healing effects of the compound of an embodiment of the present invention using FITC-dextran in an animal model with DSS-induced inflammatory bowel disease. Herein, it means that the lower the detection degree, the higher the mucosa healing effects are.

Serum FITC-dextran was significantly decreased compared to the solvent control (Vehicle) by administration of Compound 6 (compared to solvent control (Vehicle): ***, p<0.001, see FIG. 10). From the above results result, it could be seen that Compound 6 of an embodiment of the present invention showed significant mucosal healing effects. From the above results, it was confirmed that Compound 6 of an embodiment of the present invention has oral administration therapeutic effects in a mouse model of inflammatory bowel disease.

Example 5: Confirmation of Effects of Preventing and Treating Colon Cancer

In order to investigate the effects of the compounds according to an embodiment of the present invention prepared as above to prevent (FIGS. 11 and 12) and treat (FIGS. 13 and 14) colitis-associated colorectal cancer (CA-CRC), medical efficacy was evaluated by administering Compound 6 to a colorectal cancer model (AOM/DSS mouse).

AOM (Sigma Aldrich, Cat No. A5486) was diluted with physiological saline so as to be a concentration of 10 mg/kg, and then administered intraperitoneally to C57BL/6 mice (8 weeks old, female, 18±2 g) by 2000 µl for a total of 3 times at an interval of 7 days (Experiment day 0, 7, 14th). On the 7th day of the experiment, a 1.5% DSS solution prepared by dissolving 1.5% DSS in sterile distilled water was given for drinking to the mice for 7 days. Further, the 1.5% DSS solution was changed at an interval of 2 days. Sterile distilled water was provided for drinking from the 8th day of the experiment.

In the compound 6 administration group according to an embodiment of the present invention, 10 mg/kg of Compound 6 per mouse was completely dissolved in an ethanol-Cremophor EL mixture corresponding to 7.5% (v/v) of the administered dose, and then, was diluted in phosphate buffered saline to prepare the final ethanol:Cremophor EL:phosphate buffered saline (0.375:0.375:9.25, v/v/v), followed by oral administration with 200 µl of the prepared solution. In order to confirm the preventive effect, Compound 6 was administered for a total of 14 times from the 7th to the 20th days of the experiment.

Figure 11:
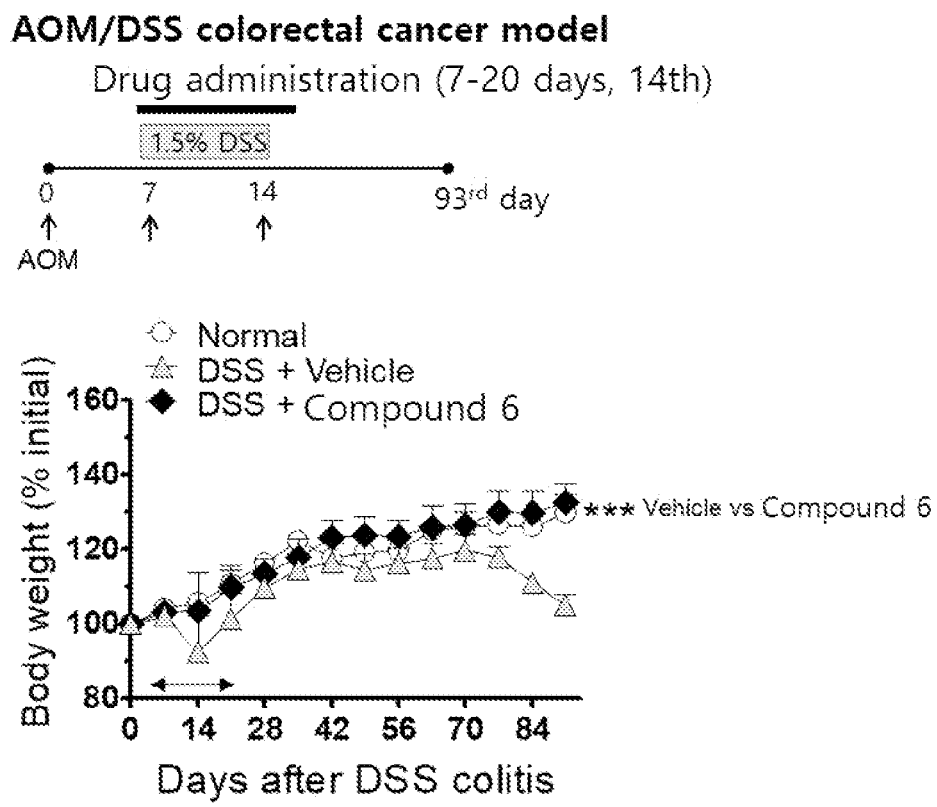
FIGS. 11 and 12 illustrate effects of the compound of an embodiment of the present invention on preventing colon cancer in AOM/DSS-colorectal cancer animal models, and specifically, show changes in the body weight (FIG. 11) and the number and size of tumors (FIG. 12) of mice (Normal) not administered with a colorectal cancer-inducing drug (AOM/DSS), mice (DSS+Vehicle) administered with AOM/DSS, and mice (DSS+Compound 6) administered with Compound 6 at the time of AOM/DSS administration.
Figure 12:
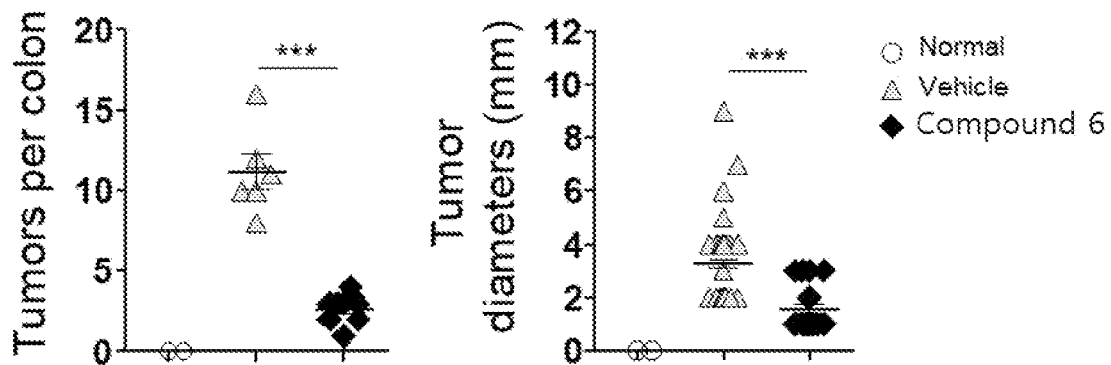

As a result, the control (AOM/DSS+Vehicle) showed a decrease in the body weight after 70 days, but the group administered with Compound 6 (AOM/DSS+Compound 6) showed an increase in the body weight similar to that of normal mice (Normal) (FIG. 11). In addition, it was confirmed that the number of tumors was significantly smaller in the compound 6 administration group and the size was also significantly smaller than the control. That is, it was confirmed that Compound 6 has effects of preventing colorectal cancer caused by inflammation (FIGS. 11 and 12).

Figure 13:
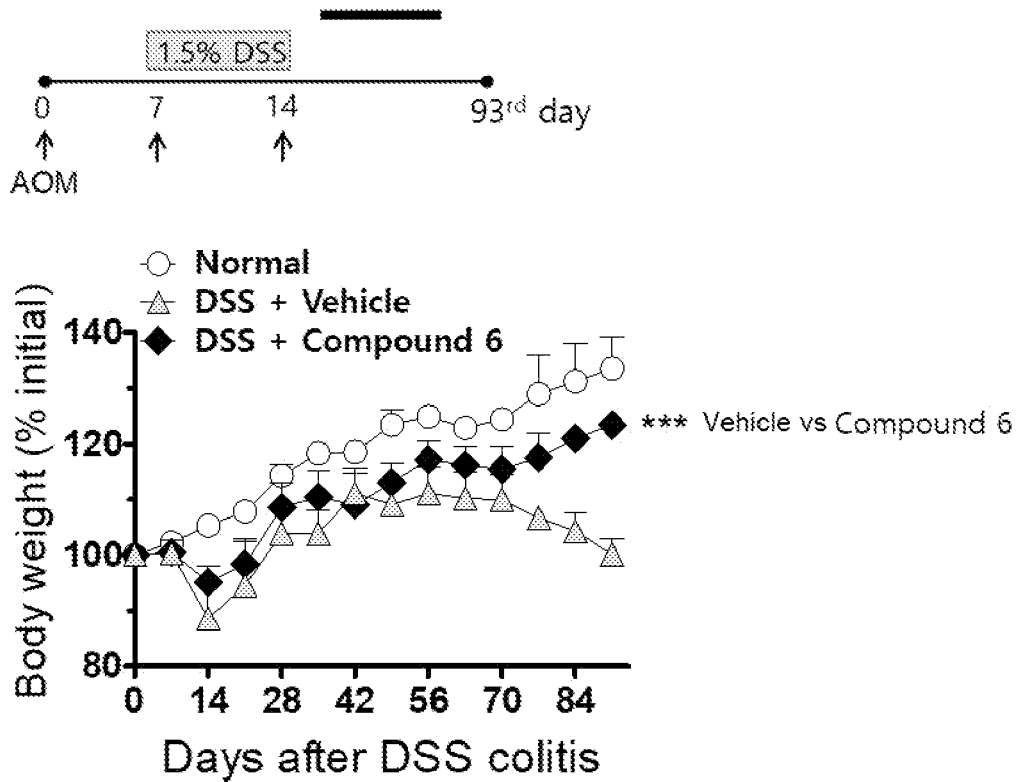
FIGS. 13 and 14 illustrate effects of the compound of an embodiment of the present invention on treating colon cancer in AOM/DSS-colorectal cancer animal models, and specifically, show changes in the body weight (FIG. 13) and the number and size of tumors (FIG. 14) of mice (Normal) not administered with AOM/DSS, mice (DSS+Vehicle) administered with AOM/DSS, and mice (DSS+Compound 6) administered with Compound 6 after colon cancer was induced.
Figure 14:
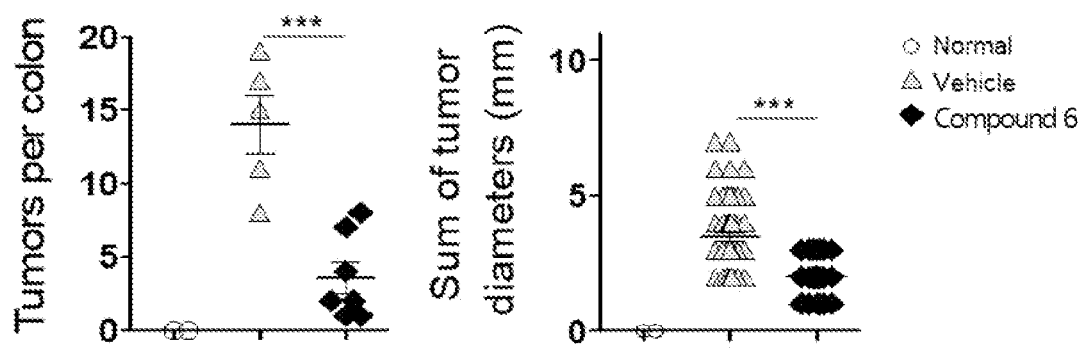

The effects of Compound 6 according to an embodiment of the present invention on treating colon cancer was confirmed. From the 50th to 63rd days of the experiment, DSS was administered on the 7th and 14th days after AOM administration to the mice to induce colon cancer, and Compound 6 was administered 14 times from the 50th to the 63rd days. As a result, the control (AOM/DSS+Vehicle) showed a decrease in the body weight after 70 days, but the group administered with Compound 6 (AOM/DSS+Compound 6) showed an increase in the body weight similar to that of normal mice (Normal) (FIG. 13). In addition, it was confirmed that the number of tumors was significantly smaller in the compound 6 administration group and the size was also significantly smaller than the control (FIG. 14). That is, it was confirmed that Compound 6 was effective in treating colon cancer (FIGS. 13 and 14). Therefore, it was confirmed that Compound 6 can be used as an effective preventive and therapeutic agent for colon cancer.

Example 6: Confirmation of Psoriasis Therapeutic Effect

Figure 15:
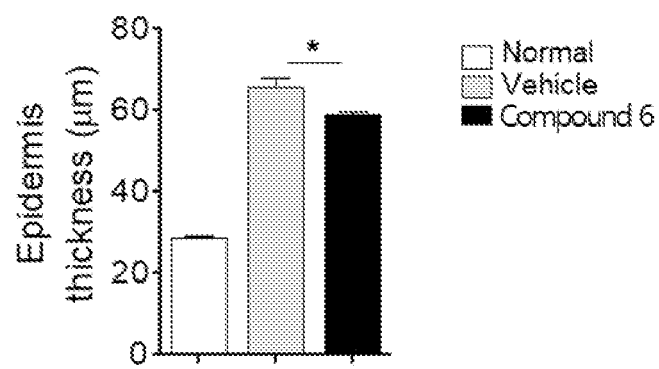
FIGS. 15 to 17 illustrate effects of the compound of an embodiment of the present invention on treating psoriasis in animal models, and specifically, show effects of decreasing epithelial thickness (FIG. 15), effects of inhibiting the expression of skin lesion inflammatory promoting factors (IL-17a, and S100a8) (FIG. 16) and effects of promoting the expression of inflammatory suppressing factors (Foxp3, and IL-10) (FIG. 17).
Figure 16:
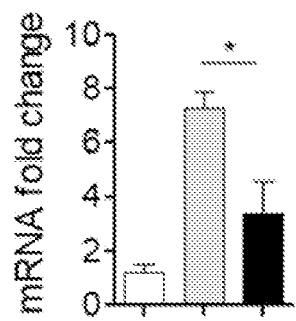
Figure 16:
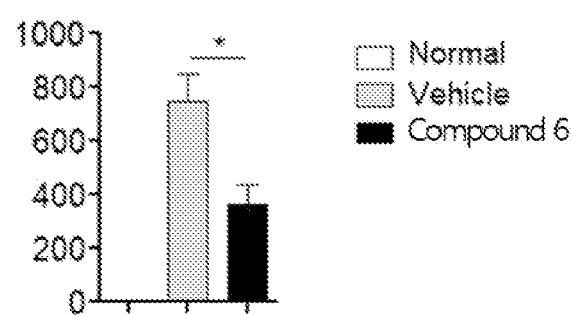
Figure 17:
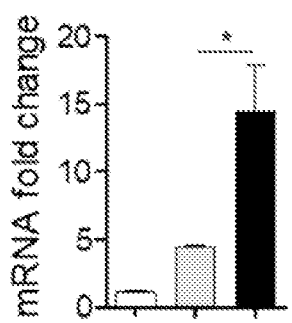
Figure 17:
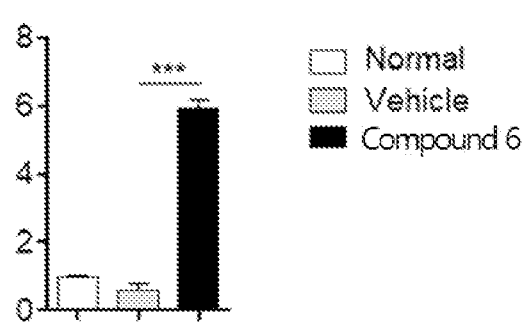

In order to investigate the therapeutic effects of the compounds according to an embodiment of the present invention prepared as above on psoriasis, the following experiments were implemented (FIGS. 15 to 17).

Hair on the back of female BALB/C mice (8-10 weeks old) was shaved using a shaver and shaving cream, and 62.5 mg of 5% imiquimod cream was applied daily for 6 days to the shaved skin from the next day. Vaseline cream was applied to control mice (Vehicle). In the compound 6 administration group according to an embodiment of the present invention, 10 mg/kg of the compound per mouse was completely added to an ethanol-Cremophor EL mixture (1:1, v/v) corresponding to 15% (v/v) of the administered dose, and then, was diluted in phosphate buffered saline to prepare the final ethanol:Cremophor EL:phosphate buffered saline (7.5:7.5:85, v/v/v), followed by oral administration with 200 μl of the prepared solution daily for a total of 6 times from the 0th to the 5th days of the experiment. On the 6th day of the experiment, back skin tissues of mice were obtained to perform histology and mRNA experiments.

As a result, it was confirmed that the epithelial thickness was significantly reduced in the compound 6 orally administration group (FIG. 15), IL-17a and S100a8 mRNA expression levels which promote inflammation in skin lesions were significantly reduced (FIG. 16), as well as Foxp3 and IL-10 which induces inhibition of inflammation in skin lesions were markedly increased (FIG. 17). Therefore, it was confirmed that Compound 6 can be used as an effective therapeutic agent for psoriasis.

Example 7: Confirmation of Graft-Versus-Host Disease Therapeutic Effects

Figure 18:
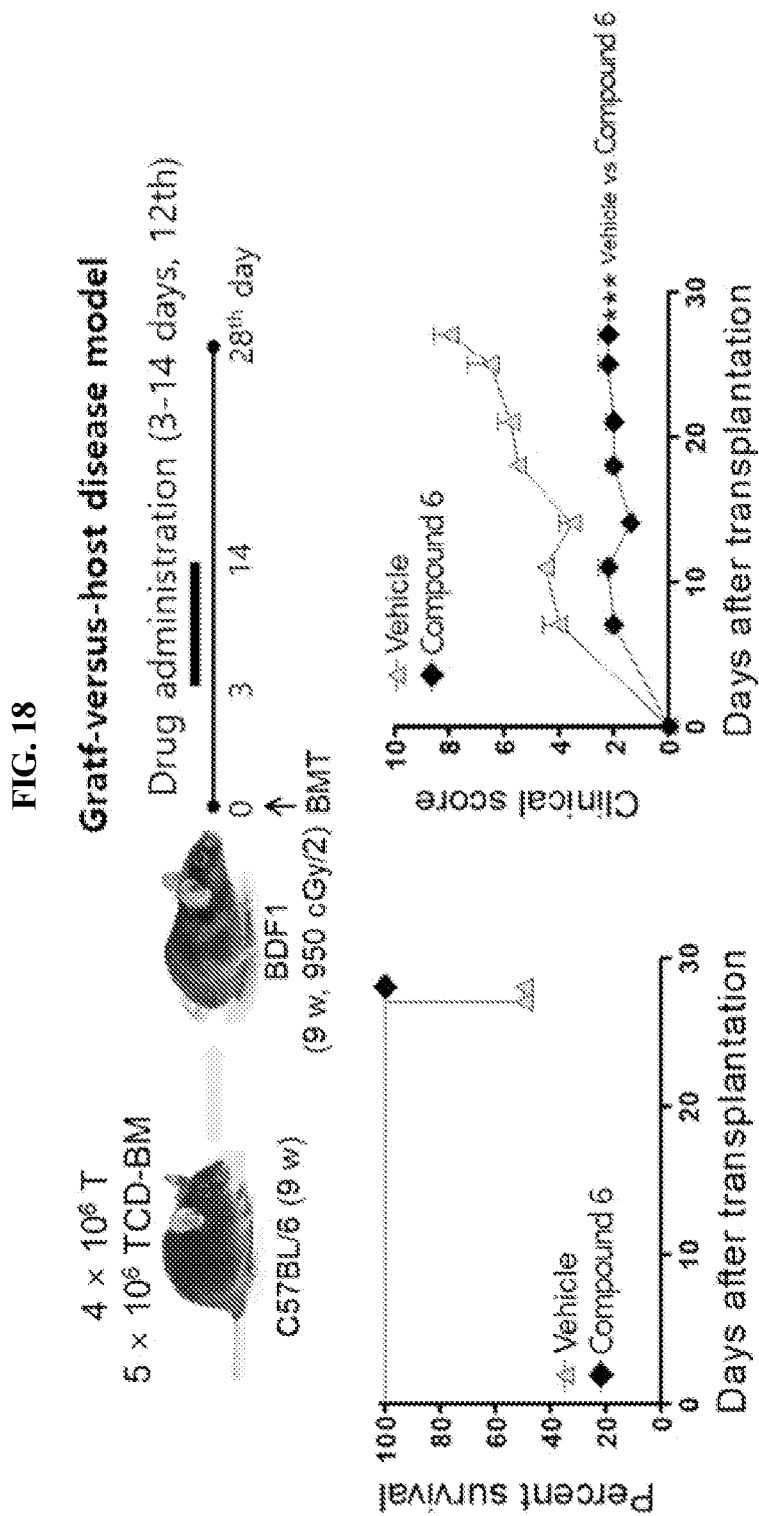
FIGS. 18 and 19 illustrate effects of the compound of an embodiment of the present invention on treating a graft-versus-host disease (GVHD) in B6→BDF1 animal model, and specifically, show the survival rate of mouse after transplantation and clinical score (FIG. 18), and pathological score (FIG. 19).
Figure 19:
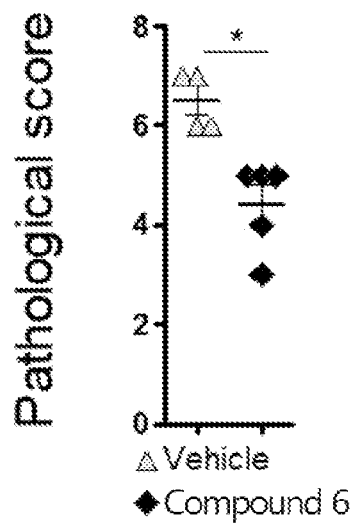

In order to investigate the therapeutic effects of the compounds according to an embodiment of the present invention prepared as above on graft-versus-host disease, Compound 6 was administered to a graft-versus-host disease model to evaluate its efficacy (FIGS. 18 and 19).

The spleen of C57BL/6 mice (8 to 12 weeks old, female, 18±3 g) was excised, pulverized by adding RPMI medium, and then passed through a 40 μm cell strainer (BD Falcon), thereby obtaining a single cell suspension. The single cell suspension was centrifuged (1200 rpm, 5 minutes), and after discarding the supernatant, 1 ml of ACK (ammonium chloride/potassium bicarbonate) lysis buffer (0.15 M NH4Cl, 1 mM KHCO3, 0.1 mM Na2 EDTA) was added, followed by stirring for 1 minute and then washing the same with RPMI medium. After centrifugation, the cell suspension was reacted on mouse CD90.2 microbeads (Miltenyi Biotec, Cat No. 130-121-278) at 4° C. for 20 minutes. After complementation of the reaction, the cell suspension was centrifuged, washed with 10 ml of autoMACS® Running Buffer (Miltenyi Biotec, Cat No. 130-091-221), and then resuspended with 3 ml of autoMACS® Running Buffer. Then, CD90.2$^+$ T cells were obtained from the cell suspension using Auto MACS pro (Miltenyi Biotec) (positive selection). To obtain bone marrow cells to be transplanted together with the obtained CD90.2$^+$ T cells, both femurs and tibias of normal (wild-type) C57BL/6 mice (8-12 weeks old, female, 18±3 g) were aseptically acquired. End portions of the femur and tibia were cut, and the bone marrow was extracted by perfusion of RPMI medium to the bone tissue with a syringe (femur 21G, tibia 26G). The extracted bone marrow was passed through a 40 μm cell strainer to obtain a single cell suspension.

The bone marrow single cell suspension was centrifuged, and after discarding the supernatant, 500 μl of ACK lysis buffer was added, followed by stirring for 30 seconds and washing the solution with RPMI medium. After centrifugation, the suspension was reacted on the mouse CD90.2 microbeads at 4° C. for 20 minutes. After complementation of the reaction, the cell suspension was centrifuged, washed with 10 ml of autoMACS® Running Buffer, and then resuspended with 3 ml of autoMACS® Running Buffer. Then, CD90.2$^-$ T cell-depleted bone marrow cells (TCD-BMs) were obtained from the cell suspension through Auto MACS pro (negative selection). The obtained normal CD90.2$^+$ T cells and normal TCD-BMs were washed with phosphate buffered saline. T cells were prepared by resuspending the same in phosphate buffered saline at 4×10$^6$/ml, while TCD-BM was prepared by resuspending the same in phosphate buffered saline at 5×10$^6$/ml.

The normal BDF1 mice (9 to 11 weeks old, female, 19±3 g) were irradiated with 950 cGy of radiation divided at an interval of 3 hours by using a radiation irradiator. A graft prepared by mixing the prepared CD90.2$^+$ T cells and TCD-BM at a ratio of 1:1 was injected through the tail vein of BDF1 mice at a rate of 100 μl. In the compound 6 administration group according to an embodiment of the present invention, 10 mg/kg of the compound per mouse was completely dissolved in an ethanol-Cremophor EL mixture corresponding to 7.5% (v/v) of the administered dose, and then, was diluted in phosphate buffered saline to prepare the final ethanol:Cremophor EL:phosphate buffered saline (0.375:0.375:9.25, v/v/v), followed by oral administration with 200 μl of the prepared solution daily for a total of 12 times from the 3rd to 14th days of the experiment.

The graft-versus-host disease severity index was evaluated at an interval of 3 to 4 days by visual observation in a severity index system that was classified into a total of 10 points with 0 to 2 points for each item of weight reduction, hair condition, posture, activity and skin change.

As a result of the analysis, the severity index (8±1) of graft-versus-host disease occurred in the solvent control (Vehicle) was significantly decreased by administration (2.2±1.2) of Compound 6 (compared to the solvent control ***, p<0.001, see FIG. 18). Through histopathological analysis of the colon tissue of mice in each experimental group, it was confirmed that the colon tissue inflammatory pathology index was significantly decreased by administration of Compound 6 (see FIG. 19). These results show that Compound 6 can be used as a preventive and therapeutic drug for graft-versus-host disease.

Example 8: Confirmation of Multiple Sclerosis Therapeutic Effect

Figure 20:
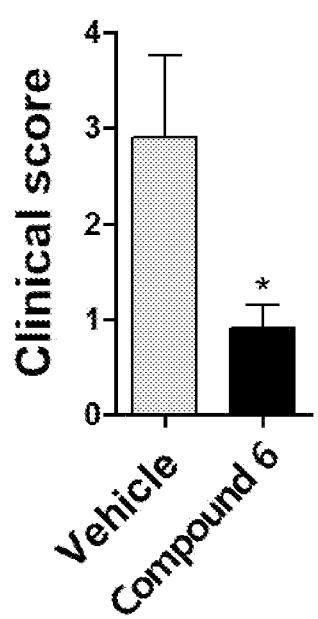
FIG. 20 illustrates effects of the compound of an embodiment of the present invention on treating multiple sclerosis in an autoimmune encephalomyelitis (EAE) model. Herein, it means that the lower the clinical score, the higher the treating effects are.

In order to investigate the therapeutic effects of the compounds according to an embodiment of the present invention prepared as above on multiple sclerosis, experimental autoimmune encephalomyelitis (EAE) was induced in C57BL/6 mice as follows, and Compound 6 was administered to the mice to evaluate its efficacy (FIG. 20).

On day 0 of the experiment, myelin oligodendrocyte glycoprotein (MOG) 35-55 peptide (MOG$_{35-55}$, Peptron) (200 μg), heat killed *Mmycobacterium tuberculosis*, Difco, Cat No. 231141) (500 μg), and an adjuvant (incomplete freund's adjuvant, Sigma Aldrich, Cat No. F5506) were mixed for 7 minutes to form an emulsion. MOG$_{35-55}$ emulsion was subcutaneously injected into both flanks of C57BL/6 mice (7-8 weeks old, female), respectively, and then 100 μl of pertussis toxin (Sigma Aldrich, Cat No. P2980) (200 ng) was administered into the tail vein. On the 2nd day of the experiment, an equal amount of pertussis toxin was administered intravenously. Leakage of the emulsion from the injected site of the mice was checked by visual observation, so as to confirm the onset of multiple sclerosis from the 7th day of the experiment.

In the compound 6 administration group according to an embodiment of the present invention, 10 mg/kg of Compound 6 per mouse was completely dissolved in an ethanol-Cremophor EL mixture corresponding to 7.5% (v/v) of the administered dose, and then, was diluted in phosphate buffered saline to prepare the final ethanol:Cremophor EL:phosphate buffered saline (0.375:0.375:9.25, v/v/v), followed by oral administration with 200 μl of the prepared solution daily for a total of 6 times from the 15th to 20th days of the experiment. The multiple sclerosis index was visually observed and recorded in the severity index system classified into 0-5 stages.

Autoimmune encephalomyelitis symptoms were indexed according to the following items.
0: No symptom
1: Tail enervated
2: Tail enervated, and hindlimb weaken
3: Hindlimb paralysis
4: Hindlimb paralysis, and forelimb weaken
5: Death or being near death As a result of the analysis, on the 21st day of the experiment, the acute response period, the disease severity index was 2.9±1.92 in the solvent control (Vehicle) and 0.92±0.58 in the compound 6 administration group, such that the compound 6 administration group showed lower severity index (*, $p<0.05$, FIG. 20) than the solvent control (Vehicle), and thereby the therapeutic effects of Compound 6 on multiple sclerosis was confirmed.

Example 9: Confirmation of Neutrophilic Asthma Therapeutic Effects

Figure 21:
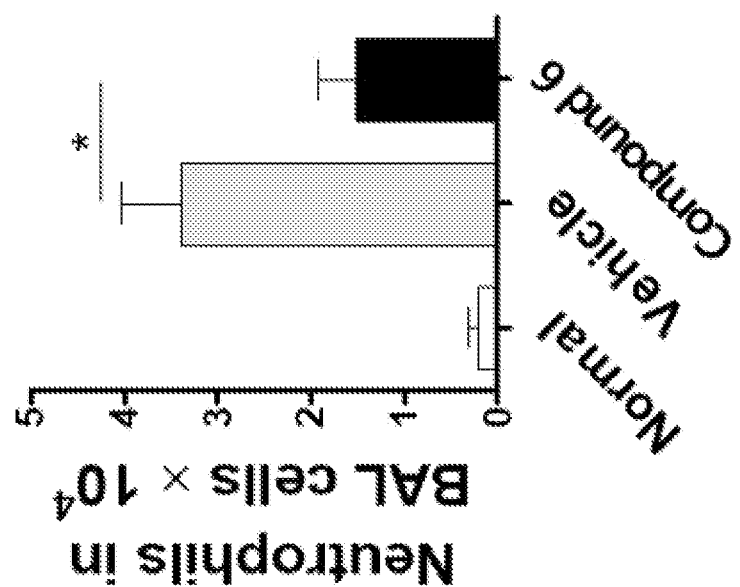
FIG. 21 illustrates effects of the compound of an embodiment of the present invention on treating neutrophilic asthma in a neutrophilic asthma model. Herein, it means that the lower the number of neutrophils in bronchoalveolar lavage (BAL), the higher the treating effects are.
Figure 21:
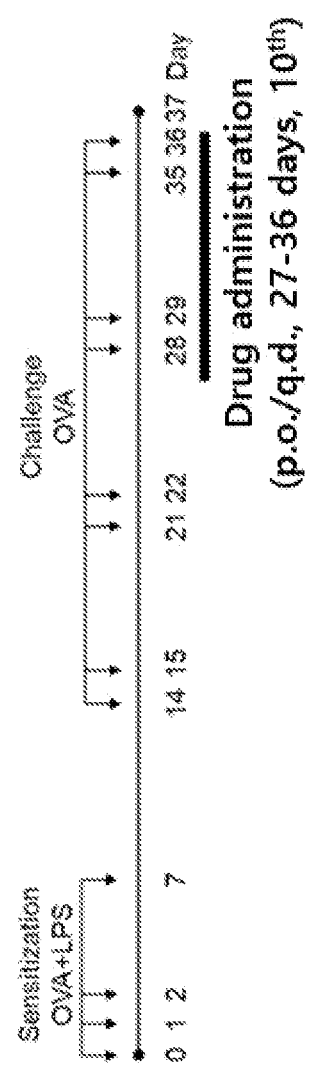

In order to investigate the therapeutic effects of the compounds according to an embodiment of the present invention prepared as above on neutrophilic asthma, Compound 6 was administered to a neutrophilic asthma mouse model to evaluate its efficacy (FIG. 21).

Sensitization was induced in C57BL/6 mice (7 weeks old, female) by intranasally administering 10 μg of LPS (lipopolysaccharide, Sigma Aldrich, Cat No. L2630) and 75 μg of OVA (Ovalbumin, Sigma Aldrich, Cat No. A5503) diluted in phosphate buffered saline (20 μl in total) on the 0th, 1st, 2nd and 7th days of the experiment. From the 14th day of the experiment, 50 μg of OVA diluted in phosphate buffered saline was challenged by intranasal administration for a total of 8 times at an interval of 2 days a week until the 36th day. The intranasal administration was performed after anesthesia using an isoflurane inhalation anesthetic. In the compound 6 administration group according to an embodiment of the present invention, 10 mg/kg of Compound 6 per mouse was completely dissolved in an ethanol-Cremophor EL mixture corresponding to 7.5% (v/v) of the administered dose, and then, was diluted in phosphate buffered saline to prepare the final ethanol:Cremophor EL:phosphate buffered saline (0.375:0.375:9.25, v/v/v), followed by oral administration with 200 μl of the prepared solution daily for a total of 10 times from the 27th to the 36th days of the experiment.

As a result, the number of neutrophils in the bronchoalveolar lavage (BAL) was significantly decreased in the compound 6 administration group compared to solvent control (Vehicle) (FIG. 21), and thereby the therapeutic effects of Compound 6 on neutrophilic asthma was confirmed.

Example 10: Comparison of Effects Between the Inventive Compounds and Comparative Example 1

In order to confirm the superiority of the compounds of the examples according to an embodiment of the present invention compared with the compound of Comparative Example 1 (briefly, "Comparative Example 1"), the following experiments were implemented: (1) measurement of pharmacokinetic parameters; (2) measurement of solubility; (3) confirmation of inhibitory effects on Th17 cell inflammatory activity; (4) confirmation of promotion effects of the production of Foxp3-expressing regulatory T cells; (5) confirmation whether to inhibit activity of drug metabolism-related enzyme; and (6) confirmation of the therapeutic effects of inflammatory bowel disease.

(1) Measurement of Pharmacokinetic Parameters

Figure 22:
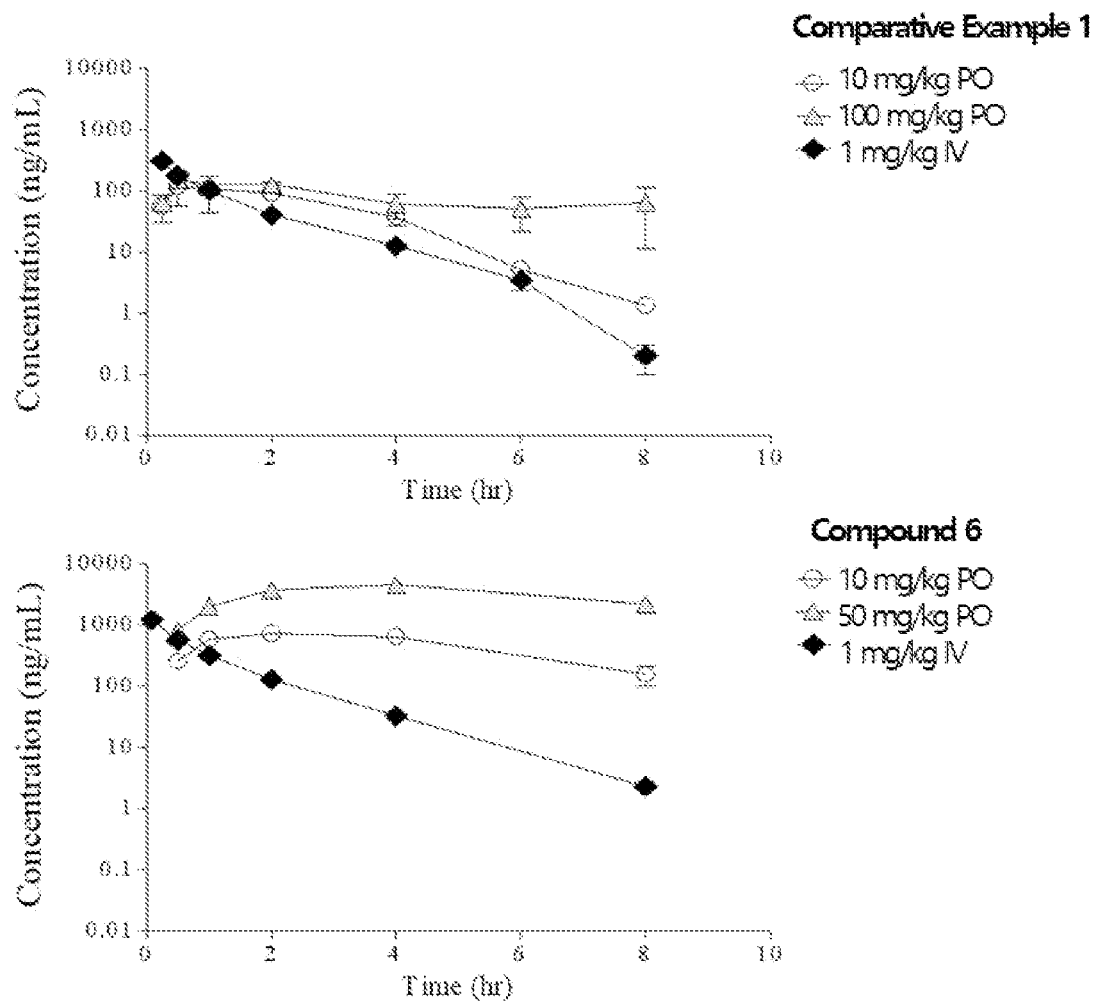
FIG. 22 illustrates changes in blood concentration of Compound 6 of an embodiment of the present invention and Comparative Example 1 over time after oral administration (PO) or intravenous administration (IV) thereof.

Pharmacokinetic parameters of Compound 6 and Comparative Example 1 were measured (Table 3, and FIG. 22).

For rats, an oral administration group was fasted for 16 hours, and an intravenous administration group was subjected to intravenous administration with 10 mL/kg of solution prepared by completely dissolving Compound 6 in an ethanol-Cremophor EL mixture corresponding to 7.5% (v/v) of the administered dose, and then diluting in phosphate buffered saline so as to be the final ethanol:Cremophor EL:phosphate buffered saline (0.375:0.375:9.25, v/v/v), without fasting, at the dose concentration listed in Table 3. The oral administration group was supplied with food about 4 hours after administration. Blood collection was performed on the intravenous administration group after 0.083, 0.5, 1, 2, 4, 8, 24 hours from the administration and on the oral administration group after 0.5, 1, 2, 4, 8, 12, 24 hours from the administration, and plasma was recovered using centrifugation. In the recovered plasma, the drug concentration in the plasma was measured using UHPLC-MS/MS method.

As listed in Table 3, it was confirmed that, in the case of orally administering Compound 6 at a concentration of 10 mg/kg, the bioavailability (F %), the AUClast and Cmax were increased 1.9, 5.9 and 11.9 times, respectively, compared to the case of orally administering Comparative Example 1 at a concentration of 10 mg/kg. In addition, it was confirmed that, in the case of orally administering Compound 6 at a concentration of 50 mg/kg, the bioavailability (F %), the AUClast and Cmax were increased 67.2, 66.8 and 30.2 times, respectively, compared to the case of orally administering Comparative Example 1 at a concentration of 100 mg/kg. From the above results, it was confirmed that Compound 6 could exhibit drug efficacy even in a small amount compared to Comparative Example 1.

TABLE 3

| Administration compound | Comparative Example 1 | | | Compound 6 | | |
|---|---|---|---|---|---|---|
| Section | G1 | G2 | G3 | G4 | G5 | G6 |
| Administration concentration (mg/kg) | 10 | 100 | 1 | 10 | 50 | 1 |
| Administration route | Oral (PO) | Oral (PO) | Intravenous (IV) | Oral (PO) | Oral (PO) | Intravenous (IV) |
| Cmax or C0 (ng/mL) | 126.2 | 151.9 | 405.7 | 741.67 | 4590.00 | 1422.77 |
| Tmax (hr) | 1.0 | 0.5 | — | 2.00 | 4.00 | — |
| t1/2 (hr) | 0.9 | 6.8 | 0.8 | 2.0 | 3.83 | 1.04 |
| AUClast (ng · hr/mL) | 366.0 | 644.2 | 183.1 | 4346.02 | 43059.37 | 1164.82 |
| CL (mL/hr/kg) | — | — | 430.5 | — | — | 862.26 |
| Vdss (mL/kg) | — | — | 310.7 | — | — | 923.76 |
| Dose ratio | 1.0 | 10.0 | — | 1 | 5 | — |

TABLE 3-continued

| Administration compound | Comparative Example 1 | | | Compound 6 | | |
|---|---|---|---|---|---|---|
| Section | G1 | G2 | G3 | G4 | G5 | G6 |
| Cmax ratio | 1.0 | 1.2 | — | 1.0 | 6.2 | — |
| AUClast Ratio | 1.0 | 1.8 | — | 1.0 | 9.9 | — |
| Bioavailability (F %) | 20.0 | 1.1 | — | 37.3 | 73.9 | — |

(2) Measurement of Solubility

The solubility of Compound 6 and Comparative Example 1 was measured.

After dissolving Compound 6 in ethanol, the solubility was measured and analyzed using a SIRIUS T3 machine.

As listed in Table 4, it was confirmed that the log P value of Compound 6 was greater than that of Comparative Example 1, and the pH-metric solubility molarity was about 3.92 times.

TABLE 4

| pH-metric results | | |
|---|---|---|
| Section | Comparative Example 1 | Compound 6 |
| logP | 2.80 | 3.04 |
| Molarity | 3.65 µM | 14.3 µM |
| Weight/ml | 1.248 µg/ml | 6.104 µg/ml |

(3) Confirmation of Inhibitory Effects on Th17 Cell Inflammatory Activity

Figure 23:
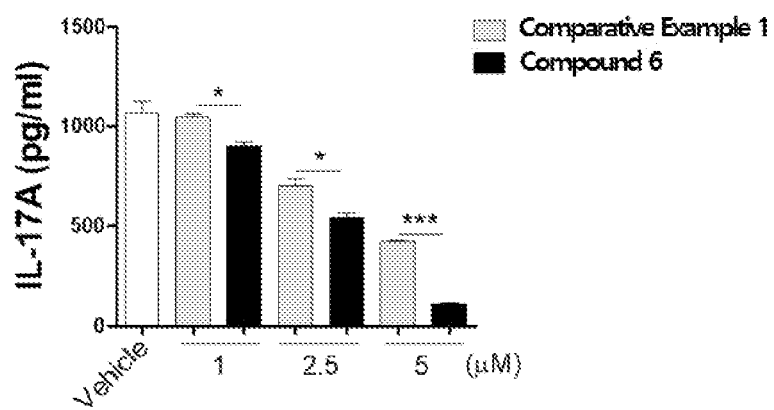
FIG. 23 illustrates effects of Compound 6 of an embodiment of the present invention and Comparative Example 1 on inhibiting the activity of Th17 cells producing IL-17A after treatment therewith.

The inhibitory effects of Compound 6 and Comparative Example 1 on the inflammatory activity of Th17 cells, which are key causing cells of autoimmune disease, were compared (FIG. 23).

The spleen of C57BL/6 mice (8 to 12 weeks old, female) was excised, pulverized by adding IMDM medium, and then passed through a 40 µm cell strainer (BD Falcon), thereby obtaining a single cell suspension. The single cell suspension was centrifuged (1200 rpm, 5 minutes), and after discarding the supernatant, 1 ml of ACK lysis buffer was added, followed by stirring for 1 minute and then washing the same with RPMI medium. After the single cell suspension was centrifuged, T-cells were separated using a Mouse CD4 Naive T cell Enrichment Kit (Invitrogen). The separated T-cells were prepared by resuspending them in RPMI-fetal bovine serum (FBS) 10%+2-ME (mercaptoethanol) medium at $1\times10^6$/ml. For T-cell activation, 5 µg/ml anti-CD3 (eBioscience™) was dispensed by 100 µl onto a 96-well plate, reacted in a cell incubator (37° C., 5% $CO_2$ incubator) for 4 hours, and washed with phosphate buffered saline to prepare the plate. The T-cells were dispensed by 200 µl onto the prepared plate, and each well was treated with 2 µg/ml of anti-CD28 (eBioscience™), 3 ng/ml of TGFβ-1 (R&D systems), 10 ng/ml of IL-2 (R&D systems), 5 µg/ml of anti-mouse IFN-γ (Bio X cell), and 5 µg/ml of anti-mouse IL-4 (Bio X cell). Each 5 µl of compounds at concentrations of 1.0 µM, 2.5 µM and 5 µM diluted in RPMI-fetal bovine serum 10%+2-ME medium was used for treatment, followed by culturing the same in a cell incubator (37° C., 5% $CO_2$ incubator) for 3 days. As a control, 50 µl of 0.05% dimethylsulfoxide (DMSO)/RPMI medium was used for treatment. After 3 days, in order to confirm inhibitory effects of the compounds on the inflammatory activity of Th17 cells, the cultured medium was recovered to confirm IL-17A with flex set (BD biosciences)

To confirm IL-17A cytokine, 25 µl of the recovered medium and 25 µl of assay diluent buffer were put in FACS tubes (BD falcon), and the sample was diluted 1 to 2 (1/2). 1 µl of capture bead was put into 49 µl of capture bead diluent to prepare 50 µl of capture bead solution per sample. After mixing the capture bead solution by vortexing, it was added to the FACS tubes containing each sample by 50 µl, followed by vortexing again, and left at room temperature for 1 hour. After 1 hour, 1 µl of PE detection reagent was added to 49 µl of PE detection reagent diluent to prepare 50 µl of PE detection solution per sample. After vortexing the PE detection solution, it was added to the FACS tubes containing the capture bead solution and the sample by 50 µl. After vortexing the FACS tubes, they were placed at room temperature for 1 hour. After 1 hour, 1 ml of CBA wash buffer was added per tube, and centrifugation was performed at 400 g for 5 minutes, then the supernatant was removed. After weakly vortexing, 150 µl of Fix buffer was added and weakly vortexed, followed by analysis using flow cytometry.

As a result, it was confirmed that IL-17A production of Th17 cells was significantly decreased by Compound 6 compared to Comparative Example 1 (FIG. 23).

(4) Confirmation of Promotion Effects of the Production of Foxp3-Expressing Regulatory T Cells (Treg)

Figure 24:
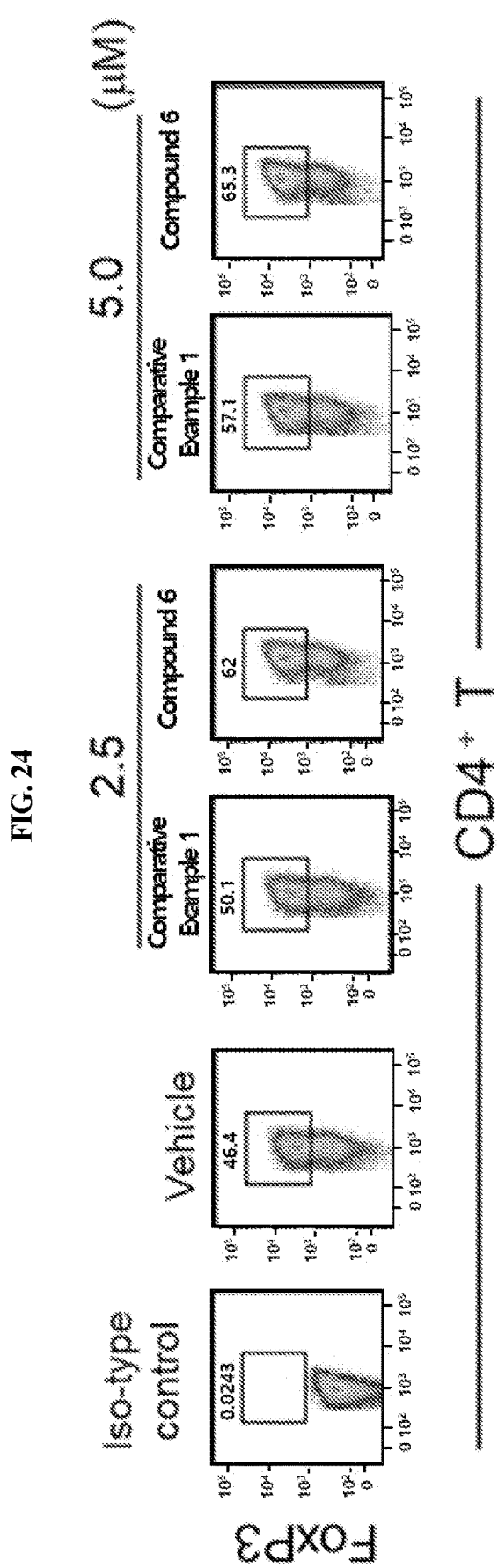
FIG. 24 illustrates effects of Compound 6 of an embodiment of the present invention and Comparative Example 1 on promoting the generation of regulatory T cells expressing Foxp3 after treatment therewith.

The promotion effects of Compound 6 and Comparative Example 1 on the production of "FoxP3-expressing regulatory T cells," which play an important role in maintaining immune tolerance, were compared (FIG. 24). $CD4^+$ T cells were separated and cultured in the same experimental method as in FIG. 4, then treated with each 5 µl of compounds at concentrations of 2.5 µM and 5 µM diluted in RPMI-fetal bovine serum 10%+2ME medium. After culturing in a cell incubator (37° C. 5% CO2 incubator) for 3 days, analysis was performed. As a control, 5 µl of 0.05% dimethylsulfoxide (DMSO)/RPMI medium was treated. After 3 days, in order to confirm the effects of production of the regulatory T cells, the cultured cells were recovered and Foxp3 protein expression was measured in the same manner as in FIG. 4.

As a result, it was confirmed that the production of Foxp3-expressing regulatory T cells was significantly increased by Compound 6 compared to Comparative Example 1 (FIG. 24).

(5) Confirmation Whether to Inhibit Activity of Drug Metabolism-Related Enzyme

The activity of CYP isoenzyme, which is a drug metabolism-related enzyme, was measured.

Live human hepatocyte cell lines (Corning, Cat No. 454551) were collected using a plating medium, seeded on a 24-well plate so that a cell density thereof was $0.4\times10^6$ cells/well, and cultured for 2 to 4 hours. After replacing the plating medium with a hepatocyte culture medium, the hepatocytes were cultured for 24 hours. After culturing for 24 hours, hepatocytes were treated with Compound 6 at 1, 5, 25 M. The medium containing the compound was changed every 24 hours for 2 days. The cultured cells were recovered to prepare mRNA samples. mRNA was extracted from the recovered cells by a phenol-chloroform sedimentation method using TRIZOL reagent (Invitrogen, Cat No. 15596018). From the isolated RNA, cDNA was synthesized by reverse transcription, followed by measuring drug metabolizing enzymes CYP1A2, CYP2C9, CYP2C19, CYP2B6, and CYP3A4 through real-time PCR analysis using the Quant Studio™ 7 Flex Real-Time PCR System (Applied Biosystems, CA). Relative values of the enzyme expression levels were compared by the ΔΔct method using GAPDH as a control enzyme. Herein, one (1) fold was set using the control. Results are expressed as % of control compared to control sample.

Table 5 illustrates changes in CYP isoenzyme activity after 10 μM treatment of each compound (Comparative Example 1, Compound 6, Ketoconazole) (% of Control Activity)

TABLE 5

| Section | CYP1A2 | CYP2C9 | CYP2C19 | CYP2D6 | CYP3A4 |
| --- | --- | --- | --- | --- | --- |
| Comparative Example 1 | 64.6 | 91.9 | 24.4 | 93.3 | 107.6 |
| Compound 6 | 88.2 | 94.5 | 93.1 | 101.2 | 85.7 |
| Ketoconazole (0.1 μM, CYP3A4 inhibitor) | 95.4 | 98.6 | 96.7 | 97.9 | 34.7 |

As a result, it was confirmed that Comparative Example 1 inhibited the enzyme activity of CYP2C19 by 24.4% at 10 μM, whereas Compound 6 had little effect on the enzyme activity of CYP2C19. That is, it was confirmed that Compound 6 could be administered in combination with drugs metabolizing CYP2C19.

(6) Confirmation of the Therapeutic Effects of Inflammatory Bowel Disease

The therapeutic effects of Compound 6 and Comparative Example 1 on inflammatory bowel disease were compared. Inflammatory bowel disease was induced in C57BL/6 mice in the same manner as in Example 4, and after oral administration of 10 mg/kg of Compound 6 and Comparative Example 1 to mice, the expression levels of IL-6 and S100a9 mRNA were confirmed in colon tissues.

Figure 25:
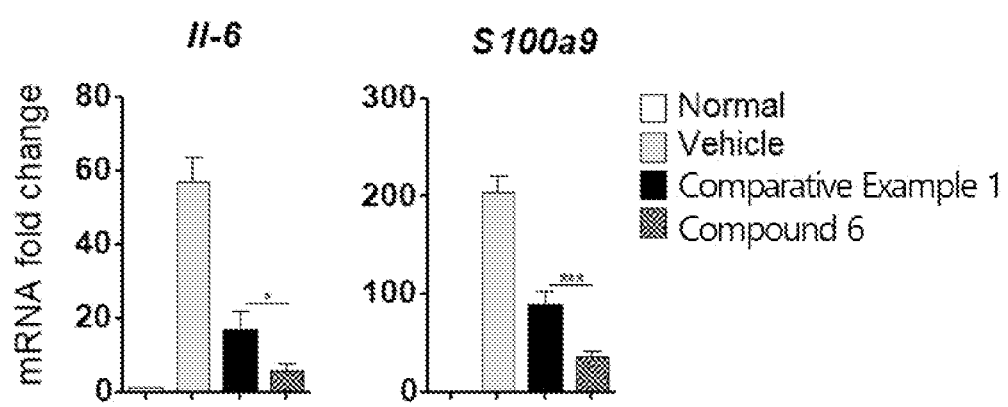
FIG. 25 illustrates effects of Compound 6 of an embodiment of the present invention and Comparative Example 1 on decreasing IL-6 and S100a9 mRNA expression levels after oral administration thereof to mice with inflammatory bowel disease, respectively.

As a result, it was confirmed that the expression levels of IL-6 and S100a9 mRNA in the colon tissues were significantly decreased by Compound 6 compared to Comparative Example 1 (FIG. 25). That is, it was confirmed that Compound 6 showed a higher therapeutic effect of inflammatory bowel disease than Comparative Example 1.

REFERENCE TO AN ELECTRONIC SEQUENCE LISTING

A sequence listing electronically submitted on Aug. 30, 2023, as a XML file named 20230830_LC0532305-C_TU_SEQ.XML, created on Aug. 18, 2023 and having a size of 25,865 bytes, is incorporated herein by reference in its entirety.

What is claimed is:

1. A method for treatment of autoimmune disease, the method comprising administering a pharmaceutical composition to a subject in need thereof,
   wherein the pharmaceutical composition comprises a compound represented by Formula 1 below, a stereoisomer thereof or a pharmaceutically acceptable salt thereof,
   wherein the autoimmune disease is any one selected from the group consisting of atopy, rheumatoid arthritis, systemic lupus erythematous and type 1 diabetes:

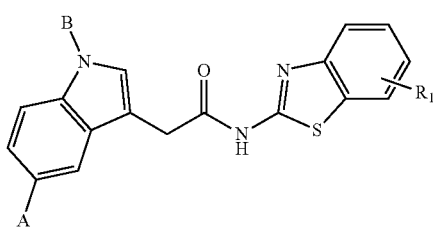

[Formula 1]

wherein, A is hydrogen, halogen, a hydroxyl group, a $C_1$-$C_3$ alkyl group, a $C_2$-$C_3$ alkenyl group, a $C_2$-$C_3$ alkynyl group, a $C_1$-$C_3$ alkoxy group, dimethylamine, —$NO_2$, —CN, —$COOR_2$ or —S($=$O)$_2R_2$, B is hydrogen, a $C_1$-$C_3$ alkyl group, a phenyl group, an acetyl group, —$CH_2C(=O)OR_2$, —$C(=O)OR_2$ or —S($=$O)$_2R_2$, $R_1$ is a substituted or unsubstituted 5-7 membered heterocyclic ring or —$NH_2$, and $R_2$ is a $C_1$-$C_3$ alkyl group.

2. The method according to claim 1, wherein the substituted 5-7 membered heterocyclic ring of the compound represented by Formula 1 is a 5-7 membered heterocyclic ring substituted with a $C_1$-$C_3$ alkyl group, a hydroxyl group or dimethylamine.

3. The method according to claim 1, wherein the substituted or unsubstituted 5-7 membered heterocyclic ring of the compound represented by Formula 1 is any one selected from the group consisting of the following heterocyclic rings:

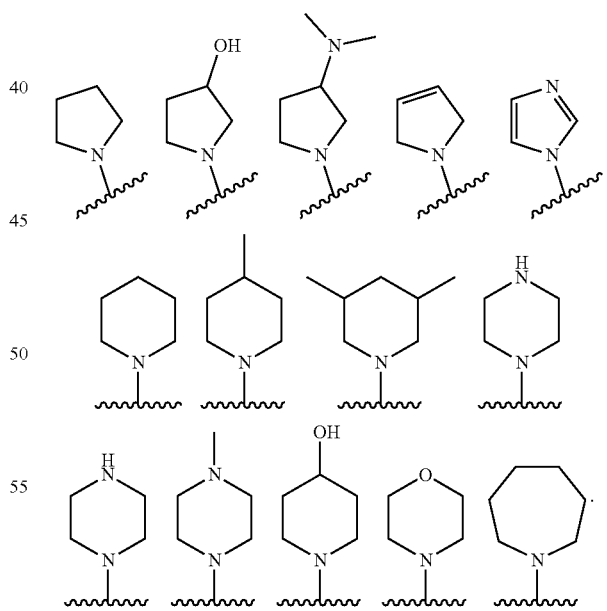

4. The method according to claim 1, wherein the compound represented by Formula 1 is any one selected from the group consisting of the following compounds

| Compound | Structure |
|---|---|
| 1 | 7-amino-benzothiazol-2-yl NH-C(=O)-CH2-(5-chloro-1H-indol-3-yl) |
| 2 | 6-amino-benzothiazol-2-yl NH-C(=O)-CH2-(5-chloro-1H-indol-3-yl) |
| 3 | 5-amino-benzothiazol-2-yl NH-C(=O)-CH2-(5-chloro-1H-indol-3-yl) |
| 4 | 4-amino-benzothiazol-2-yl NH-C(=O)-CH2-(5-chloro-1H-indol-3-yl) |
| 5 | 6-(piperazin-1-yl)-benzothiazol-2-yl NH-C(=O)-CH2-(5-chloro-1H-indol-3-yl) |
| 6 | 6-(morpholin-4-yl)-benzothiazol-2-yl NH-C(=O)-CH2-(5-chloro-1H-indol-3-yl) |

-continued
| Compound | Structure |
|---|---|
| 7 | 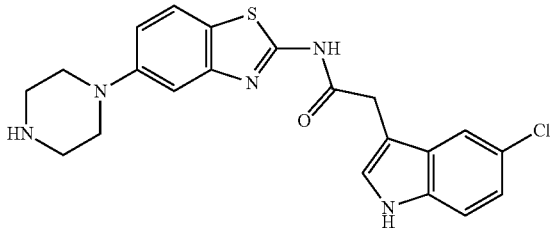 [SMILES: O=C(Cc1c[nH]c2ccc(Cl)cc12)Nc1nc2cc(N3CCNCC3)ccc2s1] |
| 8 | 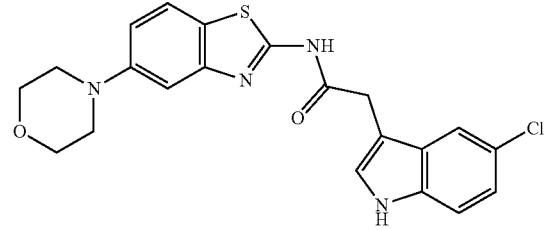 [SMILES: O=C(Cc1c[nH]c2ccc(Cl)cc12)Nc1nc2cc(N3CCOCC3)ccc2s1] |
| 9 | 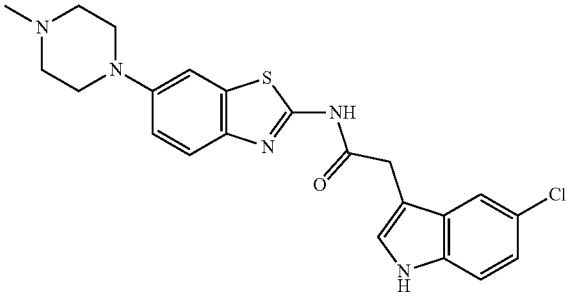 [SMILES: CN1CCN(c2ccc3nc(NC(=O)Cc4c[nH]c5ccc(Cl)cc45)sc3c2)CC1] |
| 10 | 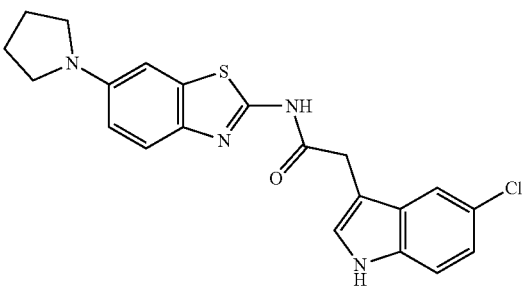 [SMILES: O=C(Cc1c[nH]c2ccc(Cl)cc12)Nc1nc2ccc(N3CCCC3)cc2s1] |
| 11 | 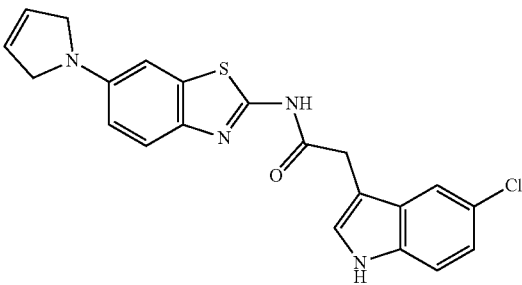 [SMILES: O=C(Cc1c[nH]c2ccc(Cl)cc12)Nc1nc2ccc(N3CC=CC3)cc2s1] |

-continued
| Compound | Structure |
|---|---|
| 12 | 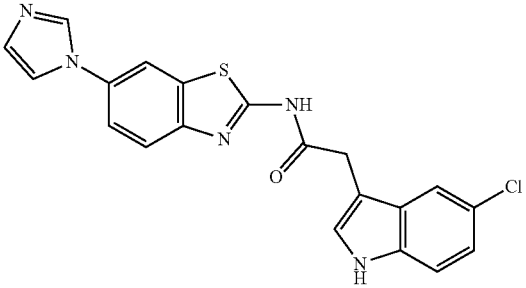 [SMILES: O=C(Cc1c[nH]c2ccc(Cl)cc12)Nc1nc2ccc(-n3ccnc3)cc2s1] |
| 13 | 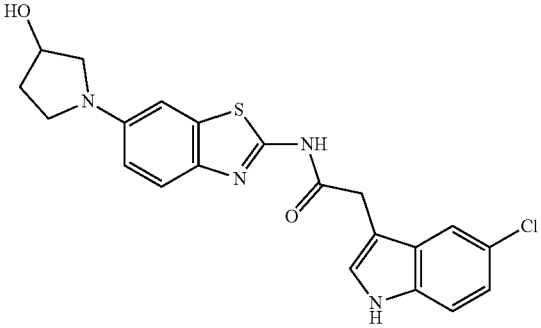 [SMILES: O=C(Cc1c[nH]c2ccc(Cl)cc12)Nc1nc2ccc(N3CCC(O)C3)cc2s1] |
| 14 | 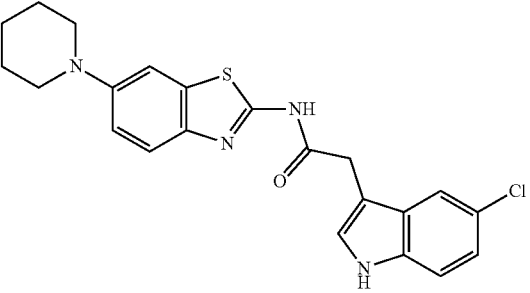 [SMILES: O=C(Cc1c[nH]c2ccc(Cl)cc12)Nc1nc2ccc(N3CCCCC3)cc2s1] |
| 16 | 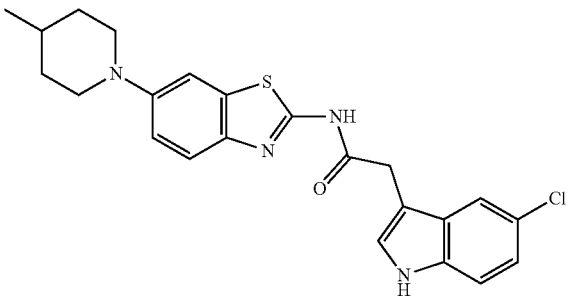 |
| 17 | 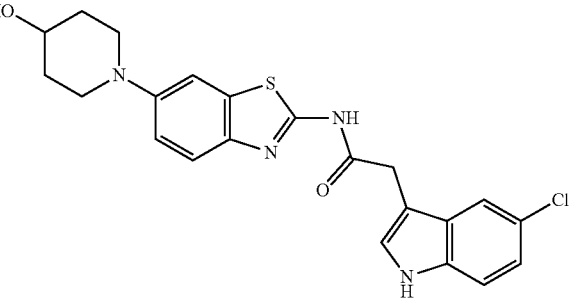 |

-continued
| Compound | Structure |
|---|---|
| 18 | 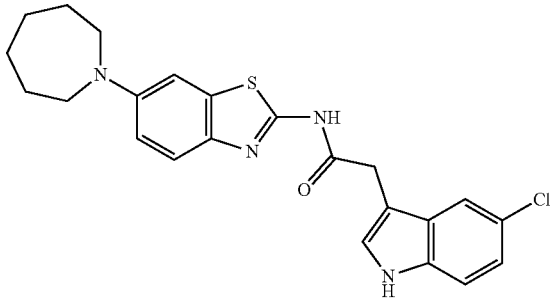 [SMILES: O=C(Cc1c[nH]c2ccc(Cl)cc12)Nc1nc2ccc(N3CCCCCC3)cc2s1] |
| 19 | 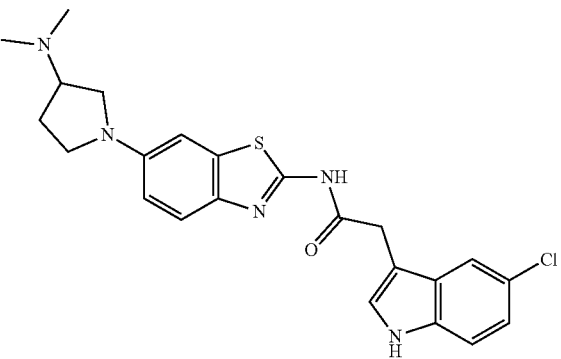 [SMILES: CN(C)C1CCN(c2ccc3nc(NC(=O)Cc4c[nH]c5ccc(Cl)cc45)sc3c2)C1] |
| 20 | 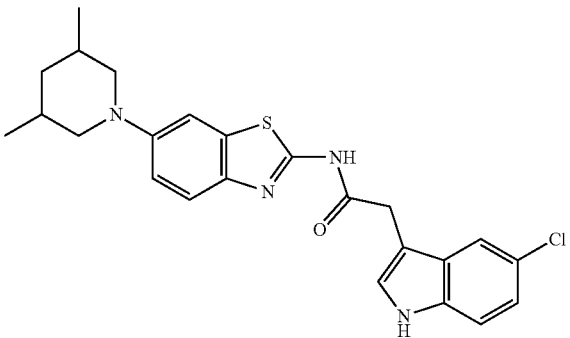 [SMILES: CC1CC(C)CN(c2ccc3nc(NC(=O)Cc4c[nH]c5ccc(Cl)cc45)sc3c2)C1] |
| 21 | 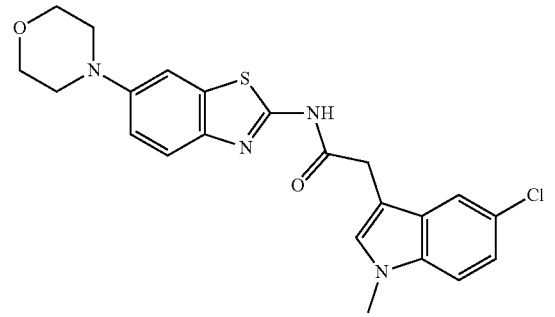 [SMILES: Cn1cc(CC(=O)Nc2nc3ccc(N4CCOCC4)cc3s2)c2cc(Cl)ccc21] |

-continued
| Compound | Structure |
|---|---|
| 22 | 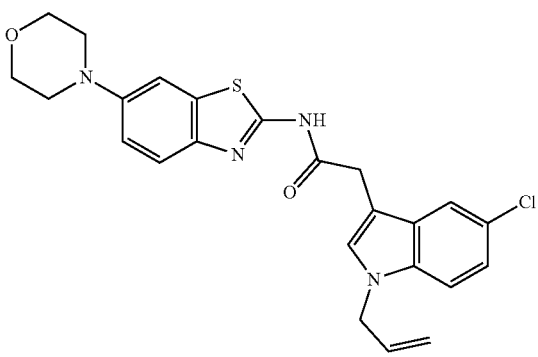 [SMILES: C=CCn1cc(CC(=O)Nc2nc3ccc(N4CCOCC4)cc3s2)c2cc(Cl)ccc21] |
| 23 | 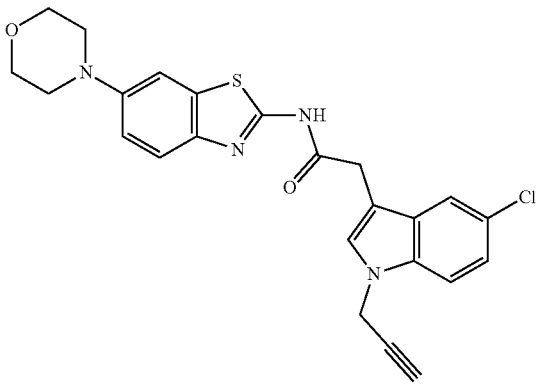 [SMILES: C#CCn1cc(CC(=O)Nc2nc3ccc(N4CCOCC4)cc3s2)c2cc(Cl)ccc21] |
| 24 | 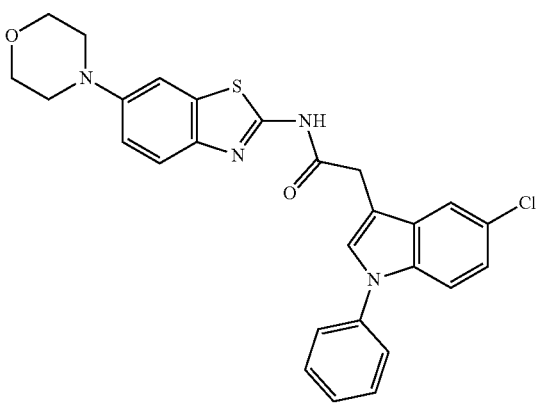 [SMILES: O=C(Cc1cn(-c2ccccc2)c2ccc(Cl)cc12)Nc1nc2ccc(N3CCOCC3)cc2s1] |
| 25 | 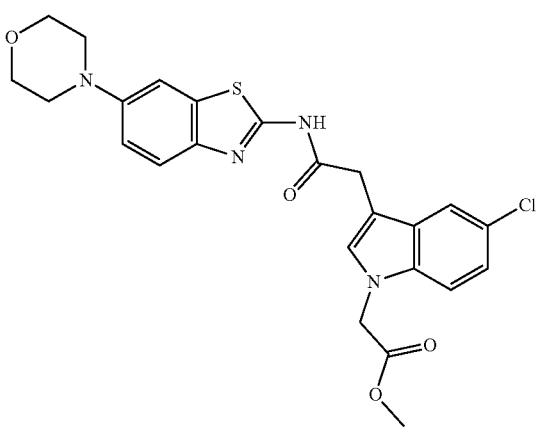 [SMILES: COC(=O)Cn1cc(CC(=O)Nc2nc3ccc(N4CCOCC4)cc3s2)c2cc(Cl)ccc21] |

-continued
| Compound | Structure |
|---|---|
| 26 | 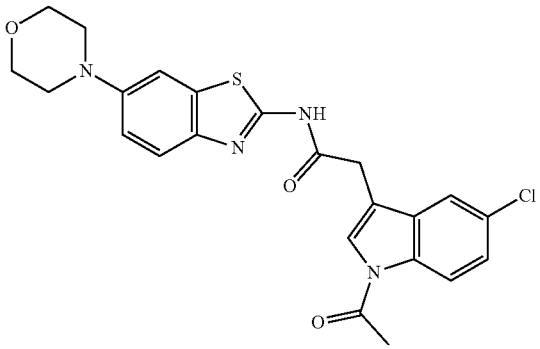 [SMILES: CC(=O)n1cc(CC(=O)Nc2nc3ccc(N4CCOCC4)cc3s2)c2cc(Cl)ccc21] |
| 27 | 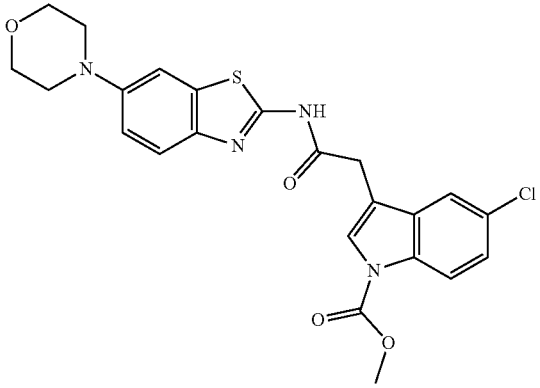 [SMILES: COC(=O)n1cc(CC(=O)Nc2nc3ccc(N4CCOCC4)cc3s2)c2cc(Cl)ccc21] |
| 28 | 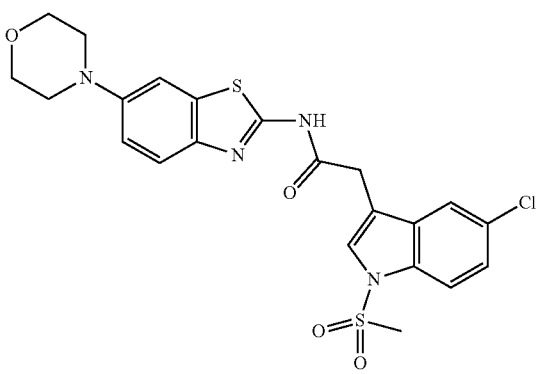 [SMILES: CS(=O)(=O)n1cc(CC(=O)Nc2nc3ccc(N4CCOCC4)cc3s2)c2cc(Cl)ccc21] |
| 29 | 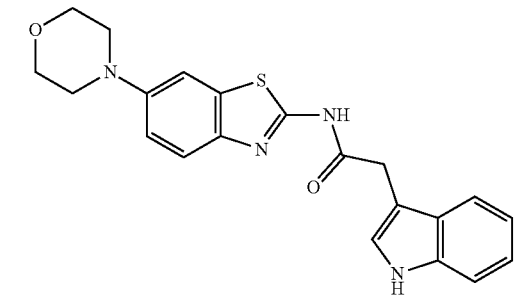 [SMILES: O=C(Cc1c[nH]c2ccccc12)Nc1nc2ccc(N3CCOCC3)cc2s1] |

-continued
| Compound | Structure |
|---|---|
| 30 | 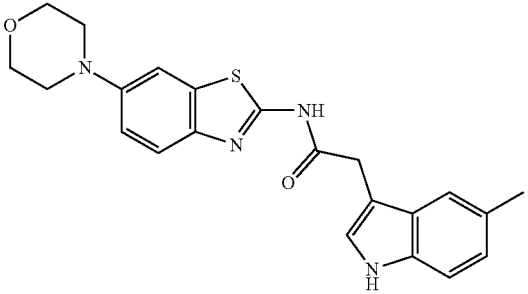 [SMILES: Cc1ccc2[nH]cc(CC(=O)Nc3nc4ccc(N5CCOCC5)cc4s3)c2c1] |
| 31 | 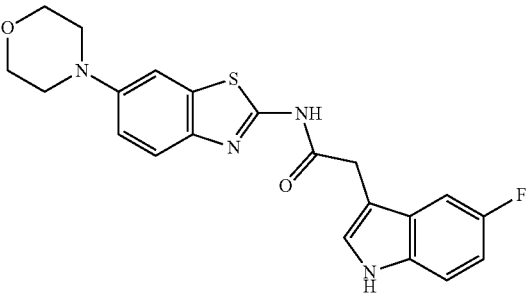 [SMILES: O=C(Cc1c[nH]c2ccc(F)cc12)Nc1nc2ccc(N3CCOCC3)cc2s1] |
| 32 | 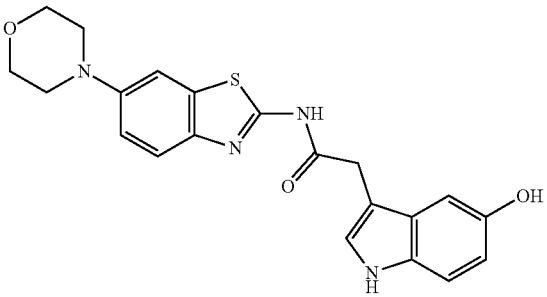 [SMILES: O=C(Cc1c[nH]c2ccc(O)cc12)Nc1nc2ccc(N3CCOCC3)cc2s1] |
| 33 | 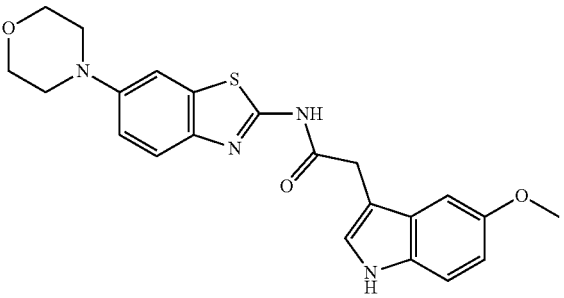 [SMILES: COc1ccc2[nH]cc(CC(=O)Nc3nc4ccc(N5CCOCC5)cc4s3)c2c1] |
| 34 | 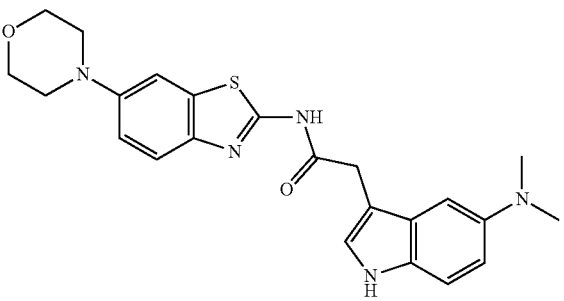 [SMILES: CN(C)c1ccc2[nH]cc(CC(=O)Nc3nc4ccc(N5CCOCC5)cc4s3)c2c1] |

-continued

| Compound | Structure |
|---|---|
| 35 | 6-morpholino-benzothiazol-2-yl NH–C(O)–CH₂–(5-nitro-1H-indol-3-yl) |
| 36 | 6-morpholino-benzothiazol-2-yl NH–C(O)–CH₂–(5-cyano-1H-indol-3-yl) |
| 37 | 6-morpholino-benzothiazol-2-yl NH–C(O)–CH₂–(1H-indol-3-yl-5-carboxylic acid methyl ester) |
| 38 | 6-morpholino-benzothiazol-2-yl NH–C(O)–CH₂–(1H-indol-3-yl-5-sulfonic acid methyl ester) |
| 39 | 6-morpholino-benzothiazol-2-yl NH–C(O)–CH₂–(5-methoxy-1H-indol-3-yl) |

5. A method for treatment of cancer, the method comprising administering a pharmaceutical composition to a subject in need thereof,
wherein the pharmaceutical composition comprises a compound represented by Formula 1 below, a stereoisomer thereof or a pharmaceutically acceptable salt thereof,
wherein the cancer is any one selected from the group consisting of melanoma, liver cancer, gliocytoma, ovarian cancer, colorectal cancer, head and neck cancer, bladder cancer, kidney cell cancer, stomach cancer, breast cancer, metastatic cancer, prostate cancer, gallbladder cancer, pancreatic cancer, blood cancer, skin cancer and lung cancer:

[Formula 1]

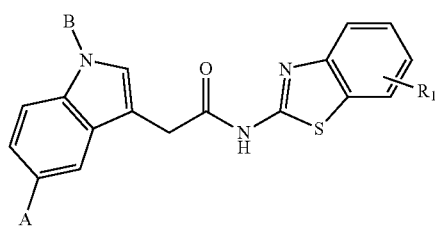

wherein, A is hydrogen, halogen, a hydroxyl group, a $C_1$-$C_3$ alkyl group, a $C_2$-$C_3$ alkenyl group, a $C_2$-$C_3$ alkynyl group, a $C_1$-$C_3$ alkoxy group, dimethylamine, —$NO_2$, —CN, —$COOR_2$ or —$S(=O)_2R_2$,
B is hydrogen, a $C_1$-$C_3$ alkyl group, a phenyl group, an acetyl group, —$CH_2C(=O)OR_2$, —$C(=O)OR_2$ or —$S(=O)_2R_2$,
$R_1$ is a substituted or unsubstituted 5-7 membered heterocyclic ring or —$NH_2$, and
$R_2$ is a $C_1$-$C_3$ alkyl group.

6. The method according to claim 5, wherein the substituted 5-7 membered heterocyclic ring of the compound represented by Formula 1 is a 5-7 membered heterocyclic ring substituted with a $C_1$-$C_3$ alkyl group, a hydroxyl group or dimethylamine.

7. The method according to claim 5, wherein the substituted or unsubstituted 5-7 membered heterocyclic ring of the compound represented by Formula 1 is any one selected from the group consisting of the following heterocyclic rings:

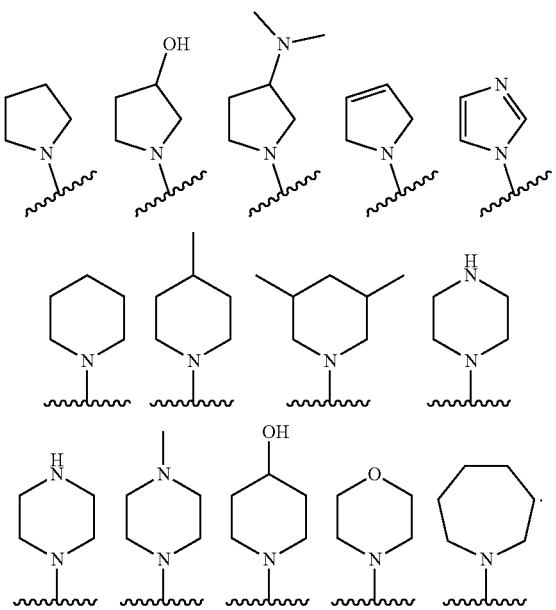

8. The method according to claim 5, wherein the compound represented by Formula 1 is any one selected from the group consisting of the following compounds

| Compound | Structure |
|---|---|
| 1 | ![structure 1] |
| 2 | ![structure 2] |

-continued

| Compound | Structure |
|---|---|
| 3 | 5-amino-benzothiazol-2-yl-NH-C(=O)-CH2-(5-chloro-1H-indol-3-yl) |
| 4 | 4-amino-benzothiazol-2-yl-NH-C(=O)-CH2-(5-chloro-1H-indol-3-yl) |
| 5 | 6-(piperazin-1-yl)-benzothiazol-2-yl-NH-C(=O)-CH2-(5-chloro-1H-indol-3-yl) |
| 6 | 6-morpholino-benzothiazol-2-yl-NH-C(=O)-CH2-(5-chloro-1H-indol-3-yl) |
| 7 | 5-(piperazin-1-yl)-benzothiazol-2-yl-NH-C(=O)-CH2-(5-chloro-1H-indol-3-yl) |
| 8 | 5-morpholino-benzothiazol-2-yl-NH-C(=O)-CH2-(5-chloro-1H-indol-3-yl) |

-continued

| Compound | Structure |
|---|---|
| 9 | 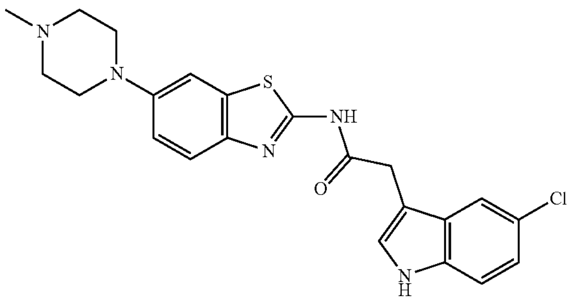 |
| 10 | 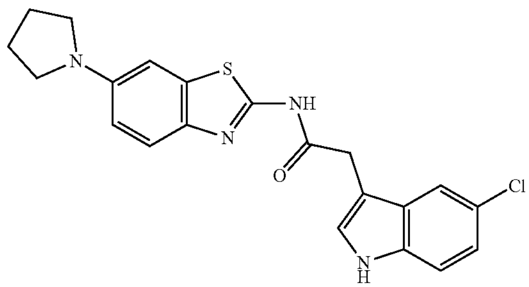 [SMILES: O=C(Cc1c[nH]c2ccc(Cl)cc12)Nc1nc2ccc(N3CCCC3)cc2s1] |
| 11 | 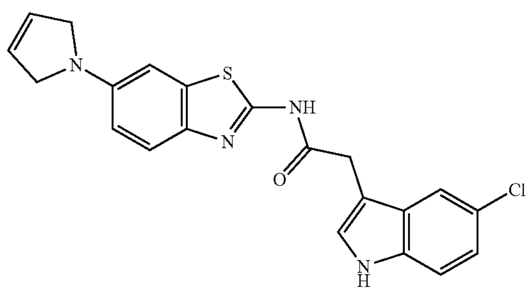 [SMILES: O=C(Cc1c[nH]c2ccc(Cl)cc12)Nc1nc2ccc(N3CC=CC3)cc2s1] |
| 12 | 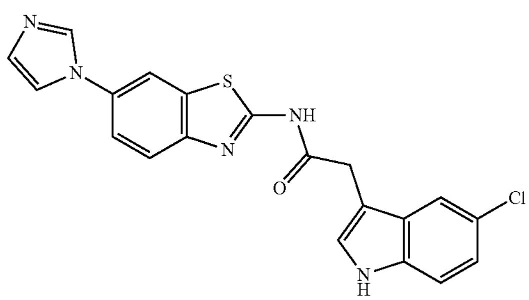 [SMILES: O=C(Cc1c[nH]c2ccc(Cl)cc12)Nc1nc2ccc(-n3ccnc3)cc2s1] |
| 13 | 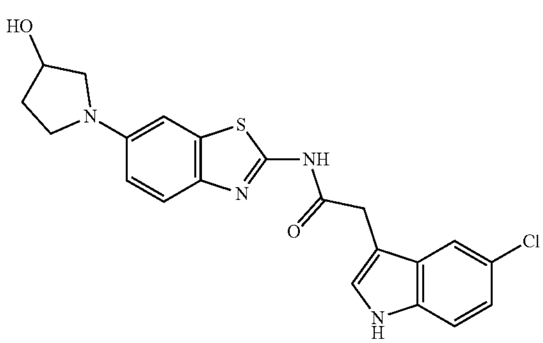 [SMILES: O=C(Cc1c[nH]c2ccc(Cl)cc12)Nc1nc2ccc(N3CCC(O)C3)cc2s1] |

-continued

| Compound | Structure |
|---|---|
| 14 | 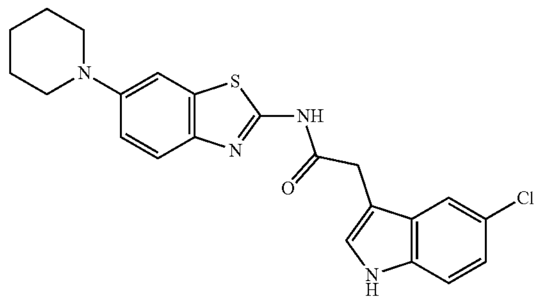 [SMILES: O=C(Cc1c[nH]c2ccc(Cl)cc12)Nc1nc2ccc(N3CCCCC3)cc2s1] |
| 16 | 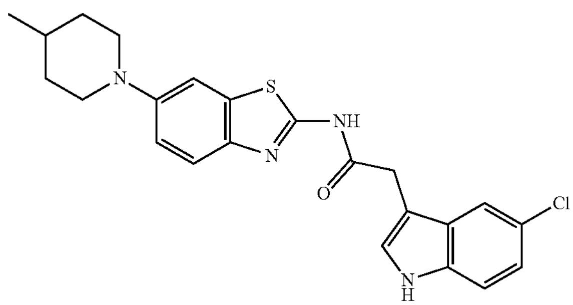 [SMILES: CC1CCN(c2ccc3nc(NC(=O)Cc4c[nH]c5ccc(Cl)cc45)sc3c2)CC1] |
| 17 | 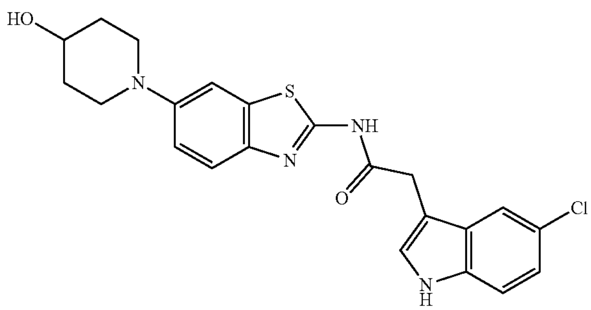 [SMILES: O=C(Cc1c[nH]c2ccc(Cl)cc12)Nc1nc2ccc(N3CCC(O)CC3)cc2s1] |
| 18 | 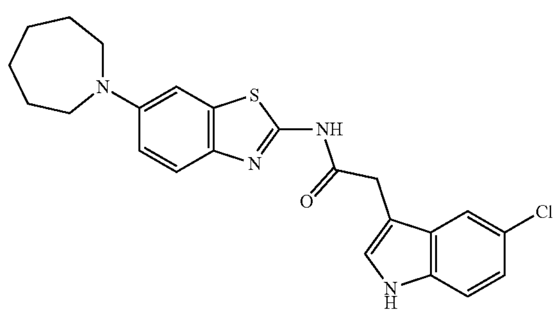 [SMILES: O=C(Cc1c[nH]c2ccc(Cl)cc12)Nc1nc2ccc(N3CCCCCC3)cc2s1] |
| 19 | 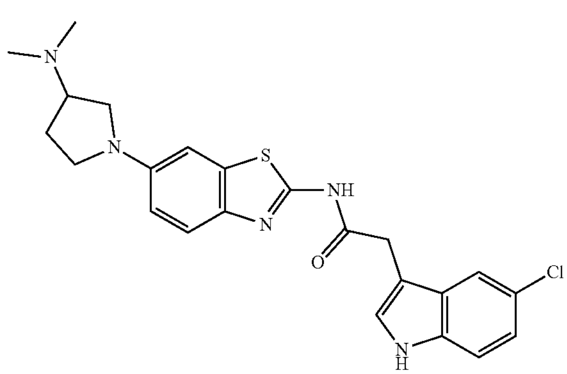 [SMILES: CN(C)C1CCN(c2ccc3nc(NC(=O)Cc4c[nH]c5ccc(Cl)cc45)sc3c2)C1] |

-continued
| Compound | Structure |
|---|---|
| 20 | 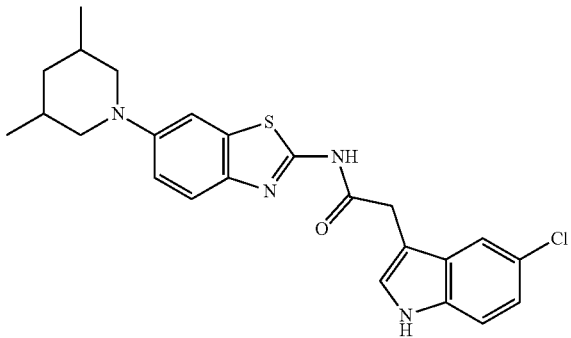 [SMILES: CC1CC(C)CN(c2ccc3nc(NC(=O)Cc4c[nH]c5ccc(Cl)cc45)sc3c2)C1] |
| 21 | 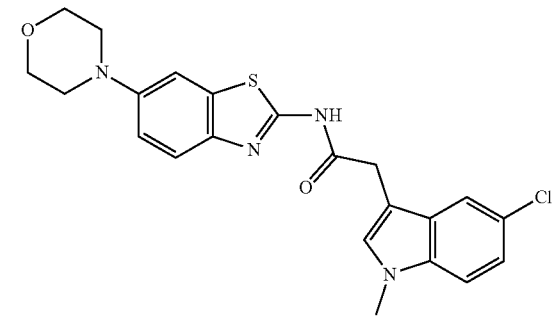 [SMILES: Cn1cc(CC(=O)Nc2nc3ccc(N4CCOCC4)cc3s2)c2cc(Cl)ccc21] |
| 22 | 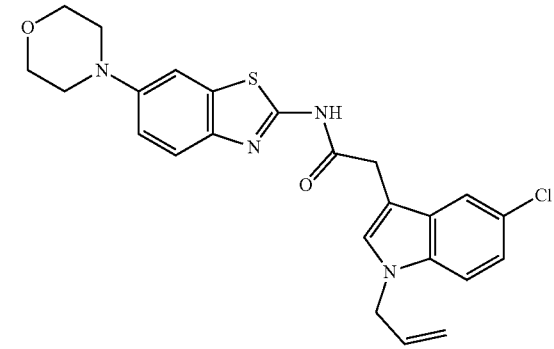 [SMILES: C=CCn1cc(CC(=O)Nc2nc3ccc(N4CCOCC4)cc3s2)c2cc(Cl)ccc21] |
| 23 | 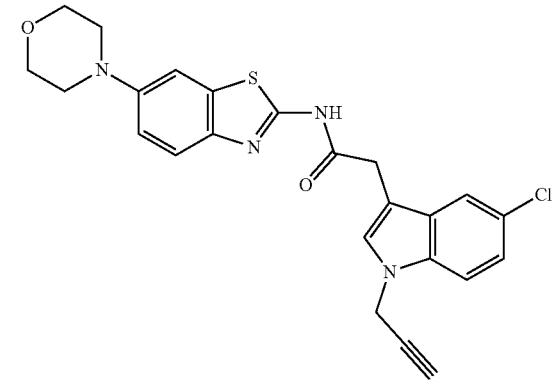 [SMILES: C#CCn1cc(CC(=O)Nc2nc3ccc(N4CCOCC4)cc3s2)c2cc(Cl)ccc21] |

-continued
| Compound | Structure |
|---|---|
| 24 | 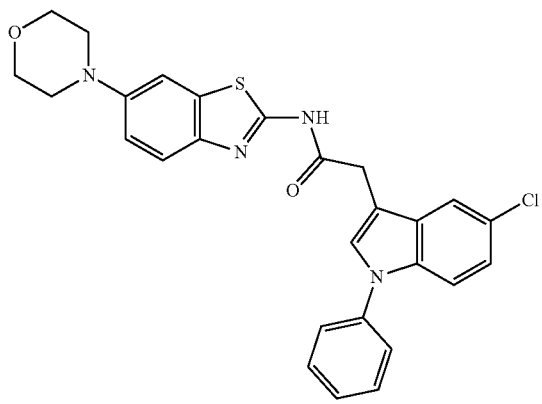 [SMILES: O=C(Cc1cn(-c2ccccc2)c2ccc(Cl)cc12)Nc1nc2ccc(N3CCOCC3)cc2s1] |
| 25 | 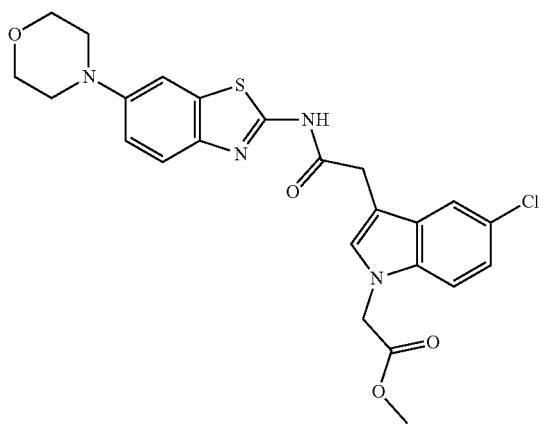 [SMILES: COC(=O)Cn1cc(CC(=O)Nc2nc3ccc(N4CCOCC4)cc3s2)c2cc(Cl)ccc21] |
| 26 | 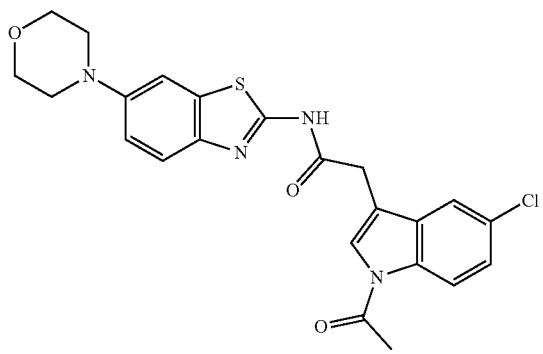 [SMILES: CC(=O)n1cc(CC(=O)Nc2nc3ccc(N4CCOCC4)cc3s2)c2cc(Cl)ccc21] |
| 27 | 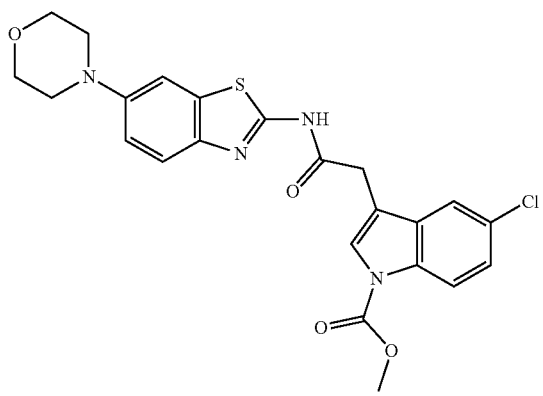 [SMILES: COC(=O)n1cc(CC(=O)Nc2nc3ccc(N4CCOCC4)cc3s2)c2cc(Cl)ccc21] |

-continued
| Compound | Structure |
|---|---|
| 28 | 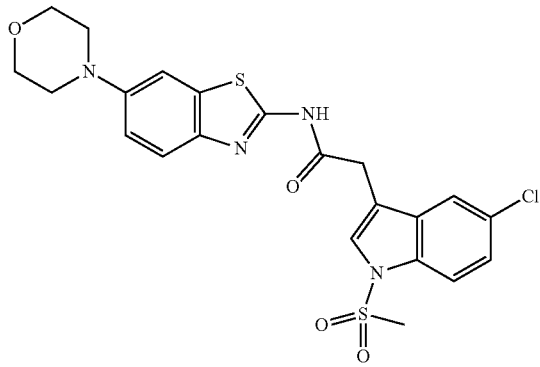 [SMILES: CS(=O)(=O)n1cc(CC(=O)Nc2nc3ccc(N4CCOCC4)cc3s2)c2cc(Cl)ccc21] |
| 29 | 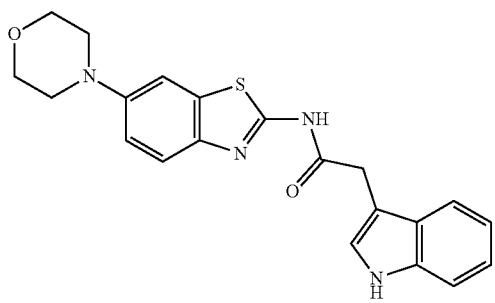 [SMILES: O=C(Cc1c[nH]c2ccccc12)Nc1nc2ccc(N3CCOCC3)cc2s1] |
| 30 | 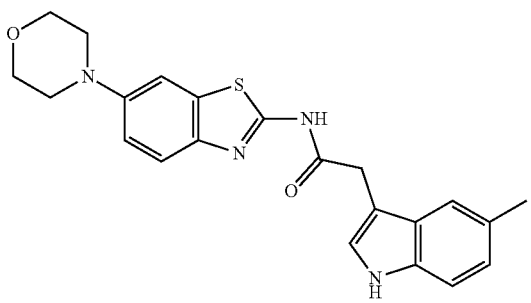 [SMILES: Cc1ccc2[nH]cc(CC(=O)Nc3nc4ccc(N5CCOCC5)cc4s3)c2c1] |
| 31 | 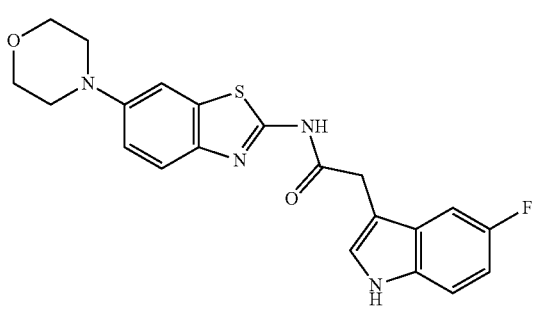 [SMILES: O=C(Cc1c[nH]c2ccc(F)cc12)Nc1nc2ccc(N3CCOCC3)cc2s1] |
| 32 | 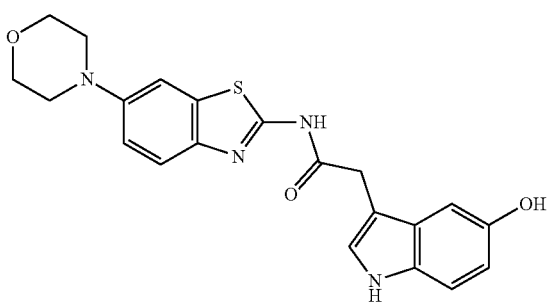 |

-continued

| Compound | Structure |
|---|---|
| 33 | 6-morpholinobenzothiazol-2-yl amide of 2-(5-methoxy-1H-indol-3-yl)acetic acid |
| 34 | 6-morpholinobenzothiazol-2-yl amide of 2-(5-(dimethylamino)-1H-indol-3-yl)acetic acid |
| 35 | 6-morpholinobenzothiazol-2-yl amide of 2-(5-nitro-1H-indol-3-yl)acetic acid |
| 36 | 6-morpholinobenzothiazol-2-yl amide of 2-(5-cyano-1H-indol-3-yl)acetic acid |
| 37 | 6-morpholinobenzothiazol-2-yl amide of 2-(5-(methoxycarbonyl)-1H-indol-3-yl)acetic acid |

| Compound | Structure |
|---|---|
| 38 | methyl 3-(2-((6-morpholinobenzo[d]thiazol-2-yl)amino)-2-oxoethyl)-1H-indole-5-sulfonate |
| 39 | 2-(5-methoxy-1H-indol-3-yl)-N-(6-morpholinobenzo[d]thiazol-2-yl)acetamide |

* * * * *